US005650297A

United States Patent [19]
Takahashi et al.

[11] Patent Number: 5,650,297
[45] Date of Patent: Jul. 22, 1997

[54] DNA ENCODING HUMAN COLONY-STIMULATING FACTORS

[75] Inventors: Masayuki Takahashi, Naruto; Tohru Hirato, Giju-ken; Satoru Nakai, Tokushima-ken; Yeong-Man Hong, Naruto; Naomi Kouno, Shimada; Yoshikatsu Hirai, Tokushima-ken, all of Japan

[73] Assignee: Otsuka Pharmaceutical Co., Ltd., Tokyo, Japan

[21] Appl. No.: 281,147

[22] Filed: Jul. 27, 1994

Related U.S. Application Data

[63] Continuation of Ser. No. 815,603, Jan. 3, 1993, abandoned, which is a continuation-in-part of Ser. No. 304,692, Feb. 1, 1989, abandoned, and a continuation-in-part of Ser. No. 98,105, Sep. 17, 1987, abandoned.

[30] Foreign Application Priority Data

| Sep. 17, 1986 | [JP] | Japan | 61-220750 |
| Jan. 19, 1987 | [JP] | Japan | 62-11025 |
| Jul. 2, 1987 | [JP] | Japan | 62-166388 |
| Feb. 8, 1988 | [JP] | Japan | 63-27241 |
| Mar. 15, 1988 | [JP] | Japan | 63-62841 |

[51] Int. Cl.$^6$ ................................................ C12N 15/27
[52] U.S. Cl. .................... 435/69.5; 438/252.33; 438/320.1; 536/23.5
[58] Field of Search .................... 435/69.1, 69.5, 435/172.3, 252.33, 320.1; 536/23.5

[56] References Cited

U.S. PATENT DOCUMENTS

| 4,675,291 | 6/1987 | Yamamura et al. | 435/172.1 |
| 4,677,063 | 6/1987 | Mark et al. | 435/68 |
| 4,847,201 | 7/1989 | Kaswasaki et al. | 435/69.52 |
| 4,868,119 | 9/1989 | Clark et al. | 435/69.52 |
| 4,879,227 | 11/1989 | Clark et al. | 435/70 |
| 4,929,700 | 5/1990 | Halenbeck et al. | 530/357 |
| 5,026,839 | 6/1991 | Moscatelli et al. | 536/27 |

FOREIGN PATENT DOCUMENTS

| 0249477 | 12/1987 | European Pat. Off. . |
| A261592 | 3/1988 | European Pat. Off. . |
| A276551 | 8/1988 | European Pat. Off. . |
| A328061 | 8/1989 | European Pat. Off. . |
| A410751 | 1/1991 | European Pat. Off. . |
| 169799 | 7/1987 | Japan . |
| WO8604587 | 8/1986 | WIPO . |
| WO8604607 | 8/1986 | WIPO . |
| WO8706954 | 11/1987 | WIPO . |
| WO8803173 | 5/1988 | WIPO . |
| WO8808003 | 10/1988 | WIPO . |
| WO8906546 | 7/1989 | WIPO . |

OTHER PUBLICATIONS

"Amino-terminal Region of Human Macrophage . . . Human M-CSF", by M. Takahashi et al., vol. 161, No. 2, Jun. 15, 1989, Biochemical and Biophysical Research Communications, pp. 892–901.

"Human CSF-1: Molecular Cloning and Expression . . . Urinary Protein", by G. Wong et al., vol. 235, Mar. 20, 1987, Science, pp. 1504–1508.

Jour. of Bacteriology, Aug. 1980, pp. 971–980, vol. 143, No. 2, "In Vitro Gene Fusions that join an Enzymatically Active β–Galactosidase Segment to Amino–Terminal Fragments . . . Signals", Casadaban et al.

Science, vol. 220, p. 1053, 3 Jun. 1983, "A Parathyroid Hormone Inhibitor in vivo: Design and Biological Evaluation of a Hormone Analog", Horiuchi et al.

Biochem. & Biophys. Res. Comm., vol. 182, No. 1, 1992, pp. 70–77, "A Heterozygous Mutation (the Codon for Ser $^{447}$→a Stop Codon) in Lipoprotein Lipase Contributes . . . Hyperlipidemia", Kobayashi et al.

Peptides:Chemistry and Biology "Naturally Occurring Active Peptides from Anterior Pituitary and Gonads", Choh Hao Li, 6th Pierce Award Lecture, pp. 3–12, 1988.

Biochem. J. (1989) 259, 665–671, "A Key Functional Role for the Insulin–Like Growth Factor I N–Terminal Pentapeptide", Bagley et al.

Proc. Natl. Acad. Sci., vol. 86, pp. 3992–3996, Jun. 1989, "A Five–Residue Sequence Near the Carboxyl terminus of the Polytopic Membrane Protein Lac Permease . . . within the Membrane", Roepe et al.

The Jour. of Biological Chem., vol. 264, No. 21, pp. 12179–12186, 1989, "Amino Terminus is essential to the Structural Integrity of Recombinant Human Interferon–γ", Hogrefe et al.

Protein Engineering, vol. 4, No. 3, pp. 335–341, 1991, "The Carboxyl–Terminal Region of Human Interferon γ is Important for Biological Activity: Mutagenic and NMR Analysis", Lundell et al.

Protein Engineering, vol. 4, No. 4, pp. 385–389, 1991, "Structural and Functional Domains in Human Tumor Necrosis Factors", Cynthia R. Goh and Alan G. Porter.

The Jour. of Biological Chem., vol. 262, No. 12, pp. 5723–5731, 1987, "Structure–Function Analysis of Human Interleukin–2", Grace Ju et al.

J. Biochem., vol. 104, No. 5, 837–840, 1988, "Site–Specific Mutagenesis of the Human Interleukin–1β Gene: The Role of Arginine Residue at the N–Terminal Region", Kamogashira et al.

Schoner et al., PWAS, vol. 81, p. 5403, 1984.

Ghrayeb et al., Embo J., vol. 3, p. 2437, 1984.

Takahashi et al. "Amino–Terminal . . . Of Human M–CSF" BBRC 161, 892 1989.

Cerretti et al., Molecular Immunology 25, 761, 1988 "Human Macrophage–Colony Stimulating Factor: Alternative RNA and Protein Processing From A Single Gene".

(List continued on next page.)

Primary Examiner—Stephen Walsh
Assistant Examiner—Sally P. Teng
Attorney, Agent, or Firm—Sughrue, Mion, Zinn, Macpeak & Seas

[57] ABSTRACT

This invention relates to a biologically active recombinant human M-CSF obtained by expressing a human M-CSF gene coding for the amino acid sequence of the formula (1) in its entirety or devoid of a portion thereof; a process for preparing the recombinant human M-CSF; an expression plasmid containing the human M-CSF gene defined above; and a transformant haboring the above expression plasmid.

4 Claims, 36 Drawing Sheets

OTHER PUBLICATIONS

Cosman et al., Behring Inst. Mitt. 83, 15, 1988 "Human Macrophage Colony Stimulating Factor (M–CSF): Alternate RNA Splicing Generates Three Different Proteins That Are . . .".

Heard et al., Oncogene Res. 1, 324, 1987 "Synthesis, Post–Translational Processing, and Autocrine Transforming Activity of a . . . ".

Rehenmier et al, Mol Cell Biol 8(11) 1988, pp. 5026–5034.

Mances, Mol Cell. Biol 8(11) 1988, pp. 5035–5039.

Science, vol. 230, 291–296, Oct. 18, 1985.

Science, vol. 235, 1504–1508, Mar. 20, 1987.

The EMBO Journal, vol. 6, No. 9, 2693–2698, 1987.

Kawasaki, E.S. et al. "Molecular Cloning of a Complementary DNA Encoding Macrophage Specific Colony–Stimulating Factor (CSF–1)", Science, vol. 230, pp. 291–296, 1985.

Saito, Y. et al. "Direct Expression of a Synthetic Somatomedin C Gene in Escherichia coli by Use of a Two–Cistron System", J. Biochem, vol. 101, pp. 1281–1288, 1987.

Ladner, M.B. et al., "Human CSF–1: gene structure and alternative splicing of MRNA precursors," The EMBO Journal, vol. 6, No. 9, pp. 2693–2698, 1987.

FIG. 2-1

```
5' AGCCGCTCTC CGCATCCCAG GACAGCGGTG CGGCCCTCGG CCGGGGCGCC
   TCGGCGAGAG GCGTAGGGTC CTGTCGCCAC GCCGGGAGCC GGCCCCGCGG

CACTCCGCAG CACCCAGCGA GCGAGCGAGC GAGCGAGGGC GGCCGACGCG
   GTGAGGCGTC GTGGGTCGCT CGCTCGCTCG CTCGCTCCCG CCGGCTGCGC

CCCGGCCGGG ACCCAGCTGC CCGTATGACC GCGCCGGGCG CCGCCGGGCG
   GGGCCGGCCC TGGGTCGACG GGCATACTGG CGCGGCCCGC GGCGGCCCGC

CTGCCCTCCC ACGACATGGC TGGGCTCCCT GCTGTTGTTG GTCTGTCTCC
   GACGGGAGGG TGCTGTACCG ACCCGAGGGA CGACAACAAC CAGACAGAGG

TGGCGAGCAG GAGTATCACC GAGGAGGTGT CGGAGTACTG TAGCCACATG
   ACCGCTCGTC CTCATAGTGG CTCCTCCACA GCCTCATGAC ATCGGTGTAC

ATTGGGAGTG GACACCTGCA GTCTCTGCAG CGGCTGATTG ACAGTCAGAT
   TAACCCTCAC CTGTGGACGT CAGAGACGTC GCCGACTAAC TGTCAGTCTA

GGAGACCTCG TGCCAAATTA CATTTGAGTT TGTAGACCAG GAACAGTTGA
   CCTCTGGAGC ACGGTTTAAT GTAAACTCAA ACATCTGGTC CTTGTCAACT

AAGATCCAGT GTGCTACCTT AAGAAGGCAT TTCTCCTGGT ACAATACATA
   TTCTAGGTCA CACGATGGAA TTCTTCCGTA AAGAGGACCA TGTTATGTAT

ATGGAGGACA CCATGCGCTT CAGAGATAAC ACCCCCAATG CCATCGCCAT
   TACCTCCTGT GGTACGCGAA GTCTCTATTG TGGGGGTTAC GGTAGCGGTA

TGTGCAGCTG CAGGAACTCT CTTTGAGGCT GAAGAGCTGC TTCACCAAGG
   ACACGTCGAC GTCCTTGAGA GAAACTCCGA CTTCTCGACG AAGTGGTTCC

ATTATGAAGA GCATGACAAG GCCTGCGTCC GAACTTTCTA TGAGACACCT
   TAATACTTCT CGTACTGTTC CGGACGCAGG CTTGAAAGAT ACTCTGTGGA

CTCCAGTTGC TGGAGAAGGT CAAGAATGTC TTTAATGAAA CAAAGAATCT
   GAGGTCAACG ACCTCTTCCA GTTCTTACAG AAATTACTTT GTTTCTTAGA

CCTTGACAAG GACTGGAATA TTTTCAGCAA GAACTGCAAC AACAGCTTTG
   GGAACTGTTC CTGACCTTAT AAAAGTCGTT CTTGACGTTG TTGTCGAAAC

CTGAATGCTC CAGCCAAGAT GTGGTGACCA AGCCTGATTG CAACTGCCTG
   GACTTACGAG GTCGGTTCTA CACCACTGGT TCGGACTAAC GTTGACGGAC

TACCCCAAAG CCATCCCTAG CAGTGACCCG GCCTCTGTCT CCCCTCATCA
   ATGGGGTTTC GGTAGGGATC GTCACTGGGC CGGAGACAGA GGGGAGTAGT
```

FIG. 2-2

```
GCCCCTCGCC CCCTCCATGG CCCCTGTGGC TGGCTTGACC TGGGAGGACT
CGGGGAGCGG GGGAGGTACC GGGGACACCG ACCGAACTGG ACCTCCTGA

CTGAGGGAAC TGAGGGCAGC TCCCTCTTGC CTGGTGAGCA GCCCCTGCAC
GACTCCCTTG ACTCCCGTCG AGGGAGAACG GACCACTCGT CGGGGACGTG

ACAGTGGATC CAGGCAGTGC CAAGCAGCGG CCACCCAGGA GCACCTGCCA
TGTCACCTAG GTCCGTCACG GTTCGTCGCC GGTGGGTCCT CGTGGACGGT

GAGCTTTGAG CCGCCAGAGA CCCCAGTTGT CAAGGACAGC ACCATCGGTG
CTCGAAACTC GGCGGTCTCT GGGGTCAACA GTTCCTGTCG TGGTAGCCAC

GCTCACCACA GCCTCGCCCC TCTGTCGGGG CCTTCAACCC CGGGATGGAG
CGAGTGGTGT CGGAGCGGGG AGACAGCCCC GGAAGTTGGG GCCCTACCTC

GATATTCTTG ACTCTGCAAT GGGCACTAAT TGGGTCCCAG AAGAAGCCTC
CTATAAGAAC TGAGACGTTA CCCGTGATTA ACCCAGGGTC TTCTTCGGAG

TGGAGAGGCC AGTGAGATTC CCGTACCCCA AGGGACAGAG CTTTCCCCCT
ACCTCTCCGG TCACTCTAAG GGCATGGGGT TCCCTGTCTC GAAAGGGGA

CCAGGCCAGG AGGGGGCAGC ATGCAGACAG AGCCCGCCAG ACCCAGCAAC
GGTCCGGTCC TCCCCCGTCG TACGTCTGTC TCGGGCGGTC TGGGTCGTTG

TTCCTCTCAG CATCTTCTCC ACTCCCTGCA TCAGCAAAGG GCCAACAGCC
AAGGAGAGTC GTAGAAGAGG TGAGGGACGT AGTCGTTTCC CGGTTGTCGG

GGCAGATGTA ACTGGTACCG CCTTGCCCAG GGTGGGCCCG TGAGCATGGC
CCGTCTACAT TGACCATGGC GGAACGGGTC CCACCCGGGC ACTCGTACCG

CAGGACTGGA ATCACACCCC CCAGAAGAGA CACCATCCAT CTGCCCTGCT
GTCCTGACCT TAGTGTGGGG GGTCTTCTCT GTGGTAGGTA GACGGGACGA

CAGAGACCCC CCGGAGCCAG GCTCTCCCAG GATCTCATCA CCGCGCCCCC
GTCTCTGGGG GGCCTCGGTC CGAGAGGGTC CTAGAGTAGT GGCGCGGGGG

AGGGCCTCAG CAACCCCTCC ACCCTCTGCT GCTCAGCCAC AGCTTTCCAG
TCCCGGAGTC GTTGGGAGG TGGGAGACGA CGAGTCGGTG TCGAAAGGTC

AAGCCACTCC TCGGGCGTGC TGCCCTTGGG GAGCTGGAGG GCAGGAGGAG
TTCGGTGAGG AGCCCGCACG ACGGGAACCC CTCGACCTCC CGTCCTCCTC

CACCAGGGAT CGGAGGAGCC CCGCAGAGCC AGAAGGAGGA CCAGCAAGTG
GTGGTCCCTA GCCTCCTCGG GGCGTCTCGG TCTTCCTCCT GGTCGTTCAC
```

FIG. 2-3

```
AAGGCAGCCA GCCCCTGCCC CGTTTTAACT CCGTTCCTTT GACTGACACA
TTCCGTCGGT CGGGGACGGG GCAAAATTGA GGCAAGGAAA CTGACTGTGT

GGCCATGAGA GGCAGTCCGA GGGATCCTCC AGCCCGCAGC TCCAGGAGTC
CCGGTACTCT CCGTCAGGCT CCCTAGGAGG TCGGGCGTCG AGGTCCTCAG

TGTCTTCCAC CTGCTGGTGC CCAGTGTCAT CCTGGTCTTG CTGGCCGTCG
ACAGAAGGTG GACGACCACG GGTCACAGTA GGACCAGAAC GACCGGCAGC

GAGGCCTCTT GTTCTACAGG TGGAGGCGGC GGAGCCATCA AGAGCCTCAG
CTCCGGAGAA CAAGATGTCC ACCTCCGCCG CCTCGGTAGT TCTCGGAGTC

AGAGCGGATT CTCCCTTGGA GCAACCAGAG GGCAGCCCCC TCACTCAGGA
TCTCGCCTAA GAGGGAACCT CGTTGGTCTC CCGTCGGGG AGTGAGTCCT

TGACAGACAG GTGGAACTGC CAGTGTAGAG GGAATTCTAA GACCCCTCAC
ACTGTCTGTC CACCTTGACG GTCACATCTC CCTTAAGATT CTGGGGAGTG

CATCCTGGAC ACTCTCGTTT GTCAATGTCC CTCTGAAAAT GTGACGCCCA
GTAGGACCTG TGAGAGCAAA CAGTTACAGG GAGACTTTTA CACTGCGGGT

GCCCCGGACA CAGTACTCCA GATGTTGTCT GACCAGCTCA GAGAGAGTAC
CGGGGCCTGT GTCATGAGGT CTACAACAGA CTGGTCGAGT CTCTCTCATG

AGTGGGACTG TTACCTTCCT TGATATGGAC AGTATTCTTC TATTTGTGCA
TCACCCTGAC AATGGAAGGA ACTATACCTG TCATAAGAAG ATAAACACGT

GATTAAGATT GCATTAGTTT TTTTCTTAAC AACTGCATCA TACTGTTGTC
CTAATTCTAA CGTAATCAAA AAAAGAATTG TTGACGTAGT ATGACAACAG

ATATGTTGAG CCTGTGGTCT ATAAACCCC TAGTTCCATT TCCCATAAAC
TATACAACTC GGACACCAGA TATTTGGGG ATCAAGGTAA AGGGTATTTG

TTCTGTCAAG CCAGACCATC TCTACCCTGT ACTTGGACAA CTTAACTTTT
AAGACAGTTC GGTCTGGTAG AGATGGGACA TGAACCTGTT GAATTGAAAA

TTAACCAAAG TGCAGTTTAT GTTCACCTTT GTTAAAGCCA CCTTGTGGTT
AATTGGTTTC ACGTCAAATA CAAGTGGAAA CAATTTCGGT GGAACACCAA

TCTGCCCATC ACCTGAACCT ACTGAAGTTG TGTGAAATCC TAATTCTGTC
AGACGGGTAG TGGACTTGGA TGACTTCAAC ACACTTTAGG ATTAAGACAG

ATCTCCGTAG CCCTCCCAGT TGTGCCTCCT GCACATTGAT GAGTGCCTGC
TAGAGGCATC GGGAGGGTCA ACACGGAGGA CGTGTAACTA CTCACGGACG
```

FIG. 2-4

```
TGTTGTCTTT GCCCATGTTG TTGATGTAGC TGTGACCCTA TTGTTCCTCA
ACAACAGAAA CGGGTACAAC AACTACATCG ACACTGGGAT AACAAGGAGT

CCCCTGCCCC CCGCCAACCC CAGCTGGCCC ACCTCTTCCC CCTCCCACCC
GGGGACGGGG GGCGGTTGGG GTCGACCGGG TGGAGAAGGG GGAGGGTGGG

AAGCCCACAG CCAGCCCATC AGGAAGCCTT CCTGGCTTCT CCACAACCTT
TTCGGGTGTC GGTCGGGTAG TCCTTCGGAA GGACCGAAGA GGTGTTGGAA

CTGACTGTCT TTTCAGTCAT GCCCCTGCT CTTTTGTATT TGGCTAATAG
GACTGACAGA AAAGTCAGTA CGGGGACGA GAAAACATAA ACCGATTATC

TATATCAATT TGCACTTAAA AAAAAAAAAA AAAAAAAA 3'
ATATAGTTAA ACGTGAATTT TTTTTTTTTT TTTTTTTT
```

FIG. 3-1

```
ATG.ACC.GCG.CCG.GGC.GCC.GCC.GGG.CGC.TGC.CCT.CCC.ACG.ACA.TGG.
Met-Thr-Ala-Pro-Gly-Ala-Ala-Gly-Arg-Cys-Pro-Pro-Thr-Thr-Trp-

CTG.GGC.TCC.CTG.CTG.TTG.TTG.GTC.TGT.CTC.CTG.GCG.AGC.AGG.AGT.
Leu-Gly-Ser-Leu-Leu-Leu-Leu-Val-Cys-Leu-Leu-Ala-Ser-Arg-Ser-

ATC.ACC.GAG.GAG.GTG.TCG.GAG.TAC.TGT.AGC.CAC.ATG.ATT.GGG.AGT.
Ile-Thr-Glu-Glu-Val-Ser-Glu-Tyr-Cys-Ser-His-Met-Ile-Gly-Ser-

GGA.CAC.CTG.CAG.TCT.CTG.CAG.CGG.CTG.ATT.GAC.AGT.CAG.ATG.GAG.
Gly-His-Leu-Gln-Ser-Leu-Gln-Arg-Leu-Ile-Asp-Ser-Gln-Met-Glu-

ACC.TCG.TGC.CAA.ATT.ACA.TTT.GAG.TTT.GTA.GAC.CAG.GAA.CAG.TTG.
Thr-Ser-Cys-Gln-Ile-Thr-Phe-Glu-Phe-Val-Asp-Gln-Glu-Gln-Leu-

AAA.GAT.CCA.GTG.TGC.TAC.CTT.AAG.AAG.GCA.TTT.CTC.CTG.GTA.CAA.
Lys-Asp-Pro-Val-Cys-Tyr-Leu-Lys-Lys-Ala-Phe-Leu-Leu-Val-Gln-

TAC.ATA.ATG.GAG.GAC.ACC.ATG.CGC.TTC.AGA.GAT.AAC.ACC.CCC.AAT.
Tyr-Ile-Met-Glu-Asp-Thr-Met-Arg-Phe-Arg-Asp-Asn-Thr-Pro-Asn-

GCC.ATC.GCC.ATT.GTG.CAG.CTG.CAG.GAA.CTC.TCT.TTG.AGG.CTG.AAG
Ala-Ile-Ala-Ile-Val-Gln-Leu-Gln-Glu-Leu-Ser-Leu-Arg-Leu-Lys

AGC.TGC.TTC.ACC.AAG.GAT.TAT.GAA.GAG.CAT.GAC.AAG.GCC.TGC.GTC.
Ser-Cys-Phe-Thr-Lys-Asp-Tyr-Glu-Glu-His-Asp-Lys-Ala-Cys-Val-

CGA.ACT.TTC.TAT.GAG.ACA.CCT.CTC.CAG.TTG.CTG.GAG.AAG.GTC.AAG.
Arg-Thr-Phe-Tyr-Glu-Thr-Pro-Leu-Gln-Leu-Leu-Glu-Lys-Val-Lys-

AAT.GTC.TTT.AAT.GAA.ACA.AAG.AAT.CTC.CTT.GAC.AAG.GAC.TGG.AAT.
Asn-Val-Phe-Asn-Glu-Thr-Lys-Asn-Leu-Leu-Asp-Lys-Asp-Trp-Asn-

ATT.TTC.AGC.AAG.AAC.TGC.AAC.AAC.AGC.TTT.GCT.GAA.TGC.TCC.AGC.
Ile-Phe-Ser-Lys-Asn-Cys-Asn-Asn-Ser-Phe-Ala-Glu-Cys-Ser-Ser-

CAA.GAT.GTG.GTG.ACC.AAG.CCT.GAT.TGC.AAC.TGC.CTG.TAC.CCC.AAA.
Gln-Asp-Val-Val-Thr-Lys-Pro-Asp-Cys-Asn-Cys-Leu-Tyr-Pro-Lys-

GCC.ATC.CCT.AGC.AGT.GAC.CCG.GCC.TCT.GTC.TCC.CCT.CAT.CAG.CCC.
Ala-Ile-Pro-Ser-Ser-Asp-Pro-Ala-Ser-Val-Ser-Pro-His-Gln-Pro-

CTC.GCC.CCC.TCC.ATG.GCC.CCT.GTG.GCT.GGC.TTG.ACC.TGG.GAG.GAC.
Leu-Ala-Pro-Ser-Met-Ala-Pro-Val-Ala-Gly-Leu-Thr-Trp-Glu-Asp-
```

FIG. 3-2

```
TCT.GAG.GGA.ACT.GAG.GGC.AGC.TCC.CTC.TTG.CCT.GGT.GAG.CAG.CCC.
Ser-Glu-Gly-Thr-Glu-Gly-Ser-Ser-Leu-Leu-Pro-Gly-Glu-Gln-Pro-

CTG.CAC.ACA.GTG.GAT.CCA.GGC.AGT.GCC.AAG.CAG.CGG.CCA.CCC.AGG.
Leu-His-Thr-Val-Asp-Pro-Gly-Ser-Ala-Lys-Gln-Arg-Pro-Pro-Arg-

AGC.ACC.TGC.CAG.AGC.TTT.GAG.CCG.CCA.GAG.ACC.CCA.GTT.GTC.AAG.
Ser-Thr-Cys-Gln-Ser-Phe-Glu-Pro-Pro-Glu-Thr-Pro-Val-Val-Lys-

GAC.AGC.ACC.ATC.GGT.GGC.TCA.CCA.CAG.CCT.CGC.CCC.TCT.GTC.GGG.
Asp-Ser-Thr-Ile-Gly-Gly-Ser-Pro-Gln-Pro-Arg-Pro-Ser-Val-Gly-

GCC.TTC.AAC.CCC.GGG.ATG.GAG.GAT.ATT.CTT.GAC.TCT.GCA.ATG.GGC.
Ala-Phe-Asn-Pro-Gly-Met-Glu-Asp-Ile-Leu-Asp-Ser-Ala-Met-Gly-

ACT.AAT.TGG.GTC.CCA.GAA.GAA.GCC.TCT.GGA.GAG.GCC.AGT.GAG.ATT.
Thr-Asn-Trp-Val-Pro-Glu-Glu-Ala-Ser-Gly-Glu-Ala-Ser-Glu-Ile-

CCC.GTA.CCC.CAA.GGG.ACA.GAG.CTT.TCC.CCC.TCC.AGG.CCA.GGA.GGG.
Pro-Val-Pro-Gln-Gly-Thr-Glu-Leu-Ser-Pro-Ser-Arg-Pro-Gly-Gly-

GGC.AGC.ATG.CAG.ACA.GAG.CCC.GCC.AGA.CCC.AGC.AAC.TTC.CTC.TCA.
Gly-Ser-Met-Gln-Thr-Glu-Pro-Ala-Arg-Pro-Ser-Asn-Phe-Leu-Ser-

GCA.TCT.TCT.CCA.CTC.CCT.GCA.TCA.GCA.AAG.GGC.CAA.CAG.CCG.GCA.
Ala-Ser-Ser-Pro-Leu-Pro-Ala-Ser-Ala-Lys-Gly-Gln-Gln-Pro-Ala-

GAT.GTA.ACT.GGT.ACC.GCC.TTG.CCC.AGG.GTG.GGC.CCG.TGA.
Asp-Val-Thr-Gly-Thr-Ala-Leu-Pro-Arg-Val-Gly-Pro-***-
```

FIG. 4-1

```
5' AGCCGCTCTC CGCATCCCAG GACAGCGGTG CGGCCCTCGG CCGGGGCGCC
   TCGGCGAGAG GCGTAGGGTC CTGTCGCCAC GCCGGGAGCC GGCCCCGCGG

CACTCCGCAG CACCCAGCGA GCGAGCGAGC GAGCGAGGGC GGCCGACGCG
   GTGAGGCGTC GTGGGTCGCT CGCTCGCTCG CTCGCTCCCG CCGGCTGCGC

CCCGGCCGGG ACCCAGCTGC CCGTATGACC GCGCCGGGCG CCGCCGGGCG
   GGGCCGGCCC TGGGTCGACG GGCATACTGG CGCGGCCCGC GGCGGCCCGC

CTGCCCTCCC ACGACATGGC TGGGCTCCCT GCTGTTGTTG GTCTGTCTCC
   GACGGGAGGG TGCTGTACCG ACCCGAGGGA CGACAACAAC CAGACAGAGG

TGGCGAGCAG GAGTATCACC GAGGAGGTGT CGGAGTACTG TAGCCACATG
   ACCGCTCGTC CTCATAGTGG CTCCTCCACA GCCTCATGAC ATCGGTGTAC

ATTGGGAGTG GACACCTGCA GTCTCTGCAG CGGCTGATTG ACAGTCAGAT
   TAACCCTCAC CTGTGGACGT CAGAGACGTC GCCGACTAAC TGTCAGTCTA

GGAGACCTCG TGCCAAATTA CATTTGAGTT TGTAGACCAG GAACAGTTGA
   CCTCTGGAGC ACGGTTTAAT GTAAACTCAA ACATCTGGTC CTTGTCAACT

AAGATCCAGT GTGCTACCTT AAGAAGGCAT TTCTCCTGGT ACAAGACATA
   TTCTAGGTCA CACGATGGAA TTCTTCCGTA AAGAGGACCA TGTTCTGTAT

ATGGAGGACA CCATGCGCTT CAGAGATAAC ACCCCCAATG CCATCGCCAT
   TACCTCCTGT GGTACGCGAA GTCTCTATTG TGGGGGTTAC GGTAGCGGTA

TGTGCAGCTG CAGGAACTCT CTTTGAGGCT GAAGAGCTGC TTCACCAAGG
   ACACGTCGAC GTCCTTGAGA GAAACTCCGA CTTCTCGACG AAGTGGTTCC

ATTATGAAGA GCATGACAAG GCCTGCGTCC GAACTTTCTA TGAGACACCT
   TAATACTTCT CGTACTGTTC CGGACGCAGG CTTGAAAGAT ACTCTGTGGA

CTCCAGTTGC TGGAGAAGGT CAAGAATGTC TTTAATGAAA CAAAGAATCT
   GAGGTCAACG ACCTCTTCCA GTTCTTACAG AAATTACTTT GTTTCTTAGA

CCTTGACAAG GACTGGAATA TTTTCAGCAA GAACTGCAAC AACAGCTTTG
   GGAACTGTTC CTGACCTTAT AAAAGTCGTT CTTGACGTTG TTGTCGAAAC

CTGAATGCTC CAGCCAAGAT GTGGTGACCA AGCCTGATTG CAACTGCCTG
   GACTTACGAG GTCGGTTCTA CACCACTGGT TCGGACTAAC GTTGACGGAC

TACCCCAAAG CCATCCCTAG CAGTGACCCG GCCTCTGTCT CCCCTCATCA
   ATGGGGTTTC GGTAGGGATC GTCACTGGGC CGGAGACAGA GGGGAGTAGT
```

FIG. 4-2

```
GCCCCTCGCC CCCTCCATGG CCCCTGTGGC TGGCTTGACC TGGGAGGACT
CGGGGAGCGG GGGAGGTACC GGGGACACCG ACCGAACTGG ACCCTCCTGA

CTGAGGGAAC TGAGGGCAGC TCCCTCTTGC CTGGTGAGCA GCCCCTGCAC
GACTCCCTTG ACTCCCGTCG AGGGAGAACG GACCACTCGT CGGGGACGTG

ACAGTGGATC CAGGCAGTGC CAAGCAGCGG CCACCCAGGA GCACCTGCCA
TGTCACCTAG GTCCGTCACG GTTCGTCGCC GGTGGGTCCT CGTGGACGGT

GAGCTTTGAG CCGCCAGAGA CCCCAGTTGT CAAGGACAGC ACCATCGGTG
CTCGAAACTC GGCGGTCTCT GGGGTCAACA GTTCCTGTCG TGGTAGCCAC

GCTCACCACA GCCTCGCCCC TCTGTCGGGG CCTTCAACCC CGGGATGGAG
CGAGTGGTGT CGGAGCGGGG AGACAGCCCC GGAAGTTGGG GCCCTACCTC

GATATTCTTG ACTCTGCAAT GGGCACTAAT TGGGTCCCAG AAGAAGCCTC
CTATAAGAAC TGAGACGTTA CCCGTGATTA ACCCAGGGTC TTCTTCGGAG

TGGAGAGGCC AGTGAGATTC CCGTACCCCA AGGGACAGAG CTTTCCCCCT
ACCTCTCCGG TCACTCTAAG GGCATGGGGT TCCCTGTCTC GAAAGGGGA

CCAGGCCAGG AGGGGCAGC ATGCAGACAG AGCCCGCCAG ACCCAGCAAC
GGTCCGGTCC TCCCCCGTCG TACGTCTGTC TCGGGCGGTC TGGGTCGTTG

TTCCTCTCAG CATCTTCTCC ACTCCCTGCA TCAGCAAAGG GCCAACAGCC
AAGGAGAGTC GTAGAAGAGG TGAGGGACGT AGTCGTTTCC CGGTTGTCGG

GGCAGATGTA ACTGGTACCG CCTTGCCCAG GGTGGGCCCG GTGAGGCCCA
CCGTCTACAT TGACCATGGC GGAACGGGTC CCACCCGGGC CACTCCGGGT

CTGGCCAGGA CTGGAATCAC ACCCCCCAGA AGACAGACCA TCCATCTGCC
GACCGGTCCT GACCTTAGTG TGGGGGGTCT TCTGTCTGGT AGGTAGACGG

CTGCTCAGAG ACCCCCCGGA GCCAGGCTCT CCCAGGATCT CATCACCGCG
GACGAGTCTC TGGGGGGCCT CGGTCCGAGA GGGTCCTAGA GTAGTGGCGC

CCCCCAGGGC CTCAGCAACC CCTCCACCCT CTCTGCTCAG CCACAGCTTT
GGGGGTCCCG GAGTCGTTGG GGAGGTGGGA GAGACGAGTC GGTGTCGAAA

CCAGAAGCCA CTCCTCGGGC AGCGTGCTGC CCCTTGGGGA GCTGGAGGGC
GGTCTTCGGT GAGGAGCCCG TCGCACGACG GGGAACCCCT CGACCTCCCG

AGGAGGAGCA CCAGGGATCG GAGGAGCCCC GCAGAGCCAG AAGGAGGACC
TCCTCCTCGT GGTCCCTAGC CTCCTCGGGG CGTCTCGGTC TTCCTCCTGG
```

FIG. 4-3

```
AGCAAGTGAA GGGGCAGCCA GGCCCCTGCC CCGTTTTAAC TCCGTTCCTT
TCGTTCACTT CCCCGTCGGT CCGGGGACGG GGCAAAATTG AGGCAAGGAA

TGACTGACAC AGGCCATGAG AGGCAGTCCG AGGGATCCTC CAGCCCGCAG
ACTGACTGTG TCCGGTACTC TCCGTCAGGC TCCCTAGGAG GTCGGGCGTC

CTCCAGGAGT CTGTCTTCCA CCTGCTGGTG CCCAGTGTCA TCCTGGTCTT
GAGGTCCTCA GACAGAAGGT GGACGACCAC GGGTCACAGT AGGACCAGAA

GCTGGCCGTC GGAGGCCTCT TGTTCTACAG GTGGAGGCGG CGGAGCCATC
CGACCGGCAG CCTCCGGAGA ACAAGATGTC CACCTCCGCC GCCTCGGTAG

AAGAGCCTCA GAGAGCGGAT TCTCCCTTGG AGCAACCAGA GGGCAGCCCC
TTCTCGGAGT CTCTCGCCTA AGAGGGAACC TCGTTGGTCT CCCGTCGGGG

CTCACTCAGG ATGACAGACA GGTGGAACTG CCAGTGTAGA GGGAATTCTA
GAGTGAGTCC TACTGTCTGT CCACCTTGAC GGTCACATCT CCCTTAAGAT

AGACCCCTCA CCATCCTGGA CACTCTCGTT TGTCAATGTC CCTCTGAAAA
TCTGGGGAGT GGTAGGACCT GTGAGACCAA ACAGTTACAG GGAGACTTTT

TGTGACGCCC AGCCCCGGAC ACAGTACTCC AGATGTTGTC TGACCAGCTC
ACACTGCGGG TCGGGCCTG TGTCATGAGG TCTACAACAG ACTGGTCGAG

AGAGAGAGTA CAGTGGGACT GTTACCTTCC TTGATATGGA CAGTATTCTT
TCTCTCTCAT GTCACCCTGA CAATGGAAGG AACTATACCT GTCATAAGAA

CTATTTGTGC AGATTAAGAT TGCATTAGTT TTTTTCTTAA CAACTGCATC
GATAAACACG TCTAATTCTA ACGTAATCAA AAAAAGAATT GTTGACGTAG

ATACTGTTGT CATATGTTGA GCCTGTGGTC TATAAACCC CTAGTTCCAT
TATGACAACA GTATACAACT CGGACACCAG ATATTTGGG GATCAAGGTA

TTCCCATAAA CTTCTGTCAA GCCAGACCAT CTCTACCCTG TACTTGGACA
AAGGGTATTT GAAGACAGTT CGGTCTGGTA GAGATGGGAC ATGAACCTGT

ACTTAACTTT TTTAACCAAA GTGCAGTTTA TGTTCACCTT TGTTAAAGCC
TGAATTGAAA AAATTGGTTT CACGTCAAAT ACAAGTGGAA ACAATTTCGG

ACCTTGTGGT TTCTGCCCAT CACCTGAACC TACTGAAGTT GTGTGAAATC
TGGAACACCA AAGACGGGTA GTGGACTTGG ATGACTTCAA CACACTTTAG

CTAATTCTGT CATCTCCGTA GCCCTCCCAG TTGTGCCTCC TGCACATTGA
GATTAAGACA GTAGAGGCAT CGGGAGGGTC AACACGGAGG ACGTGTAACT
```

FIG. 4-4

```
TGAGTGCCTG CTGTTGTCTT TGCCCATGTT GTTGATGTAG CTGTGACCCT
ACTCACGGAC GACAACAGAA ACGGGTACAA CAACTACATC GACACTGGGA

ATTGTTCCTC ACCCCTGCCC CCCGCCAACC CCAGCTGGCC CACCTCTTCC
TAACAAGGAG TGGGGACGGG GGGCGGTTGG GGTCGACCGG GTGGAGAAGG

CCCTCCCACC CAAGCCCACA GCCAGCCCAT CAGGAAGCCT TCCTGGCTTC
GGGAGGGTGG GTTCGGGTGT CGGTCGGGTA GTCCTTCGGA AGGACCGAAG

TCCACAACCT TCTGACTGTC TTTTCAGTCA TGCCCCCTGC TCTTTTGTAT
AGGTGTTGGA AGACTGACAG AAAAGTCAGT ACGGGGACG AGAAAACATA

TTGGCTAATA GTATATCAAT TTGCACTTAA AAAAAAAAAA AAAAAAAAAA 3'
AACCGATTAT CATATAGTTA AACGTGAATT TTTTTTTTTT TTTTTTTTTT
```

FIG. 5-1

ATG.ACC.GCG.CCG.GGC.GCC.GCC.GGG.CGC.TGC.CCT.CCC.ACG.ACA.TGG.
Met-Thr-Ala-Pro-Gly-Ala-Ala-Gly-Arg-Cys-Pro-Pro-Thr-Thr-Trp-

CTG.GGC.TCC.CTG.CTG.TTG.TTG.GTC.TGT.CTC.CTG.GCG.AGC.AGG.AGT.
Leu-Gly-Ser-Leu-Leu-Leu-Leu-Val-Cys-Leu-Leu-Ala-Ser-Arg-Ser-

ATC.ACC.GAG.GAG.GTG.TCG.GAG.TAC.TGT.AGC.CAC.ATG.ATT.GGG.AGT.
Ile-Thr-Glu-Glu-Val-Ser-Glu-Tyr-Cys-Ser-His-Met-Ile-Gly-Ser-

GGA.CAC.CTG.CAG.TCT.CTG.CAG.CGG.CTG.ATT.GAC.AGT.CAG.ATG.GAG.
Gly-His-Leu-Gln-Ser-Leu-Gln-Arg-Leu-Ile-Asp-Ser-Gln-Met-Glu-

ACC.TCG.TGC.CAA.ATT.ACA.TTT.GAG.TTT.GTA.GAC.CAG.GAA.CAG.TTG.
Thr-Ser-Cys-Gln-Ile-Thr-Phe-Glu-Phe-Val-Asp-Gln-Glu-Gln-Leu-

AAA.GAT.CCA.GTG.TGC.TAC.CTT.AAG.AAG.GCA.TTT.CTC.CTG.GTA.CAA.
Lys-Asp-Pro-Val-Cys-Tyr-Leu-Lys-Lys-Ala-Phe-Leu-Leu-Val-Gln-

GAC.ATA.ATG.GAG.GAC.ACC.ATG.CGC.TTC.AGA.GAT.AAC.ACC.CCC.AAT.
Asp-Ile-Met-Glu-Asp-Thr-Met-Arg-Phe-Arg-Asp-Asn-Thr-Pro-Asn-

GCC.ATC.GCC.ATT.GTG.CAG.CTG.CAG.GAA.CTC.TCT.TTG.AGG.CTG.AAG.
Ala-Ile-Ala-Ile-Val-Gln-Leu-Gln-Glu-Leu-Ser-Leu-Arg-Leu-Lys

AGC.TGC.TTC.ACC.AAG.GAT.TAT.GAA.GAG.CAT.GAC.AAG.GCC.TGC.GTC.
Ser-Cys-Phe-Thr-Lys-Asp-Tyr-Glu-Glu-His-Asp-Lys-Ala-Cys-Val-

CGA.ACT.TTC.TAT.GAG.ACA.CCT.CTC.CAG.TTG.CTG.GAG.AAG.GTC.AAG.
Arg-Thr-Phe-Tyr-Glu-Thr-Pro-Leu-Gln-Leu-Leu-Glu-Lys-Val-Lys-

AAT.GTC.TTT.AAT.GAA.ACA.AAG.AAT.CTC.CTT.GAC.AAG.GAC.TGG.AAT.
Asn-Val-Phe-Asn-Glu-Thr-Lys-Asn-Leu-Leu-Asp-Lys-Asp-Trp-Asn-

ATT.TTC.AGC.AAG.AAC.TGC.AAC.AAC.AGC.TTT.GCT.GAA.TGC.TCC.AGC.
Ile-Phe-Ser-Lys-Asn-Cys-Asn-Asn-Ser-Phe-Ala-Glu-Cys-Ser-Ser-

CAA.GAT.GTG.GTG.ACC.AAG.CCT.GAT.TGC.AAC.TGC.CTG.TAC.CCC.AAA.
Gln-Asp-Val-Val-Thr-Lys-Pro-Asp-Cys-Asn-Cys-Leu-Tyr-Pro-Lys-

GCC.ATC.CCT.AGC.AGT.GAC.CCG.GCC.TCT.GTC.TCC.CCT.CAT.CAG.CCC.
Ala-Ile-Pro-Ser-Ser-Asp-Pro-Ala-Ser-Val-Ser-Pro-His-Gln-Pro-

CTC.GCC.CCC.TCC.ATG.GCC.CCT.GTG.GCT.GGC.TTG.ACC.TGG.GAG.GAC.
Leu-Ala-Pro-Ser-Met-Ala-Pro-Val-Ala-Gly-Leu-Thr-Trp-Glu-Asp-

FIG. 5-2

TCT.GAG.GGA.ACT.GAG.GGC.AGC.TCC.CTC.TTG.CCT.GGT.GAG.CAG.CCC.
Ser-Glu-Gly-Thr-Glu-Gly-Ser-Ser-Leu-Leu-Pro-Gly-Glu-Gln-Pro-

CTG.CAC.ACA.GTG.GAT.CCA.GGC.AGT.GCC.AAG.CAG.CGG.CCA.CCC.AGG.
Leu-His-Thr-Val-Asp-Pro-Gly-Ser-Ala-Lys-Gln-Arg-Pro-Pro-Arg-

AGC.ACC.TGC.CAG.AGC.TTT.GAG.CCG.CCA.GAG.ACC.CCA.GTT.GTC.AAG.
Ser-Thr-Cys-Gln-Ser-Phe-Glu-Pro-Pro-Glu-Thr-Pro-Val-Val-Lys-

GAC.AGC.ACC.ATC.GGT.GGC.TCA.CCA.CAG.CCT.CGC.CCC.TCT.GTC.GGG.
Asp-Ser-Thr-Ile-Gly-Gly-Ser-Pro-Gln-Pro-Arg-Pro-Ser-Val-Gly-

GCC.TTC.AAC.CCC.GGG.ATG.GAG.GAT.ATT.CTT.GAC.TCT.GCA.ATG.GGC.
Ala-Phe-Asn-Pro-Gly-Met-Glu-Asp-Ile-Leu-Asp-Ser-Ala-Met-Gly-

ACT.AAT.TGG.GTC.CCA.GAA.GAA.GCC.TCT.GGA.GAG.GCC.AGT.GAG.ATT.
Thr-Asn-Trp-Val-Pro-Glu-Glu-Ala-Ser-Gly-Glu-Ala-Ser-Glu-Ile-

CCC.GTA.CCC.CAA.GGG.ACA.GAG.CTT.TCC.CCC.TCC.AGG.CCA.GGA.GGG.
Pro-Val-Pro-Gln-Gly-Thr-Glu-Leu-Ser-Pro-Ser-Arg-Pro-Gly-Gly-

GGC.AGC.ATG.CAG.ACA.GAG.CCC.GCC.AGA.CCC.AGC.AAC.TTC.CTC.TCA.
Gly-Ser-Met-Gln-Thr-Glu-Pro-Ala-Arg-Pro-Ser-Asn-Phe-Leu-Ser-

GCA.TCT.TCT.CCA.CTC.CCT.GCA.TCA.GCA.AAG.GGC.CAA.CAG.CCG.GCA.
Ala-Ser-Ser-Pro-Leu-Pro-Ala-Ser-Ala-Lys-Gly-Gln-Gln-Pro-Ala-

GAT.GTA.ACT.GGT.ACC.GCC.TTG.CCC.AGG.GTG.GGC.CCC.GTG.AGG.CCC.
Asp-Val-Thr-Gly-Thr-Ala-Leu-Pro-Arg-Val-Gly-Pro-Val-Arg-Pro-

ACT.GGC.CAG.GAC.TGG.AAT.CAC.ACC.CCC.CAG.AAG.ACA.GAC.CAT.CCA.
Thr-Gly-Gln-Asp-Trp-Asn-His-Thr-Pro-Gln-Lys-Thr-Asp-His-Pro-

TCT.GCC.CTG.CTC.AGA.GAC.CCC.CCG.GAG.CCA.GGC.TCT.CCC.AGG.ATC.
Ser-Ala-Leu-Leu-Arg-Asp-Pro-Pro-Glu-Pro-Gly-Ser-Pro-Arg-Ile-

TCA.TCA.CCG.CGC.CCC.CAG.GGC.CTC.AGC.AAC.CCC.TCC.ACC.CTC.TCT.
Ser-Ser-Pro-Arg-Pro-Gln-Gly-Leu-Ser-Asn-Pro-Ser-Thr-Leu-Ser-

GCT.CAG.CCA.CAG.CTT.TCC.AGA.AGC.CAC.TCC.TCG.GGC.AGC.GTG.CTG.
Ala-Gln-Pro-Gln-Leu-Ser-Arg-Ser-His-Ser-Ser-Gly-Ser-Val-Leu-

CCC.CTT.GGG.GAG.CTG.GAG.GGC.AGG.AGG.AGC.ACC.AGG.GAT.CGG.AGG.
Pro-Leu-Gly-Glu-Leu-Glu-Gly-Arg-Arg-Ser-Thr-Arg-Asp-Arg-Arg-

FIG. 5-3

```
AGC.CCC.GCA.GAG.CCA.GAA.GGA.GGA.CCA.GCA.AGT.GAA.GGG.GCA.GCC.
Ser-Pro-Ala-Glu-Pro-Glu-Gly-Gly-Pro-Ala-Ser-Glu-Gly-Ala-Ala-

AGG.CCC.CTG.CCC.CGT.TTT.AAC.TCC.GTT.CCT.TTG.ACT.GAC.ACA.GGC.
Arg-Pro-Leu-Pro-Arg-Phe-Asn-Ser-Val-Pro-Leu-Thr-Asp-Thr-Gly-

CAT.GAG.AGG.CAG.TCC.GAG.GGA.TCC.TCC.AGC.CCG.CAG.CTC.CAG.GAG.
His-Glu-Arg-Gln-Ser-Glu-Gly-Ser-Ser-Ser-Pro-Gln-Leu-Gln-Glu-

TCT.GTC.TTC.CAC.CTG.CTG.GTG.CCC.AGT.GTC.ATC.CTG.GTC.TTG.CTG.
Ser-Val-Phe-His-Leu-Leu-Val-Pro-Ser-Val-Ile-Leu-Val-Leu-Leu-

GCC.GTC.GGA.GGC.CTC.TTG.TTC.TAC.AGG.TGG.AGG.CGG.CGG.AGC.CAT.
Ala-Val-Gly-Gly-Leu-Leu-Phe-Tyr-Arg-Trp-Arg-Arg-Arg-Ser-His-

CAA.GAG.CCT.CAG.AGA.GCG.GAT.TCT.CCC.TTG.GAG.CAA.CCA.GAG.GGC.
Gln-Glu-Pro-Gln-Arg-Ala-Asp-Ser-Pro-Leu-Glu-Gln-Pro-Glu-Gly-

AGC.CCC.CTC.ACT.CAG.GAT.GAC.AGA.CAG.GTG.GAA.CTG.CCA.GTG.TAG.
Ser-Pro-Leu-Thr-Gln-Asp-Asp-Arg-Gln-Val-Glu-Leu-Pro-Val-***-
```

FIG. 10

Met-Lys-Lys-Thr-Ala-Ile-Ala-Ile-Ala-Val-Ala-Leu-Ala-Gly-Phe-
Ala-Thr-Val-Ala-Gln-Ala-↓Val-Ser-Glu-Tyr-Cys-Ser-His-Met-Ile-
Gly-Ser-Gly-His-Leu-Gln-Ser-Leu-Gln-Arg-Leu-Ile-Asp-Ser-Gln-
Met-Glu-Thr-Ser-Cys-Gln-Ile-Thr-Phe-Glu-Phe-Val-Asp-Gln-Glu-
Gln-Leu-Lys-Asp-Pro-Val-Cys-Tyr-Leu-Lys-Lys-Ala-Phe-Leu-Leu-
Val-Gln-Asp-Ile-Met-Glu-Asp-Thr-Met-Arg-Phe-Arg-Asp-Asn-Thr-
Pro-Asn-Ala-Ile-Ala-Ile-Val-Gln-Leu-Gln-Glu-Leu-Ser-Leu-Arg-
Leu-Lys-Ser-Cys-Phe-Thr-Lys-Asp-Tyr-Glu-Glu-His-Asp-Lys-Ala-
Cys-Val-Arg-Thr-Phe-Tyr-Glu-Thr-Pro-Leu-Gln-Leu-Leu-Glu-Lys-
Val-Lys-Asn-Val-Phe-Asn-Glu-Thr-Lys-Asn-Leu-Leu-Asp-Lys-Asp-
Trp-Asn-Ile-Phe-Ser-Lys-Asn-Cys-Asn-Asn-Ser-Phe-Ala-Glu-Cys-
Ser-Ser-Gln-Asp-Val-Val-Thr

FIG. 11

Met-Lys-Lys-Thr-Ala-Ile-Ala-Ile-Ala-Val-Ala-Leu-Ala-Gly-Phe-
Ala-Thr-Val-Ala-Gln-Ala↓Val-Ser-Glu-Tyr-Cys-Ser-His-Met-Ile-
Gly-Ser-Gly-His-Leu-Gln-Ser-Leu-Gln-Arg-Leu-Ile-Asp-Ser-Gln-
Met-Glu-Thr-Ser-Cys-Gln-Ile-Thr-Phe-Glu-Phe-Val-Asp-Gln-Glu-
Gln-Leu-Lys-Asp-Pro-Val-Cys-Tyr-Leu-Lys-Lys-Ala-Phe-Leu-Leu-
Val-Gln-Asp-Ile-Met-Glu-Asp-Thr-Met-Arg-Phe-Arg-Asp-Asn-Thr-
Pro-Asn-Ala-Ile-Ala-Ile-Val-Gln-Leu-Gln-Glu-Leu-Ser-Leu-Arg-
Leu-Lys-Ser-Cys-Phe-Thr-Lys-Asp-Tyr-Glu-Glu-His-Asp-Lys-Ala-
Cys-Val-Arg-Thr-Phe-Tyr-Glu-Thr-Pro-Leu-Gln-Leu-Leu-Glu-Lys-
Val-Lys-Asn-Val-Phe-Asn-Glu-Thr-Lys-Asn-Leu-Leu-Asp-Lys-Asp-
Trp-Asn-Ile-Phe-Ser-Lys-Asn-Cys-Asn-Asn-Ser-Phe-Ala-Glu-

FIG. 15

ATG.GCA.CCT.
Met-Ala-Pro-
|←

ACT.TCA.AGT.TCT.ACA.AAG.AAA.ACA.CAG.CTA.CAA.CTG.GAG.CAT.TTA.
Thr-Ser-Ser-Ser-Thr-Lys-Lys-Thr-Gln-Leu-Gln-Leu-Glu-His-Leu-
―――― IL-2

CTG.CTG.GAT.TTA.CAG.ATG.ATT.TTG.AAT.GGA.ATT.AAT.AAT.TAC.AAG.
Leu-Leu-Asp-Leu-Gln-Met-Ile-Leu-Asn-Gly-Ile-Asn-Asn-Tyr-Lys-

AAT.CCC.AAA.CTC.ACC.AGG.ATG.CTC.ACA.TTT.AAG.TTT.TAC.ATG.CCC.
Asn-Pro-Lys-Leu-Thr-Arg-Met-Leu-Thr-Phe-Lys-Phe-Tyr-Met-Pro-

AAG.AAG.GCC.ACA.GAA.CTG.AAA.CAT.CTT.CAG.TGT.CTA.GAA.CGG.AGG.
Lys-Lys-Ala-Thr-Glu-Leu-Lys-His-Leu-Gln-Cys-Leu-Glu-Arg-Arg-
                                              IL-2 ――→|

ACT.CAT.TG   ATG GTA.TCA.GAA.TAC.TGT.AGC.CAC.ATG.ATT.GGG.AGT.
Thr-His ter Met-Val-Ser-Glu-Tyr-Cys-Ser-His-Met-Ile-Gly-Ser-
            |←―M-CSF GGA.CAC.CTG.CAG.TCT.CTG.CAG.CGG.CTG.ATT.GAC.AGT.CAG.ATG.GAG.
Gly-His-Leu-Gln-Ser-Leu-Gln-Arg-Leu-Ile-Asp-Ser-Gln-Met-Glu- ACC.TCG.TGC.CAA.ATT.ACA.TTT.GAG.TTT.GTA.GAC.CAG.GAA.CAG.TTG.
Thr-Ser-Cys-Gln-Ile-Thr-Phe-Glu-Phe-Val-Asp-Gln-Glu-Gln-Leu- AAA.GAT.CCA.GTG.TGC.TAC.CTT.AAG.AAG.GCA.TTT.CTC.CTG.GTA.CAA.
Lys-Asp-Pro-Val-Cys-Tyr-Leu-Lys-Lys-Ala-Phe-Leu-Leu-Val-Gln- GAC.ATA.ATG.GAG.GAC.ACC.ATG.CGC.TTC.AGA.GAT.AAC.ACC.CCC.AAT.
Asp-Ile-Met-Glu-Asp-Thr-Met-Arg-Phe-Arg-Asp-Asn-Thr-Pro-Asn- GCC.ATC.GCC.ATT.GTG.CAG.CTG.CAG.GAA.CTC.TCT.TTG.AGG.CTG.AAG.
Ala-Ile-Ala-Ile-Val-Gln-Leu-Gln-Glu-Leu-Ser-Leu-Arg-Leu-Lys AGC.TGC.TTC.ACC.AAG.GAT.TAT.GAA.GAG.CAT.GAC.AAG.GCC.TGC.GTC.
Ser-Cys-Phe-Thr-Lys-Asp-Tyr-Glu-Glu-His-Asp-Lys-Ala-Cys-Val- CGA.ACT.TTC.TAT.GAG.ACA.CCT.CTC.CAG.TTG.CTG.GAG.AAG.GTC.AAG.
Arg-Thr-Phe-Tyr-Glu-Thr-Pro-Leu-Gln-Leu-Leu-Glu-Lys-Val-Lys- AAT.GTC.TTT.AAT.GAA.ACA.AAG.AAT.CTC.CTT.GAC.AAG.GAC.TGG.AAT.
Asn-Val-Phe-Asn-Glu-Thr-Lys-Asn-Leu-Leu-Asp-Lys-Asp-Trp-Asn- ATT.TTC.AGC.AAG.AAC.TGC.AAC.AAC.AGC.TTT.GCT.GAA.TGC.TCC.AGC.
Ile-Phe-Ser-Lys-Asn-Cys-Asn-Asn-Ser-Phe-Ala-Glu-Cys-Ser-Ser- CAA.GAT.GTG.GTG.ACC.TGA.TAA.
Gln-Asp-Val-Val-Thr ter ter
M-CSF ――→|

FIG. 16

```
                                              ATG.GCA.CCT.
                                              Met-Ala-Pro-
                                                 |←
ACT.TCA.AGT.TCT.ACA.AAG.AAA.ACA.CAG.CTA.CAA.CTG.GAG.CAT.TTA.
Thr-Ser-Ser-Ser-Thr-Lys-Lys-Thr-Gln-Leu-Gln-Leu-Glu-His-Leu-
———IL-2
CTG.CTG.GAT.TTA.CAG.ATG.ATT.TTG.AAT.GGA.ATT.AAT.AAT.TAC.AAG.
Leu-Leu-Asp-Leu-Gln-Met-Ile-Leu-Asn-Gly-Ile-Asn-Asn-Tyr-Lys-

AAT.CCC.AAA.CTC.ACC.AGG.ATG.CTC.ACA.TTT.AAG.TTT.TAC.ATG.CCC.
Asn-Pro-Lys-Leu-Thr-Arg-Met-Leu-Thr-Phe-Lys-Phe-Tyr-Met-Pro-

AAG.AAG.GCC.ACA.GAA.CTG.AAA.CAT.CTT.CAG.TGT.CTA.GAA.CGG.AGG.
Lys-Lys-Ala-Thr-Glu-Leu-Lys-His-Leu-Gln-Cys-Leu-Glu-Arg-Arg-
                                      IL-2 ——→|
ACT.TAA.TAA ATG GTA.TCA.GAA.TAC.TGT.AGC.CAC.ATG.ATT.GGG.AGT.
Thr ter ter Met-Val-Ser-Glu-Tyr-Cys-Ser-His-Met-Ile-Gly-Ser-
            |←—M-CSF
GGA.CAC.CTG.CAG.TCT.CTG.CAG.CGG.CTG.ATT.GAC.AGT.CAG.ATG.GAG.
Gly-His-Leu-Gln-Ser-Leu-Gln-Arg-Leu-Ile-Asp-Ser-Gln-Met-Glu- ACC.TCG.TGC.CAA.ATT.ACA.TTT.GAG.TTT.GTA.GAC.CAG.GAA.CAG.TTG.
Thr-Ser-Cys-Gln-Ile-Thr-Phe-Glu-Phe-Val-Asp-Gln-Glu-Gln-Leu- AAA.GAT.CCA.GTG.TGC.TAC.CTT.AAG.AAG.GCA.TTT.CTC.CTG.GTA.CAA.
Lys-Asp-Pro-Val-Cys-Tyr-Leu-Lys-Lys-Ala-Phe-Leu-Leu-Val-Gln- GAC.ATA.ATG.GAG.GAC.ACC.ATG.CGC.TTC.AGA.GAT.AAC.ACC.CCC.AAT.
Asp-Ile-Met-Glu-Asp-Thr-Met-Arg-Phe-Arg-Asp-Asn-Thr-Pro-Asn- GCC.ATC.GCC.ATT.GTG.CAG.CTG.CAG.GAA.CTC.TCT.TTG.AGG.CTG.AAG.
Ala-Ile-Ala-Ile-Val-Gln-Leu-Gln-Glu-Leu-Ser-Leu-Arg-Leu-Lys AGC.TGC.TTC.ACC.AAG.GAT.TAT.GAA.GAG.CAT.GAC.AAG.GCC.TGC.GTC.
Ser-Cys-Phe-Thr-Lys-Asp-Tyr-Glu-Glu-His-Asp-Lys-Ala-Cys-Val- CGA.ACT.TTC.TAT.GAG.ACA.CCT.CTC.CAG.TTG.CTG.GAG.AAG.GTC.AAG.
Arg-Thr-Phe-Tyr-Glu-Thr-Pro-Leu-Gln-Leu-Leu-Glu-Lys-Val-Lys- AAT.GTC.TTT.AAT.GAA.ACA.AAG.AAT.CTC.CTT.GAC.AAG.GAC.TGG.AAT.
Asn-Val-Phe-Asn-Glu-Thr-Lys-Asn-Leu-Leu-Asp-Lys-Asp-Trp-Asn- ATT.TTC.AGC.AAG.AAC.TGC.AAC.AAC.AGC.TTT.GCT.GAA.TGC.TCC.AGC.
Ile-Phe-Ser-Lys-Asn-Cys-Asn-Asn-Ser-Phe-Ala-Glu-Cys-Ser-Ser- CAA.GAT.GTG.GTG.ACC.TGA.TAA.
Gln-Asp-Val-Val-Thr ter ter
              M-CSF ——→|
```

FIG. 17

```
                                    ATG.GCA.CCT.ACT.TCA.
                                    Met-Ala-Pro-Thr-Ser-
                                        |←——IL-2

AGT.TCT.ACA.AAG.AAA.ACA.CAG.CTA.CAA.CTG.GAG.CAT.TTA.CTG.CTG.
Ser-Ser-Thr-Lys-Lys-Thr-Gln-Leu-Gln-Leu-Glu-His-Leu-Leu-Leu-

GAT.TTA.CAG.ATG.ATT.TTG.AAT.GGA.ATT.AAT.AAT.TAC.AAG.AAT.CCC.
Asp-Leu-Gln-Met-Ile-Leu-Asn-Gly-Ile-Asn-Asn-Tyr-Lys-Asn-Pro-

AAA.CTC.ACC.AGG.ATG.CTC.ACA.TTT.AAG.TTT.TAC.ATG.CCC.AAG.AAG.
Lys-Leu-Thr-Arg-Met-Leu-Thr-Phe-Lys-Phe-Tyr-Met-Pro-Lys-Lys-

GCC.ACA.GAA.CTG.AAA.CAT.CTT.CAG.TGT.CTA.GAA.CGG.AGG.ACT.CAT.
Ala-Thr-Glu-Leu-Lys-His-Leu-Gln-Cys-Leu-Glu-Arg-Arg-Thr-His
                                           IL-2 ——→|

TG  ATG.GAA.GAA.GTA.TCA.GAA.TAC.TGT.AGC.CAC.ATG.ATT.GGG.AGT.
ter Met-Glu-Glu-Val-Ser-Glu-Tyr-Cys-Ser-His-Met-Ile-Gly-Ser-
        |←—— M-CSF GGA.CAC.CTG.CAG.TCT.CTG.CAG.CGG.CTG.ATT.GAC.AGT.CAG.ATG.GAG.
Gly-His-Leu-Gln-Ser-Leu-Gln-Arg-Leu-Ile-Asp-Ser-Gln-Met-Glu- ACC.TCG.TGC.CAA.ATT.ACA.TTT.GAG.TTT.GTA.GAC.CAG.GAA.CAG.TTG.
Thr-Ser-Cys-Gln-Ile-Thr-Phe-Glu-Phe-Val-Asp-Gln-Glu-Gln-Leu- AAA.GAT.CCA.GTG.TGC.TAC.CTT.AAG.AAG.GCA.TTT.CTC.CTG.GTA.CAA.
Lys-Asp-Pro-Val-Cys-Tyr-Leu-Lys-Lys-Ala-Phe-Leu-Leu-Val-Gln- GAC.ATA.ATG.GAG.GAC.ACC.ATG.CGC.TTC.AGA.GAT.AAC.ACC.CCC.AAT.
Asp-Ile-Met-Glu-Asp-Thr-Met-Arg-Phe-Arg-Asp-Asn-Thr-Pro-Asn- GCC.ATC.GCC.ATT.GTG.CAG.CTG.CAG.GAA.CTC.TCT.TTG.AGG.CTG.AAG.
Ala-Ile-Ala-Ile-Val-Gln-Leu-Gln-Glu-Leu-Ser-Leu-Arg-Leu-Lys AGC.TGC.TTC.ACC.AAG.GAT.TAT.GAA.GAG.CAT.GAC.AAG.GCC.TGC.GTC.
Ser-Cys-Phe-Thr-Lys-Asp-Tyr-Glu-Glu-His-Asp-Lys-Ala-Cys-Val- CGA.ACT.TTC.TAT.GAG.ACA.CCT.CTC.CAG.TTG.CTG.GAG.AAG.GTC.AAG.
Arg-Thr-Phe-Tyr-Glu-Thr-Pro-Leu-Gln-Leu-Leu-Glu-Lys-Val-Lys- AAT.GTC.TTT.AAT.GAA.ACA.AAG.AAT.CTC.CTT.GAC.AAG.GAC.TGG.AAT.
Asn-Val-Phe-Asn-Glu-Thr-Lys-Asn-Leu-Leu-Asp-Lys-Asp-Trp-Asn- ATT.TTC.AGC.AAG.AAC.TGC.AAC.AAC.AGC.TTT.GCT.GAA.TGC.TCC.AGC.
Ile-Phe-Ser-Lys-Asn-Cys-Asn-Asn-Ser-Phe-Ala-Glu-Cys-Ser-Ser- CAA.GAT.GTG.GTG.ACC.TGA.TAA.
Gln-Asp-Val-Val-Thr ter ter
        M-CSF ——→|
```

FIG. 18

```
                                          ATG.GCA.CCT.
                                          Met-Ala-Pro-
                                          |←─────────
ACT.TCA.AGT.TCT.ACA.AAG.AAA.ACA.CAG.CTA.CAA.CTG.GAG.CAT.TTA.
Thr-Ser-Ser-Thr-Lys-Lys-Thr-Gln-Leu-Gln-Leu-Glu-His-Leu-
── IL-2
CTG.CTG.GAT.TTA.CAG.ATG.ATT.TTG.AAT.GGA.ATT.AAT.AAT.TAC.AAG.
Leu-Leu-Asp-Leu-Gln-Met-Ile-Leu-Asn-Gly-Ile-Asn-Asn-Tyr-Lys-

AAT.CCC.AAA.CTC.ACC.AGG.ATG.CTC.ACA.TTT.AAG.TTT.TAC.ATG.CCC.
Asn-Pro-Lys-Leu-Thr-Arg-Met-Leu-Thr-Phe-Lys-Phe-Tyr-Met-Pro-

AAG.AAG.GCC.ACA.GAA.CTG.AAA.CAT.CTT.CAG.TGT.CTA.GAA.CGG.AGG.
Lys-Lys-Ala-Thr-Glu-Leu-Lys-His-Leu-Gln-Cys-Leu-Glu-Arg-Arg-
                                              IL-2 ──→|
ACT.CAT.TG  ATG GTA.TCA.GAA.TAC.TGT.AGC.CAC.ATG.ATT.GGG.AGT.
Thr-His ter Met-Val-Ser-Glu-Tyr-Cys-Ser-His-Met-Ile-Gly-Ser-
            |←── M-CSF
GGA.CAC.CTG.CAG.TCT.CTG.CAG.CGG.CTG.ATT.GAC.AGT.CAG.ATG.GAG.
Gly-His-Leu-Gln-Ser-Leu-Gln-Arg-Leu-Ile-Asp-Ser-Gln-Met-Glu- ACC.TCG.TGC.CAA.ATT.ACA.TTT.GAG.TTT.GTA.GAC.CAG.GAA.CAG.TTG.
Thr-Ser-Cys-Gln-Ile-Thr-Phe-Glu-Phe-Val-Asp-Gln-Glu-Gln-Leu- AAA.GAT.CCA.GTG.TGC.TAC.CTT.AAG.AAG.GCA.TTT.CTC.CTG.GTA.CAA.
Lys-Asp-Pro-Val-Cys-Tyr-Leu-Lys-Lys-Ala-Phe-Leu-Leu-Val-Gln- TAC.ATA.ATG.GAG.GAC.ACC.ATG.CGC.TTC.AGA.GAT.AAC.ACC.CCC.AAT.
Tyr-Ile-Met-Glu-Asp-Thr-Met-Arg-Phe-Arg-Asp-Asn-Thr-Pro-Asn- GCC.ATC.GCC.ATT.GTG.CAG.CTG.CAG.GAA.CTC.TCT.TTG.AGG.CTG.AAG.
Ala-Ile-Ala-Ile-Val-Gln-Leu-Gln-Glu-Leu-Ser-Leu-Arg-Leu-Lys AGC.TGC.TTC.ACC.AAG.GAT.TAT.GAA.GAG.CAT.GAC.AAG.GCC.TGC.GTC.
Ser-Cys-Phe-Thr-Lys-Asp-Tyr-Glu-Glu-His-Asp-Lys-Ala-Cys-Val- CGA.ACT.TTC.TAT.GAG.ACA.CCT.CTC.CAG.TTG.CTG.GAG.AAG.GTC.AAG.
Arg-Thr-Phe-Tyr-Glu-Thr-Pro-Leu-Gln-Leu-Leu-Glu-Lys-Val-Lys- AAT.GTC.TTT.AAT.GAA.ACA.AAG.AAT.CTC.CTT.GAC.AAG.GAC.TGG.AAT.
Asn-Val-Phe-Asn-Glu-Thr-Lys-Asn-Leu-Leu-Asp-Lys-Asp-Trp-Asn- ATT.TTC.AGC.AAG.AAC.TGC.AAC.AAC.AGC.TTT.GCT.GAA.TGC.TCC.AGC.
Ile-Phe-Ser-Lys-Asn-Cys-Asn-Asn-Ser-Phe-Ala-Glu-Cys-Ser-Ser- CAA.GAT.GTG.GTG.ACC.TGA.TAA.
Gln-Asp-Val-Val-Thr ter ter
           M-CSF ──→|
```

FIG. 19

```
                                                    ATG.GCA.CCT.
                                                    Met-Ala-Pro-
                                                        ⃪
ACT.TCA.AGT.TCT.ACA.AAG.AAA.ACA.CAG.CTA.CAA.CTG.GAG.CAT.TTA.
Thr-Ser-Ser-Ser-Thr-Lys-Lys-Thr-Gln-Leu-Gln-Leu-Glu-His-Leu-
——IL-2
CTG.CTG.GAT.TTA.CAG.ATG.ATT.TTG.AAT.GGA.ATT.AAT.AAT.TAC.AAG.
Leu-Leu-Asp-Leu-Gln-Met-Ile-Leu-Asn-Gly-Ile-Asn-Asn-Tyr-Lys-

AAT.CCC.AAA.CTC.ACC.AGG.ATG.CTC.ACA.TTT.AAG.TTT.TAC.ATG.CCC.
Asn-Pro-Lys-Leu-Thr-Arg-Met-Leu-Thr-Phe-Lys-Phe-Tyr-Met-Pro-

AAG.AAG.GCC.ACA.GAA.CTG.AAA.CAT.CTT.CAG.TGT.CTA.GAA.CGG.AGG.
Lys-Lys-Ala-Thr-Glu-Leu-Lys-His-Leu-Gln-Cys-Leu-Glu-Arg-Arg-
                                                  IL-2 ⟶
ACT.TAA.TAA ATG GTA.TCA.GAA.TAC.TGT.AGC.CAC.ATG.ATT.GGG.AGT.
Thr ter ter Met-Val-Ser-Glu-Tyr-Cys-Ser-His-Met-Ile-Gly-Ser-
            ⃪———M-CSF
GGA.CAC.CTG.CAG.TCT.CTG.CAG.CGG.CTG.ATT.GAC.AGT.CAG.ATG.GAG.
Gly-His-Leu-Gln-Ser-Leu-Gln-Arg-Leu-Ile-Asp-Ser-Gln-Met-Glu- ACC.TCG.TGC.CAA.ATT.ACA.TTT.GAG.TTT.GTA.GAC.CAG.GAA.CAG.TTG.
Thr-Ser-Cys-Gln-Ile-Thr-Phe-Glu-Phe-Val-Asp-Gln-Glu-Gln-Leu- AAA.GAT.CCA.GTG.TGC.TAC.CTT.AAG.AAG.GCA.TTT.CTC.CTG.GTA.CAA.
Lys-Asp-Pro-Val-Cys-Tyr-Leu-Lys-Lys-Ala-Phe-Leu-Leu-Val-Gln- TAC.ATA.ATG.GAG.GAC.ACC.ATG.CGC.TTC.AGA.GAT.AAC.ACC.CCC.AAT.
Tyr-Ile-Met-Glu-Asp-Thr-Met-Arg-Phe-Arg-Asp-Asn-Thr-Pro-Asn- GCC.ATC.GCC.ATT.GTG.CAG.CTG.CAG.GAA.CTC.TCT.TTG.AGG.CTG.AAG
Ala-Ile-Ala-Ile-Val-Gln-Leu-Gln-Glu-Leu-Ser-Leu-Arg-Leu-Lys AGC.TGC.TTC.ACC.AAG.GAT.TAT.GAA.GAG.CAT.GAC.AAG.GCC.TGC.GTC.
Ser-Cys-Phe-Thr-Lys-Asp-Tyr-Glu-Glu-His-Asp-Lys-Ala-Cys-Val- CGA.ACT.TTC.TAT.GAG.ACA.CCT.CTC.CAG.TTG.CTG.GAG.AAG.GTC.AAG.
Arg-Thr-Phe-Tyr-Glu-Thr-Pro-Leu-Gln-Leu-Leu-Glu-Lys-Val-Lys- AAT.GTC.TTT.AAT.GAA.ACA.AAG.AAT.CTC.CTT.GAC.AAG.GAC.TGG.AAT.
Asn-Val-Phe-Asn-Glu-Thr-Lys-Asn-Leu-Leu-Asp-Lys-Asp-Trp-Asn- ATT.TTC.AGC.AAG.AAC.TGC.AAC.AAC.AGC.TTT.GCT.GAA.TGC.TCC.AGC.
Ile-Phe-Ser-Lys-Asn-Cys-Asn-Asn-Ser-Phe-Ala-Glu-Cys-Ser-Ser- CAA.GAT.GTG.GTG.ACC.TGA.TAA.
Gln-Asp-Val-Val-Thr ter ter
           M-CSF ⟶
```

FIG. 20

```
                                    ATG.GCA.CCT.ACT.TCA.
                                    Met-Ala-Pro-Thr-Ser-
                                      |←—IL-2
AGT.TCT.ACA.AAG.AAA.ACA.CAG.CTA.CAA.CTG.GAG.CAT.TTA.CTG.CTG.
Ser-Ser-Thr-Lys-Lys-Thr-Gln-Leu-Gln-Leu-Glu-His-Leu-Leu-Leu-

GAT.TTA.CAG.ATG.ATT.TTG.AAT.GGA.ATT.AAT.AAT.TAC.AAG.AAT.CCC.
Asp-Leu-Gln-Met-Ile-Leu-Asn-Gly-Ile-Asn-Asn-Tyr-Lys-Asn-Pro-

AAA.CTC.ACC.AGG.ATG.CTC.ACA.TTT.AAG.TTT.TAC.ATG.CCC.AAG.AAG.
Lys-Leu-Thr-Arg-Met-Leu-Thr-Phe-Lys-Phe-Tyr-Met-Pro-Lys-Lys-

GCC.ACA.GAA.CTG.AAA.CAT.CTT.CAG.TGT.CTA.GAA.CGG.AGG.ACT.CAT.
Ala-Thr-Glu-Leu-Lys-His-Leu-Gln-Cys-Leu-Glu-Arg-Arg-Thr-His
                                       IL-2 —→|
TG  ATG GAA.GAA.GTA.TCA.GAA.TAC.TGT.AGC.CAC.ATG.ATT.GGG.AGT.
ter Met-Glu-Glu-Val-Ser-Glu-Tyr-Cys-Ser-His-Met-Ile-Gly-Ser-
        |←-M-CSF
GGA.CAC.CTG.CAG.TCT.CTG.CAG.CGG.CTG.ATT.GAC.AGT.CAG.ATG.GAG.
Gly-His-Leu-Gln-Ser-Leu-Gln-Arg-Leu-Ile-Asp-Ser-Gln-Met-Glu- ACC.TCG.TGC.CAA.ATT.ACA.TTT.GAG.TTT.GTA.GAC.CAG.GAA.CAG.TTG.
Thr-Ser-Cys-Gln-Ile-Thr-Phe-Glu-Phe-Val-Asp-Gln-Glu-Gln-Leu- AAA.GAT.CCA.GTG.TGC.TAC.CTT.AAG.AAG.GCA.TTT.CTC.CTG.GTA.CAA.
Lys-Asp-Pro-Val-Cys-Tyr-Leu-Lys-Lys-Ala-Phe-Leu-Leu-Val-Gln- TAC.ATA.ATG.GAG.GAC.ACC.ATG.CGC.TTC.AGA.GAT.AAC.ACC.CCC.AAT.
Tyr-Ile-Met-Glu-Asp-Thr-Met-Arg-Phe-Arg-Asp-Asn-Thr-Pro-Asn- GCC.ATC.GCC.ATT.GTG.CAG.CTG.CAG.GAA.CTC.TCT.TTG.AGG.CTG.AAG.
Ala-Ile-Ala-Ile-Val-Gln-Leu-Gln-Glu-Leu-Ser-Leu-Arg-Leu-Lys AGC.TGC.TTC.ACC.AAG.GAT.TAT.GAA.GAG.CAT.GAC.AAG.GCC.TGC.GTC.
Ser-Cys-Phe-Thr-Lys-Asp-Tyr-Glu-Glu-His-Asp-Lys-Ala-Cys-Val- CGA.ACT.TTC.TAT.GAG.ACA.CCT.CTC.CAG.TTG.CTG.GAG.AAG.GTC.AAG.
Arg-Thr-Phe-Tyr-Glu-Thr-Pro-Leu-Gln-Leu-Leu-Glu-Lys-Val-Lys- AAT.GTC.TTT.AAT.GAA.ACA.AAG.AAT.CTC.CTT.GAC.AAG.GAC.TGG.AAT.
Asn-Val-Phe-Asn-Glu-Thr-Lys-Asn-Leu-Leu-Asp-Lys-Asp-Trp-Asn- ATT.TTC.AGC.AAG.AAC.TGC.AAC.AAC.AGC.TTT.GCT.GAA.TGC.TCC.AGC.
Ile-Phe-Ser-Lys-Asn-Cys-Asn-Asn-Ser-Phe-Ala-Glu-Cys-Ser-Ser- CAA.GAT.GTG.GTG.ACC.TGA.TAA.
Gln-Asp-Val-Val-Thr ter ter
          M-CSF —→|
```

DNA ENCODING HUMAN COLONY-STIMULATING FACTORS

This is a continuation of application Ser. No. 07/815,603 filed Jan. 3, 1993, now abandoned, which is a continuation-in-part of application Ser. No. 07/304,692 filed Feb. 1, 1989, now abandoned, and a continuation-in-part of application Ser. No. 07/098,105 filed Sep. 17, 1987, now abandoned.

FIELD OF THE INVENTION

The present invention relates to a novel human colony-stimulating factors (CSFs), especially recombinant-type CSFs, useful as drugs and to a process for preparing them.

BACKGROUND OF THE INVENTION

Generally, specific proliferation and differentiation factors are required for the proliferation and differentiation of hematopoietic cells. Such factors participate in the differentiation and proliferation of hematopoietic cells into various blood cells, such as erythrocytes, granulocytes, macrophages, eosinophils, platelets and lymphocytes (Yasusada Miura, "Blood Stem Cells," Chugai Igaku Sha, 1983). Of these factors, CSFs are known as factors which stimulate the proliferation and differentiation of granulocyte precursor cells and macrophage precursor cells. Among the CSF's are G-CSF which is specific to the formation of granulocytes, M-CSF which is specific to the formation of macrophages, GM-CSF which acts to form both granulocytes and macrophages and multi-CSF(IL-3) which stimulates pluripotent stem cells.

The above-mentioned CSFs, because of their biological activity, are thought to alleviate the leukopenia resulting from cancer chemotherapy and radiotherapy as a common drawback of these therapies. Clininal research on CSFs is conducted from this viewpoint.

The CSFs are also known to have activity to promote the function of leukocytes (Lopez, A. F. et al., *J. Immunol.*, 131, 2983 (1983), Handam, E. et al., same, 122, 1134 (1979) and Vadas, M. A. et al., same, 130, 795 (1983)) and are therefore found effective as drugs for preventing and curing various infectious diseases.

Furthermore, the CSFs are found effective for curing myelogenous leukemia because of its differentiation inducing activity (Metcalf, D. et al., *Int. J. Cancer*, 30, 773 (1982)).

The activity of CSFs is found, for example, in the cultures of fetal cells, spleen cells, etc. in human urine and in the culture media of various incubated cell lines, and active fractions thereof are separated off and used. However, the CSF of any origin contains large quantities of analogous extraneous substances or the like derived from the starting material and is in itself low in concentration, so that these problems must be solved in preparing the CSF. In respect of homogeneity, yield, ease of operation, etc., therefore, methods still remain to be developed of commercially preparing CSFs as drugs.

We have already established "AGR-ON," a cell line derived from human leukemic T cells, which is capable of producing a large quantity of CSF constitutively in a homogeneous state (Unexamined Japanese Patent Publication SHO 59-169489). We have also developed a process for preparing a CSF from AGR-ON easily in a pure form and in a high yield and further clarified the structural and biochemical characteristics of the resulting CSF (Unexamined Japanese Patent Publication SHO 62-169799).

The CSF disclosed by the above invention is M-CSF, i.e., a glycoprotein which acts on normal bone marrow cells to promote the differentiation and proliferation of macrophages and which is characterized by the following physicochemical properties. The CSF is termed "AGR-ON.CSF."

a) Molecular weight 33,000 to 43,000 daltons as determined by SDS polyacrylamide gel electrophoresis under a non-reducing condition, and 23,000 to 40,000 daltons as determined by gel filtration under a non-reducing condition in the presence of SDS.

b) N-terminal amino acid sequence of the protein portion

The sequence of the following primary structural formula.

Val—Ser—Glu—Tyr—Cys—Ser—His—Met—Ile—Gly—Ser—
Gly—His—Leu—Gln—Ser—Leu—Gln—Arg—Leu—Ile—Asp—
Ser—Gln—Met—Glu—Thr

SUMMARY OF THE INVENTION

The main object of the present invention is to provide techniques for preparing and supplying human M-CSFs by genetic engineering techniques and the human M-CSFs useful as drugs.

BRIEF DESCRIPTION OF THE DRAWINGS

FIGS. 2-1 to 2-4 show the nucleotide sequence of the cDNA as determined by the Maxam-Gilbert chemical modification method and the dideoxynucleotide chain termination method using M13 phage;

FIGS. 3-1 and 3-2 show the primary structure of M-CSF precursor protein coded for by the cDNA;

FIGS. 4-1 to 4-4 show the nucleotide sequence of the cDNA of λcM11;

FIGS. 5-1 to 5-3 show the primary structure of M-CSF precursor protein coded for by the λcM11 cDNA;

FIGS. 9-1 to 9-3 are diagrams showing a procedure for preparing M-CSF expression plasmid pIN-III (lpp$^P$-5)-OmpA-MCSF11-NV151;

FIG. 10 shows the amino acid sequence coded for by the M-CSF expression plasmid pIN-III(lpp$^P$-5)-OmpA-MCSF11-NV151;

FIG. 11 shows the amino acid sequence coded for by M-CSF expression plasmid pIN-III(lpp$^P$-5)-OmpA-MCSF11-NV143;

FIGS. 12-1 to 12-2 are diagrams showing a procedure for preparing M-CSF expression plasmid pcDM.CSF11-dhfr;

FIGS. 15 to 20 show the structures of the two-cistron expression systems according to Example 3, (1) to (4);

DETAILED DESCRIPTION OF THE INVENTION

Figure 1:
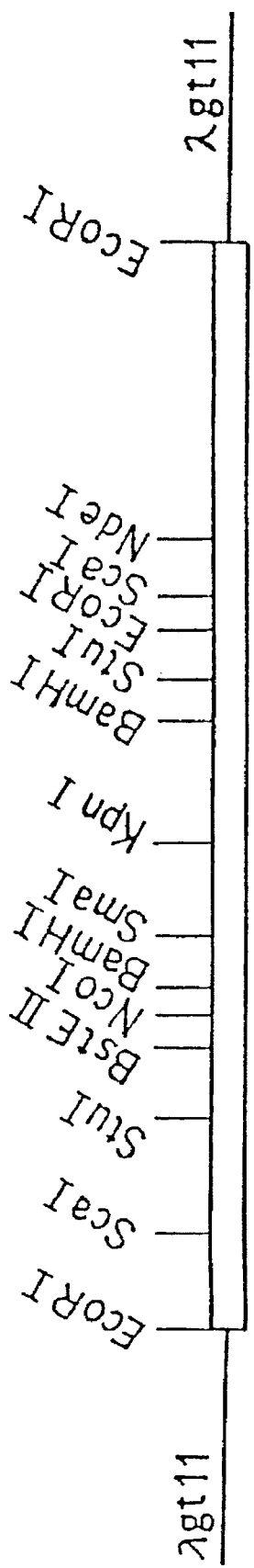
FIG. 1 is a restriction enzyme map of cDNA of λcM5.

The above object and other features of the invention will become apparent from the following detailed description.

According to the invention, a biologically active recombinant human M-CSF obtained by expressing a human M-CSF gene coding for the amino acid sequence of the following formula (1) in its entirety or devoid of a portion thereof is provided.

Formula (1):

```
   1                                         10
Met—Thr—Ala—Pro—Gly—Ala—Ala—Gly—Arg—Cys—

20
Pro—Pro—Thr—Thr—Trp—Leu—Gly—Ser—Leu—Leu—

30
Leu—Leu—Val—Cys—Leu—Leu—Ala—Ser—Arg—Ser—

40
Ile—Thr—Glu—Glu—Val—Ser—Glu—Tyr—Cys—Ser—

50
His—Met—Ile—Gly—Ser—Gly—His—Leu—Gln—Ser—

60
Leu—Gln—Arg—Leu—Ile—Asp—Ser—Gln—Met—Glu—

70
Thr—Ser—Cys—Gln—Ile—Thr—Phe—Glu—Phe—Val—

80
Asp—Gln—Glu—Gln—Leu—Lys—Asp—Pro—Val—Cys—

90
Tyr—Leu—Lys—Lys—Ala—Phe—Leu—Leu—Val—Gln—

100
X—Ile—Met—Glu—Asp—Thr—Met—Arg—Phe—Arg—

110
Asp—Asn—Thr—Pro—Asn—Ala—Ile—Ala—Ile—Val—

120
Gln—Leu—Gln—Glu—Leu—Ser—Leu—Arg—Leu—Lys—

130
Ser—Cys—Phe—Thr—Lys—Asp—Tyr—Glu—Glu—His—

140
Asp—Lys—Ala—Cys—Val—Arg—Thr—Phe—Tyr—Glu—

150
Thr—Pro—Leu—Gln—Leu—Leu—Glu—Lys—Val—Lys—

160
Asn—Val—Phe—Asn—Glu—Thr—Lys—Asn—Leu—Leu—

170
Asp—Lys—Asp—Trp—Asn—Ile—Phe—Ser—Lys—Asn—

180
Cys—Asn—Asn—Ser—Phe—Ala—Glu—Cys—Ser—Ser—

190
Gln—Asp—Val—Val—Thr—Lys—Pro—Asp—Cys—Asn—

200
Cys—Leu—Tyr—Pro—Lys—Ala—Ile—Pro—Ser—Ser—

210
Asp—Pro—Ala—Ser—Val—Ser—Pro—His—Gln—Pro—

220
Leu—Ala—Pro—Ser—Met—Ala—Pro—Val—Ala—Gly—

230
Leu—Thr—Trp—Glu—Asp—Ser—Glu—Gly—Thr—Glu—

240
Gly—Ser—Ser—Leu—Leu—Pro—Gly—Glu—Gln—Pro—

250
Leu—His—Thr—Val—Asp—Pro—Gly—Ser—Ala—Lys—

260
Gln—Arg—Pro—Pro—Arg—Ser—Thr—Cys—Gln—Ser—

270
Phe—Glu—Pro—Pro—Glu—Thr—Pro—Val—Val—Lys—

280
Asp—Ser—Thr—Ile—Gly—Gly—Ser—Pro—Gln—Pro—

290
Arg—Pro—Ser—Val—Gly—Ala—Phe—Asn—Pro—Gly—

300
Met—Glu—Asp—Ile—Leu—Asp—Ser—Ala—Met—Gly—

310
Thr—Asn—Trp—Val—Pro—Glu—Glu—Ala—Ser—Gly—

320
Glu—Ala—Ser—Glu—Ile—Pro—Val—Pro—Gln—Gly—

330
Thr—Glu—Leu—Ser—Pro—Ser—Arg—Pro—Gly—Gly—

340
Gly—Ser—Met—Gln—Thr—Glu—Pro—Ala—Arg—Pro—

350
Ser—Asn—Phe—Leu—Ser—Ala—Ser—Ser—Pro—Leu—

360
Pro—Ala—Ser—Ala—Lys—Gly—Gln—Gln—Pro—Ala—

370
Asp—Val—Thr—Gly—Thr—Ala—Leu—Pro—Arg—Val—

380
Gly—Pro—Val—Arg—Pro—Thr—Gly—Gln—Asp—Trp—

390
Asn—His—Thr—Pro—Gln—Lys—Thr—Asp—His—Pro—

400
Ser—Ala—Leu—Leu—Arg—Asp—Pro—Pro—Glu—Pro—

410
Gly—Ser—Pro—Arg—Ile—Ser—Ser—Pro—Arg—Pro—

420
Gln—Gly—Leu—Ser—Asn—Pro—Ser—Thr—Leu—Ser—

430
Ala—Gln—Pro—Gln—Leu—Ser—Arg—Ser—His—Ser—

440
Ser—Gly—Ser—Val—Leu—Pro—Leu—Gly—Glu—Leu—

450
Glu—Gly—Arg—Arg—Ser—Thr—Arg—Asp—Arg—Arg—

460
Ser—Pro—Ala—Glu—Pro—Glu—Gly—Gly—Pro—Ala—

470
Ser—Glu—Gly—Ala—Ala—Arg—Pro—Leu—Pro—Arg—

480
Phe—Asn—Ser—Val—Pro—Leu—Thr—Asp—Thr—Gly—

490
His—Glu—Arg—Gln—Ser—Glu—Gly—Ser—Ser—Ser—

500
Pro—Gln—Leu—Gln—Glu—Ser—Val—Phe—His—Leu—

510
Leu—Val—Pro—Ser—Val—Ile—Leu—Val—Leu—Leu—
```

-continued

```
                                                520
Ala—Val—Gly—Gly—Leu—Leu—Phe—Tyr—Arg—Trp—

530
Arg—Arg—Arg—Ser—His—Gln—Glu—Pro—Gln—Arg—

540
Ala—Asp—Ser—Pro—Leu—Glu—Gln—Pro—Glu—Gly—

550
Ser—Pro—Leu—Thr—Gln—Asp—Asp—Arg—Gln—Val—

554
Glu—Leu—Pro—Val
``` wherein X is Tyr or Asp.

Peptides and amino acids are herein referred to by symbols according to the amino acid nomenclature adopted by IUPAC or by symbols conventionally used in the art. Nucleotide sequences and nucleic acids are also expressed similarly.

As already described, the M-CSF of the present invention, because of its biological activity, is useful especially in the field of medicinals as a drug for preventing and curing diseases involving leukopenia, as an auxiliary agent for the bone marrow transplantation, as a drug for preventing and curing various infectious diseases, as an anticancer drug, etc.

The human M-CSFs of the present invention are recombinant-type M-CSFs prepared by genetic engineering techniques and are useful in the above-mentioned fields.

The human M-CSF of the invention is prepared utilizing a gene coding for the factor (hereinafter referred to as the "gene of the invention"), i.e., by preparing a recombinant DNA for expressing the gene in host cells, introducing the DNA into host cells for transformation and cultivating the resulting transformant.

A detailed description will be given below of the gene of the invention for use in preparing the human M-CSF of the invention.

The gene of the invention is prepared, for example, from human cells having ability to produce M-CSF, more specifically and advantageously from mRNA separated from AGR-ON. The preparation of the gene will hereinafter be described with reference to AGR-ON although the gene can be similarly prepared from other cells. AGR-ON is a human cell line derived from human leukemic T cells and having the characteristics described in Unexamined Japanese Patent Publication SHO 59-169489. The cell line is deposited in American Type Culture Collection (ATCC) as ATCC Deposition No.CRL-8199.

The mRNA is isolated from AGR-ON basically by a usual extraction procedure. Stated more specifically, AGR-ON is cultured, for example, in CEM medium, CMRL-1066 medium, DM-160 medium, Eagle's minimum essential medium (Eagle's MEM), Fisher's medium, F-10 medium, F-12 medium, L-15 medium, NCTC-109 medium, RPMI-1640 medium or the like, with fetal calf serum (FCS) or like serum, or albumin or like serum component added thereto when desired. AGR-ON is inoculated in the medium at a concentration of about $1\times10^4$ to $1\times10^7$ cells/ml and is incubated by a usual method, such as culturing in a $CO_2$ incubator, at about 30° to about 40° C., preferably at about 37° C., for 1 to 5 days. When the CSF has been produced and accumulated, the cultured cells are lysed partially or completely with a suitable detergent, such as SDS, NP-40, Triton X100 or deoxycholic acid, or by a homogenizer or by some physical method such as a freeze-thaw method. The chromosomal DNA is then sheared to some extent by Polytron (product of Kinematica, Switzerland) or like mixer or a syringe. Proteins are thereafter removed from a nucleic acid fraction for the extraction of total RNA. Generally used for this procedure is, for example, the guanidinium-CsCl ultracentrifugation method (Chirgwin, J. M. et al., *Biochemistry*, 18, 5294 (1979)).

To prevent the degradation of RNA with RNase, the above method or procedure can be carried out in the presence of RNase inhibitors, such as heparin, polyvinyl sulfate, diethyl pyrocarbonate and vanadyl-ribonucleoside complex.

mRNAs can be separated from the extracted RNA and purified by a column method or batchwise method using, for example, oligo dT-cellulose, poly-U-Sepharose or the like.

The mRNA corresponding to the desired M-CSF can be concentrated and identified, for example, by fractionating the mRNAs by sucrose density gradient centrifugation, introducing the fractions into a protein translation system, such as *Xenopus laevis* oocytes, or rabbit reticulocyte lysates, wheat germ extracts or like cell-free system to cause the system to translate the fraction into a protein, and examining the protein for M-CSF activity, whereby the presence of the desired mRNA can be recognized. Instead of the determination of the M-CSF activity, an immunoassay using an antibody against M-CSF is also available in identifying the desired mRNA.

The purified mRNA thus obtained, which is usually unstable, is converted to a stable cDNA, which is then coupled to a replicon derived from a microorganism for the amplification of the desired gene. The conversion of the mRNA to the cDNA, i.e. the synthesis of the desired gene of the invention can be done generally in the following manner.

Using oligo dT as a primer (which may be dT-tailed vector) and the mRNA as a template, a single-stranded complementary DNA to the mRNA is synthesized therefrom in the presence of dNTP (dATP, dGTP, dCTP or dTTP) with use of a reverse transcriptase. The next step differs as follows depending on whether oligo dT or dT-tailed vector is used.

In the former case, the mRNA used as a template is removed by alkaline hydrolysis, and a double-stranded DNA is synthesized from the single-stranded DNA serving as a template, using a reverse transcriptase or DNA polymerase I. Subsequently, both ends of the double-stranded DNA are treated with exonuclease, a suitable linker DNA or a tail of bases amenable to annealing is attached to each end, and the resulting DNA is inserted into a suitable vector, such as EK-type plasmid vector or λgt phage vector.

In the latter case, a linear vector-cDNA: mRNA and a linker DNA (frequently used as such is a DNA fragment having a region which can be autonomously replicated in an animal cell and a promoter for the transcription) are annealed into a circular form. The mRNA is thereafter replaced by the DNA strand in the presence of dNTP and also in the presence of both RNaseH and DNA polymerase I to obtain a recombinant plasmid containing cDNA.

The DNA thus obtained is then introduced into a suitable host, such as *Escherichia coli, Bacillus subtilis* or *Saccharomyces cerevisiae*, for transformation. The DNA can be introduced into the host, using a usual method, for example, by collecting cells preferably in the logarithmic growth phase, treating the cells with $CaCl_2$ to make them ready to uptake the DNA. This method can be practiced in the presence of $MgCl_2$ or RbCl as is generally known to achieve an improved transformation efficiency. The host cells can be converted to spheroplasts or protoplasts before transformation.

From among the transformants thus prepared, the one harboring the plasmid containing cDNA of the desired M-CSF can be selected, for example, by one of the following methods.

(1) Screening with use of synthetic oligonucleotide probe

When the amino acid sequence of the desired protein is wholly or partially has been elucidated (i.e. when a specific sequence of several amino acids in any region of the protein is known), oligonucleotides corresponding to the amino acids are synthesized in view of codon usage of the host cells. Thus synthesized oligonucleotides can be used either as a single or mixed probe. In the latter case, the number of combinations can be reduced by using inosine. The oligonucleotide is labeled with $^{32}P$ or $^{35}S$, and hybridized with nitrocellulose filters having DNAs of the transformants fixed thereto. The desired transformant is selected from the positive hybrids obtained.

(2) Screening of animal cells producing M-CSF

The transformants are incubated to amplify the desired genes, and animal cells are transfected with the amplified genes. (The plasmid to be used in this case is one autonomously replicable and having a mRNA transcription promotor, or one that will be integrated into an animal cell chromosome.) Thus, the cells are caused to produce proteins coded by the respective genes. The supernatant of each culture of such cells, or the cell extract is assayed for M-CSF activity, or M-CSF is detected using an antibody against M-CSF, whereby the desired transformant having the cDNA specifying M-CSF is selected.

(3) Selection using antibody against M-CSF cDNA is introduced into vectors which permit the transformant to express a protein. The desired transformant producing M-CSF is detected using an antibody against M-CSF and a second antibody against the antibody.

(4) Use of selective hybridization-translation system mRNAs from M-CSF producing cells are hybridized with the transformant-derived cDNA immobilized on the nitrocellulose filters, and the desired mRNA corresponding to the cDNA is recovered. The recovered mRNA is subjected to a protein translation system, such as *Xenopus laevis* oocytes, or rabbit reticulocyte lysates, wheat germ extracts or like cell-free system, and is thereby translated into protein. The protein is assayed for M-CSF activity, or is examined for the presence of M-CSF using an antibody against M-CSF to identify the desired transformant.

The DNA coding for M-CSF is obtained from the desired transformant by a known method, for example, by separating a fraction corresponding to the plasmid DNA from the cell, and isolating the cDNA region from the plasmid DNA.

Figures 1, 9:
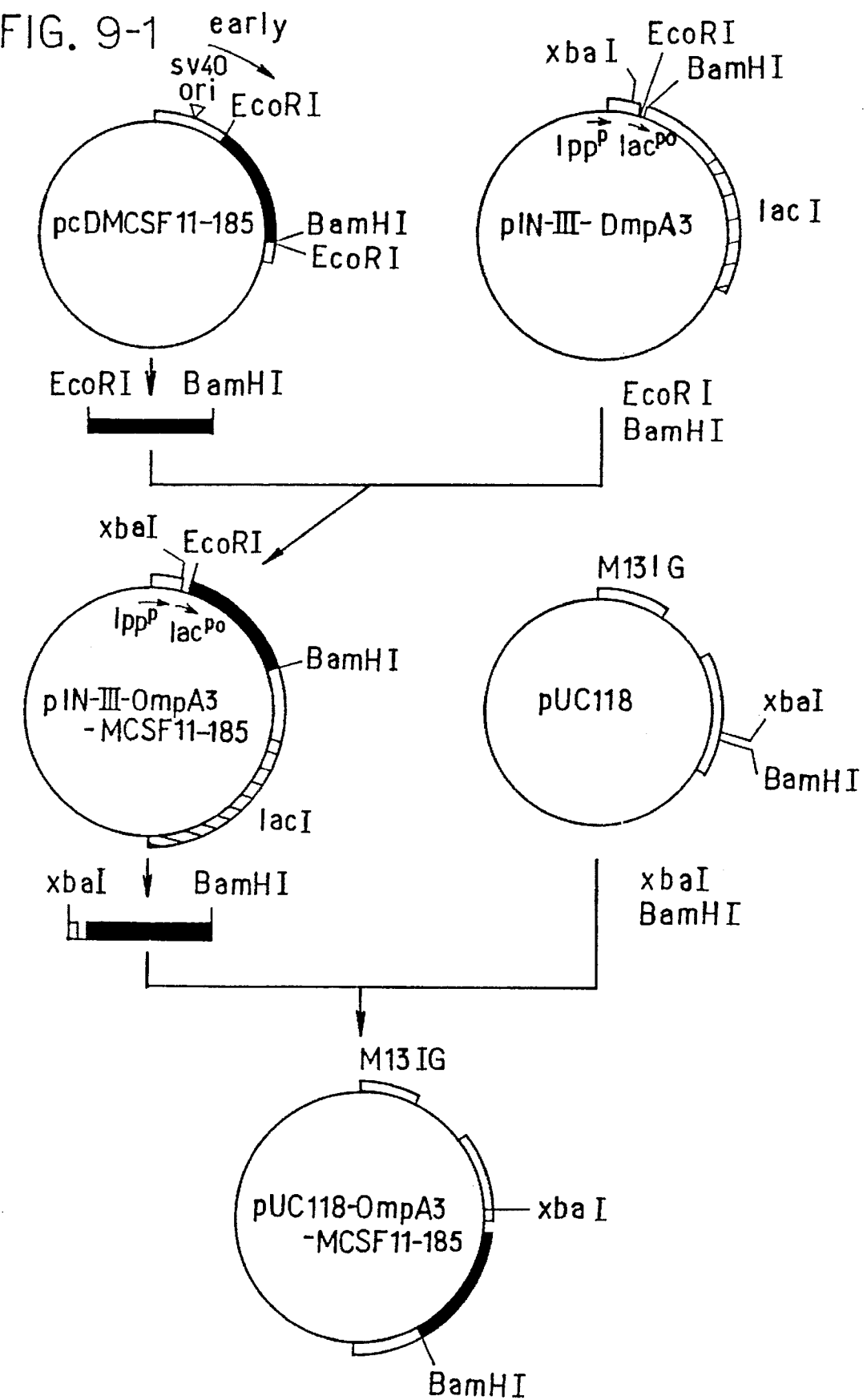
Figures 2, 9:
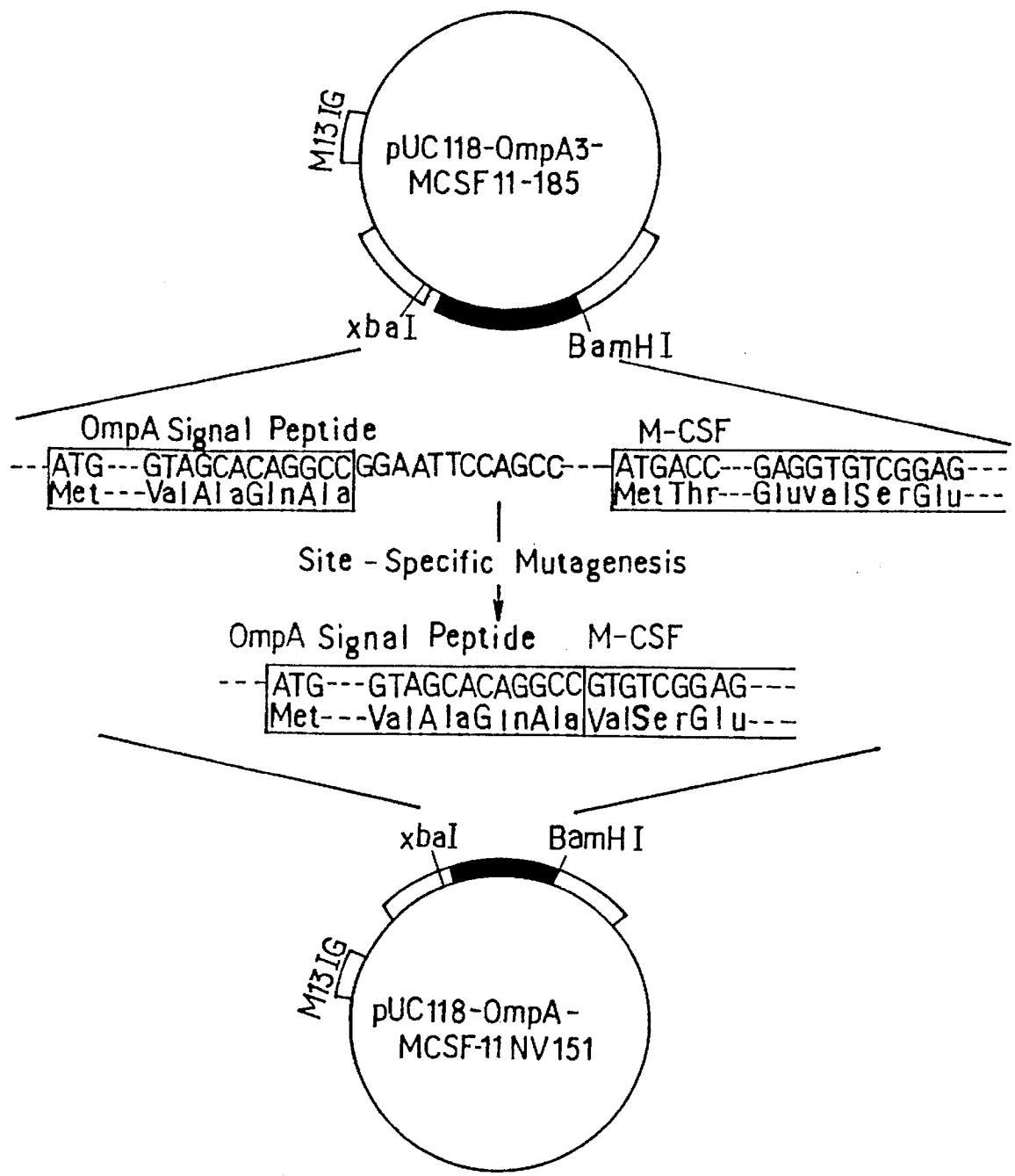
Figures 3, 9:
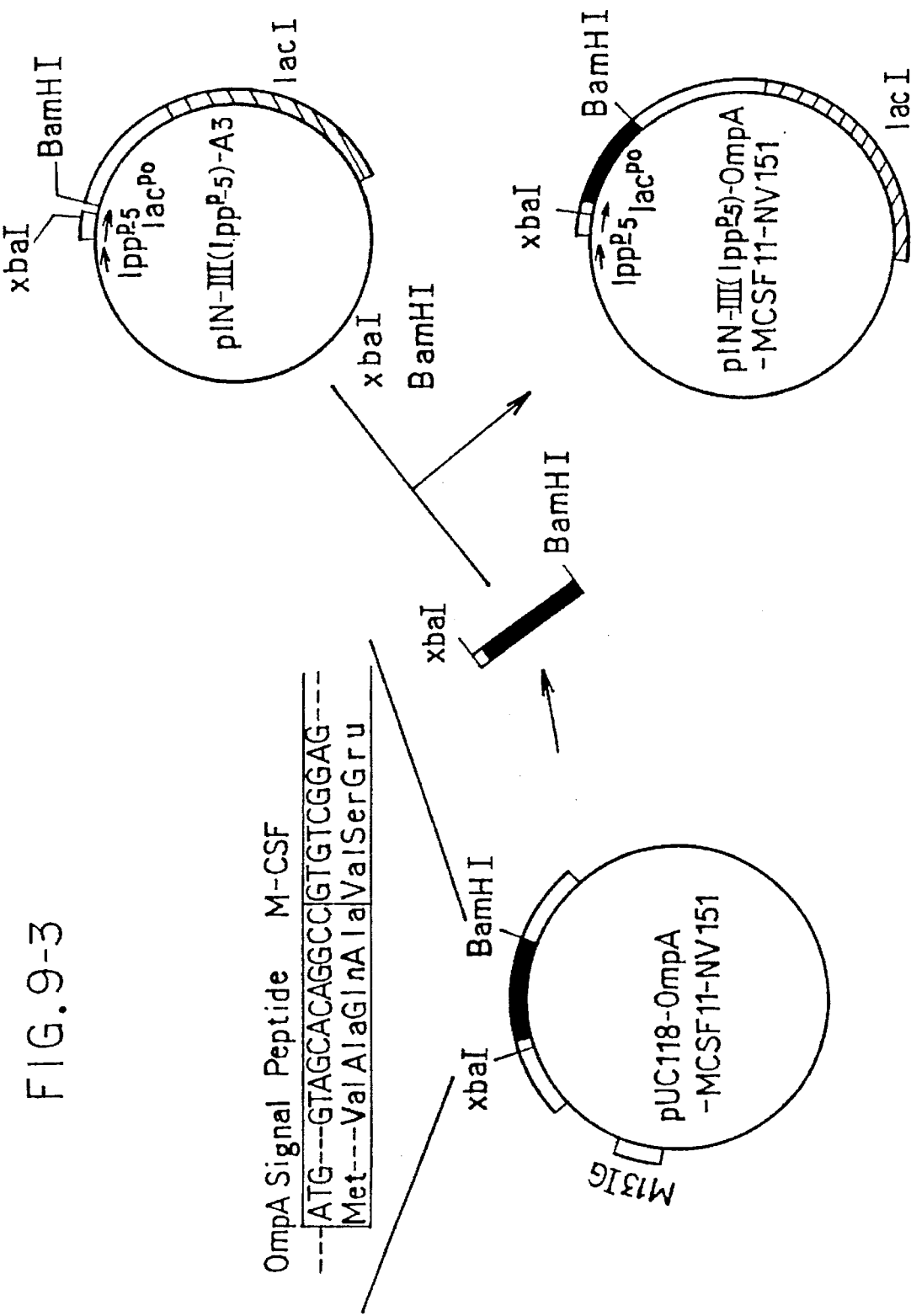

The DNA thus obtained is an example of the gene of the invention coding for a human M-CSF precursor which is defined by the sequence of 372 amino acids shown in FIG. 3 or the sequence of 554 amino acids shown in FIG. 5.

For the substance, obtained by genetic engineering techniques using the gene of the invention, to exhibit the biological activity of human M-CSF, the gene need not always have the above DNA, i.e. the DNA sequence coding for the entire amino acid sequence of the human M-CSF precursor. For example, DNAs coding for portions of the amino acid sequence are also included in the gene of the invention insofar as they permit exhibition of the biological activity of human M-CSF.

The fact that the entire amino acid sequence represented by the formula (1) is not always required for the exhibition of human M-CSF biological activity is apparent also from the fact that the precursor with the sequence of FIG. 3 has the 372nd amino acid (Pro) in the formula (1) at its C terminus, the fact that AGR-ON.CSF has the 35th amino acid (Val) at its N terminus, and the fact that the preparation of AGR-ON.CSF affords a by-product (minor component) which is a biological active M-CSF having the 33rd amino acid (Glu) or the 37th amino acid (Glu) at its N terminus. Further findings as to the similarity in the primary structure between hemopoietins appear to indicate that a naturally occurring M-CSF is present which has the 27th amino acid (Ala) at its N terminus (J. W. Schrader et al., *Proc. Natl. Acad. Sci. U.S.A.*, Vol. 83, pp. 2458–2462 (1986)).

Further as shown in the example concerned and given later, it has been confirmed that the portion of the amino acid sequence of the formula (1) from the 164th amino acid (Trp) to the amino acid at the C terminus is not always necessary for the exhibition of the biological activity of human M-CSF.

Consequently, the gene of the invention is characterized in that the gene specifies a biologically active human M-CSF molecule and has a novel DNA sequence based on the information of the amino acid sequence shown in the formula (1). Stated more specifically, the gene of the present invention includes the DNA coding for the entire amino acid sequence represented by the formula (1), a DNA coding for the amino acid sequence of the formula (1) which is deficient in a portion thereof closer to the N terminus, e.g. in the sequence of the 1st to the 26th, the 1st to the 32nd, the 1st to the 34th or the 1st to the 36th amino acids, and/or in a portion thereof closer to the C terminus, e.g. in the whole or part of the sequence from the 164th amino acid to the C-terminus, and DNAs substantially equivalent to these DNAs.

The gene of the invention can also be prepared by a usual process for the chemical synthesis of nucleic acid, e.g. the phosphite triester process (*Nature*, 310, 105 (1984)), based on the above information. The present gene can further be prepared from the DNA coding for the polypeptide comprising the sequence of 372 amino acids shown in FIG. 3 or of 554 shown in FIG. 5 by a usual process.

When the gene is to be prepared from the DNA coding for the polypeptide comprising the sequence of 372 or 554 amino acids, usual procedures or means can be employed for the chemical synthesis of portions of the DNA, for the enzymatic treatments for cleaving, removing, adding or ligating DNA strands, and for the isolation and purification, or replication and selection, of the desired DNA. Thus, various known methods are available which are generally employed in the art for genes or DNA strands other than those of the invention. For example, the desired DNA can be isolated and purified by agarose gel electrophoresis, while codons in the nucleic acid sequence can be modified, for example, by site-specific mutagenesis (*Proc. Natl. Acad. Sci.*, 81, 5662–5666 (1984)). The codon to be selected for the desired amino acid is not limited specifically but can be determined in a usual manner in view of the codon usage for the host cell to be utilized, etc.

The DNA sequence of the gene of the invention obtained by the above process can be determined and confirmed, for example, by the Maxam-Gilbert chemical modification method (*Meth. Enzym.*, 65, 499–560 (1980)) or by the dideoxynucleotide chain termination method using M13 phage (Messing, J. and Vieira, J., *Gene*, 19, 269–276 (1982)).

Thus, human M-CSF can be prepared easily in a large quantity by recombinant DNA techniques using the gene of the invention.

While it is essential to use the above-specified gene (DNA) of the invention in this process for preparing the human M-CSF, the human M-CSF can be prepared basically by genetic engineering (Molecular Cloning, by T. Maniatis et al., Cold Spring Harbor Laboratory (1982); *Science*, 224, 1431 (1984); *Biochem. Biophys. Res. Comm.*, 130, 692

(1985); *Proc. Natl. Acad. Sci., U.S.A.*, 80, 5990 (1983); EP Laid-Open Pat. Appln. No.187991).

More specifically, the human M-CSF can be produced by preparing a recombinant DNA which can express the gene of the invention in host cells, introducing the DNA into the host cell and cultivating the transformant.

Useful host cells can be either eukaryotic or prokaryotic cells. The eukaryotic cells include cells of vertebrate animals, yeasts, etc. Generally used as cells of vertebrate animals are, for example, COS cells which are cells of monkey (Y. Gluzman, *Cell*, 23, 175–182 (1981)), dihydrofolate reductase defective strain of Chinese hamster ovary cell (G. Urlaub and L. A., Chasin, *Proc. Natl. Acad. Sci., U.S.A.*, 77, 4216–4220 (1980)), etc., while useful cells are not limited to these cells. Useful expression vectors of vertebrate cells are those having a promotor positioned upstream of the gene to be expressed, RNA splicing sites, polyadenylation site, transcription termination sequence, etc. These vectors may further have a replication origin when required. Examples of useful expression vectors include pSV2dhfr having an early promotor of SV40 (S. Sabramani, R. Mulligan and P. Berg. *Mol. Cell. Biol.*, 1, 854–864 (1981)), which is not limitative.

Yeasts are widely used as eukaryotic micro-organisms, among which those of the genus Saccharomyces are generally usable. Examples of popular expression vectors of yeasts and like eukaryotic microorganisms include pAM82 having a promotor for acid phosphatase gene A. Miyanohara et al., *Proc. Natl. Acad. Sci., U.S.A.*, 80, 1–5 (1983), etc.

*E. coli* and *Bacillus subtilis* are generally used as prokaryotic hosts. The present invention employs, for example plasmid vectors capable of replication in the host. To express the gene of the invention in the vector, expression plasmids can be used which have a promotor and SD (Shine-Dalgarno) sequence upstream to the present gene and ATG required for initiating protein synthesis. Widely used as host *E. coli* is *E. coli* K12 strain. pBR322 is a vector which is generally used. However, these are not limitative, and various known strains and vectors are usable. Examples of promotors usable are tryptophan promotor, $P_L$ promotor, lac promotor, lpp promotor, etc. The gene can be expressed with use of any of these promotors.

For preparing the human M-CSF with use of the gene of the invention, it is desirable, for example, to use COS cells as host cells. The expression vector that can be used in this method is one having SV40 replication origin, capable of autonomously replicating in the COS cell and having a transcription promotor, transcription termination signal, RNA splicing site, etc. For example, when plasmid pcDE is used as shown in the example to follow, the gene of the invention is inserted into the plasmid at the site of restriction enzyme EcoRI positioned downstream from SV40 early promotor, whereby the desired expression plasmid can be obtained. The desired recombinant DNA thus obtained can be introduced into the host cell by a common method. For example, the expression plasmid prepared by inserting the desired gene into the plasmid pcDE can be introduced into COS cells by the DEAE-dextran method or calcium phosphate-DNA coprecipitation method, consequently readily giving the desired transformant.

For preparing the human M-CSF with use of the gene of the invention, another process is desirable in which dihydrofolate reductase defective strain of Chinese hamster ovary cell (CHO-Duk dhfr) is used as the host.

For the preparation of the human M-CSF with use of the gene of the invention, another process is desirable in which a prokaryote such as *E. coli* is used as the host, and a signal peptide is used for secreting and expressing the desired M-CSF outside the inner membrane. Examples of useful signal peptides are various known ones including, for example, Lpp, OmpA, OmpF, PhoE and like outer membrane proteins, and PhoA, Bla, PstS and like periplasm proteins, among which OmpA is especially preferable.

For the preparation of the human M-CSF with use of the gene of the invention, another process is desirable wherein a prokaryote such as *E. coli* is used as the host, and the M-CSF is expressed by a two-cistron system which is a gene expression system comprising two cistrons in sequence. This process yields the desired M-CSF in a large quantity with good stability as accumulated in host cells. This process for preparing the M-CSF of the invention will be described in detail. First, an expression plasmid is prepared which two cistrons, i.e., a gene as the first cistron coding for a suitable polypeptide, and the gene of the invention as the second cistron. It is critical that the plasmid contain upstream from the first cistron a promoter and SD sequence for expressing the gene, and further contain downstream from the first cistron but upstream from the second cistron a synthetic linker which contains an SD sequence for expressing the second cistron, a termination codon for the first cistron and a starting codon for the second cistron, as arranged in this order.

The gene for use as the first cistron may be a synthetic or natural gene insofar as the gene can be expressed by the host. However, it is noted that the polypeptide encoded in the first cistron is different from the M-CSF of the invention and must subsequently be separated off, so that it is desirable that the polypeptide be hydrophobic and have a molecular weight greatly different from that of the M-CSF. It is therefore desired that the first cistron be one coding for such a polypeptide. Examples of preferred first cistrons are genes and fragments thereof coding for IL-2, IFN-α, -β and -γ, etc. and coding for about 50 to about 100 amino acid residues.

The promoter and SD sequence arranged upstream from the first cistron are those already known. Examples of such promoters are trp promoter, tac promoter, $P_L$ promoter, $P_R$ promoter, lpp promoter, OmpA promoter, lac promoter and the like, among which trp promoter, $P_L$ promoter and $P_R$ promoter are especially desirable. Examples of useful SD sequences are sequences of 3 to 9 base pairs, such as GGAG and AGGA, capable of forming a hydrogen bond with the 3' terminus of 16S rRNA of prokaryotic cells.

The starting codon and the termination codon present in the synthetic linker to be provided between the first cistron and the second cistron can be any of naturally occurring ones. These codons need not be used each in a complete form, for example, as TGA and ATG, but can be used in a partly overlapping form, for example, as TGATG, TAATG, etc.

The expression plasmid for use in the two-cistron system can be constructed by a usual method (Y. Saito et al., *J. Biochem.*, 101, 1281–1288 (1987); B. S. Schoner et al., *Proc. Natl. Acad. Sci., U.S.A.*, 83, 8506–8510 (1986)). It is especially desirable to prepare the plasmid, for example, by cleaving a plasmid containing the M-CSF gene of the invention with a suitable restriction enzyme, isolating and purifying the fragment containing the M-CSF gene by a usual method, preparing the synthetic linker, for example, by a DNA synthesizer, attaching the linker to the fragment at the upstream side of the M-CSF gene with T4DNA ligase, and incorporating the resulting DNA fragment into a plasmid containing the first cistron and capable of expressing the same, at the proper position. Alternatively, the expression plasmid suitable for the desired two-cistron system can be prepared from the DNA fragment obtained by the above method and containing the second cistron as attached to the synthetic linker, by attaching the first cistron to the upstream end of the fragment, and introducing the resulting DNA fragment into a plasmid having a suitable protein expression system.

The plasmid thus obtained is introduced into suitable host cells for transformation, whereby the desired transformant can be obtained through the two-cistron system. When the transformant is used, the protein relating to the first cistron and the desired M-CSF relating to the second cistron can be expressed individually. The products can be analyzed or identified for example, by SDS-PAGE, Western blotting method or the like, and can be purified as separated from each other by the various methods to be described later.

The desired transformant can be cultivated by a usual method, whereby biologically active human M-CSF is produced and accumulated. The medium to be used for the incubation is one suitably selected from among those usually used for the host cell employed. For incubating the transformant with use of $E.$ $coli$ or the like as the host, for example, LB medium, E medium, M9 medium, M63 medium and the like are usable. Various carbon sources, nitrogen sources, inorganic salts, vitamins, natural extracts, physiologically active substances, etc. which are generally known can be added to these media when required. Examples of media usable for COS cells are RPMI-1640 medium, Dulbecco's modified Eagle's MEM, etc. which may be supplemented with fetal calf serum (FCS) or like serum component when so required. The transformant can be incubated under conditions suitable for the growth of host cells, e.g., at a pH of about 5 to about 8, preferably about 7, and at a temperature of about 20° to about 43° C., preferably about 37° C., in the case of $E.$ $coli$.

The M-CSF produced by the transformant intra- or extracellularly can be separated off and purified by various separation procedures utilizing the physical or chemical properties of the product. (See for example, "Biological Data Book II," pp. 1175–1259, 1st edition, 1st print, Jun. 23, 1980, published by Kabushiki Kaisha Tokyo Kagakudojin; $Biochemistry$, Vol. 25, No.25, 8274–8277 (1968); $Eur.$ $J.$ $Biochem.$, 163, 313–321 (1987)). Examples of useful procedures are reconstitution treatment, treatment with use of a usual protein precipitating agent, centrifugation, osmotic shock method, ultrasonication, ultrafiltration, molecular sieve chromatography (gel filtration), adsorption chromatography, ion-exchange chromatography, affinity chromatography, high-performance liquid chromatography (HPLC) and like liquid chromatography, dialysis, and combinations of such procedures.

According to a preferred method of separation, the desired substance is partially purified, from the culture supernatant. First the partial purification is conducted, for example, by a treatment using a salting-out agent such as ammonium sulfate or sodium sulfate and/or ultrafiltration using a flat ultrafiltration membrane, hollow fiber membrane or the like. These treatments are conducted in the same manner as usually done under usual conditions.

The roughly purified product thus obtained is then subjected to adsorption chromatography, affinity chromatography, gel filtration, ion-exchange chromatography, reverse-phase chromatography or the like, or a combination of such procedures to obtain the desired homogeneous substance.

Adsorption chromatography can be conducted using, for example, phenyl-Sepharose, octyl-Sepharose or like resin.

Affinity chromatography can be practiced by chromatography utilizing, for example, ConA-Sepharose, Lentil lectin-Sepharose (product of Pharmacia) or like resin, when so desired.

Gel filtration can be practiced using an agent which is made of dextran gel, polyacrylamide gel, agarose gel, polyacrylamide-agarose gel, cellulose or the like. Examples of useful materials commercially available are Sephadex G type, Sepharose type, Sephacryl type (all products of Pharmacia), Cellulofine (product of Chisso Corporation), Biogel P type, Biogel A type (both products of Bio Rad Lab.), Ultrogel AcA (product of LKB), TSK-GEL SW type (product of Tosoh Corporation), etc.

Ion exchange chromatography can be conducted by chromatography using an anionic ion exchange material, for example with diethylaminoethyl (DEAE) or the like serving as the exchange group.

Reverse-phase chromatography can be conducted using a column which comprises a substrate of silica gel or the like having coupled thereto a ligand such as $C_1$, $C_3$ or $C_4$ alkyl, cyanopropyl or phenyl. More specifically, the chromatography can be conducted with $C_4$ Hi-Pore Reverse-Phase HPLC column (RP-304, Bio-Rad Laboratories) using acetonitrile, trifluoroacetic acid (TFA), water or the like, or a mixture of such solvents as the eluent.

By the processes described above, the desired M-CSF can be commercially produced with high purity in high yields.

The M-CSFs obtained in this way are in common in that they have CSF activity although slightly different in the N-terminal amino acid sequence, molecular weight, isoelectric point, etc. depending on the kind of gene used for the preparation and kind of system for expressing the gene. Of these M-CSFs, especially desirable are those obtained in the examples given latter.

For use as a drug, the M-CSF of the present invention is formulated into pharmacological compositions containing an effective amount of M-CSF and a usual pharmacologically acceptable nontoxic excipient. The composition is given via a route of administration suited to the form of the composition. Such compositions are, for example, in the form of liquid preparations including solution, suspension, emulsion and the like, which are given usually orally, intravenously, subcutaneously, intracutaneously or intramuscularly. Such forms or methods of administration are not limited specifically; the M-CSF composition can be prepared in various forms usually used and suited, for example, to oral or nonoral administration. The composition can be provided also as a dry preparation which can be reconstituted to a liquid for use by addition of a suitable excipient. While the amount of the composition to be given in any form is not limited specifically but can be determined suitably according to the desired pharmacological effect, the kind of disease, the age and sex of the patient, the degree of disease, etc., the composition is administered usually at a dose of about 0.001 to about 1 mg/kg/day calculated as the amount of the active component, i.e. M-CSF, in terms of protein amount. The daily dose is given singly or dividedly.

The process for preparing the gene of the invention, the process for preparing M-CSF with use of the gene, the features of the invention, etc. will be described in greater detail with reference to the following examples.

The specimens prepared in these examples were assayed for CSF activity by the following method.

Method of determining CSF activity

Fetal calf serum (FCS, 20 ml), 30 ml of α-medium and 20 ml of α-medium of 2-fold concentration are mixed together, and the solution is then maintained at 37° C. A 23.3-ml portion of the solution is admixed with 10 ml of 1% solution of agar (product of Difco Laboratories) already maintained at 50° C. to obtain an agar medium, which is then maintained at 37° C.

Bone marrow cells (BMC) collected from the femur of a mouse of BALB/c strain are washed with Hank's balanced solution twice and thereafter suspended in α-medium to a concentration of $10^7$ cells/ml, and 1 ml of the suspension is added to the agar medium maintained at 37° C. The mixture is thoroughly stirred and then maintained at 37° C. A 0.5-ml portion of the mixture is placed into wells (Tissue Culture Cluster 12, product of Costar Corporation) already containing 50 µl of a test sample, and the resulting mixture is quickly stirred and then allowed to stand at room temperature. On solidification of the mixture in each well, the wells are placed into a $CO_2$ incubator and incubated at 37° C. for 7 days.

The number of colonies thus produced is counted under an optical microscope to provide an index for the CSF activity. When observed morphologically, the colonies formed were mostly macrophage colonies.

EXAMPLE 1

Preparation of gene of the invention (1) Incubation of AGR-ON cells

Cultured human T cell line AGR-ON (ATCC deposition No. CRL-8199) was suspended to a concentration of about $10^5$ cells/ml in RPMI-1640 medium (product of Flow-Lab. Inc.) containing 10% newborn calf serum (NCS), 20 mM N-2-hydroxyethylpiperazine-N'-2-ethanesulfonic acid (HEPES), 100 µg/ml streptomycin, 100 units/ml of penicillin G, 50 µg/ml of gentamycin, $5 \times 10^{-5}$M 2-mercaptoethanol and 1 mM glutamine. A one-liter portion of the suspension was incubated in five 200-ml tissue culture flasks (product of Corning) at 37° C. for 72 hours.

(2) Extraction of mRNA

About $5 \times 10^8$ AGR-ON cells obtained by the procedure (1) were dissolved in 50 ml of 4M guanidine thiocyanate solution [4M guanidium isothioeyanate, 50 mM Tris-HCl (pH 7.6), 10 mM EDTA, 2% Sarkosyl and 140 mM 2-mercaptoethanol], and while heating the solution at 60° C., the DNA was sheared using 50-ml syringe having 18G injection needle.

To one part by volume of the solution were added 1 part by volume of phenol, 0.5 part by volume of 100 mM sodium acetate (pE 5.2)-10 mM Tris-HCl (pH 7.4)-1 mM EDTA solution, and 1 part by volume of chloroform-isoamyl alcohol (24:1) mixture, as heated to 60° C. The mixture was shaken in a water bath at 60° C. for 10 minutes and then centrifuged at 4° C. at 3,000 r.p.m. for 15 minutes. The aqueous layer was separated off and extracted with phenol-chloroform twice and further with chloroform twice. To the combined extract was added cold ethanol in twice the volume of the extract. The mixture was maintained at −20° C. for 60 minutes and centrifuged at 4° C. at 3,000 r.p.m. for 20 minutes. The RNA precipitate thus obtained was dissolved in 50 ml of 100 mM Tris-HCl (pH 7.4)-50 mM NaCl-10 mM EDTA-0.2% SDS solution, and proteinase K (product of Merck) was added to the solution to a concentration of 200 µg/ml, followed by reaction at 37° C. for 60 minutes. At 60° C., the reaction mixture was extracted with phenol-chloroform twice and further with chloroform twice. To the combined extract were added 3M sodium acetate (pH 5.2) in 1/10 the volume of the extract and cold ethanol in twice the volume thereof. The mixture was allowed to stand at −70° C. for 60 minutes and then centrifuged at 4° C. at 3,000 r.p.m. for 20 minutes. The RNA precipitate was washed with cold 70% ethanol and thereafter dissolved in TE solution (10 mM Tris-HCl (pH 7.5) and 1 mM EDTA).

In this way, about 5 mg of total RNA was obtained from the $5 \times 10^8$ AGR-ON cells.

To obtain mRNA from the total RNA, the RNA was subjected to column chromatography using oligo(dT)-cellulose (Collaborative Research Inc.). For adsorption, 10 mM Tris-HCl (pH 7.5)-1 mM EDTA-0.5M NaCl solution was used. The column was washed with the same solution and with 10 mM Tris-HCl (pH 7.5)-1 mM EDTA-0.1M NaCl solution, and the RNA was then eluted with 10 mM Tris-HCl (pH 7.5)-1 mM EDTA.

The above procedure gave about 110 µg of mRNA.

(3) Preparation of cDNA library cDNA was prepared from a 5-µg portion of the mRNA obtained by the procedure (2), using cDNA Synthesis System (product of Amersham).

The cDNA (about 0.6 µg) obtained was dried in a vacuum and then dissolved in 20 µl of 50 mM Tris-HCl (pH 7.5)-10 mM EDTA-50 mM DTT-40 µM S-adenosyl-L-methionine solution. After addition of 16 units of EcoRI methylase (product of New England Biolab.), the solution was reacted at 37° C. for 15 minutes.

The reaction mixture was heated at 70° C. for 10 minutes to terminate the reaction and then extracted with phenol-chloroform. To the extract were added 3M sodium acetate (pH 5.2) in 1/10 the volume of the extract and ethahol in 2.5 times the volume thereof, and the mixture allowed to stand at −70° C. for 15 minutes. The mixture was centrifuged at 4° C. at 15,000 r.p.m. for 15 minutes, the DNA precipitate was dissolved in 10 µl of 50 mM Tris-HCl (pH 7.5)-10 mM $MgCl_2$-10 mM DTT-1 mM ATP-100 µg/ml of EcoRI linker (5'-GGAATTCC-3', product of Takara Shuzo Co., Ltd., Japan), 350 units of T4DNA ligase (product of Takara Shuzo Co., Ltd.) was added to the solution, and the mixture was reacted at 14° C. for 16 hours.

The reaction mixture obtained was heated at 70° C. for 10 minutes to terminate the reaction. To the mixture were added 16 µl of 100 mM NaCl-50 mM Tris-HCl (pH 7.5)-7 mM $MgCl_2$-10 mM DTT solution and 40 units of the restriction enzyme EcoRI (Takara Shuzo Co., Ltd.), and the mixture was maintained at 37° C. for 3 hours for digestion.

To the reaction mixture was added 0.8 µl of 0.5M EDTA (pH 8.0) to terminate the reaction, and an excess of EcoRI linker was removed by Biogel A50m (product of Bio-Rad Laboratories) column chromatography. To the cDNA fraction was added 1 µg of λgt11DNA (Protoclone GT, Promega Biotec.) digested with the restriction enzyme EcoRI and treated with alkaline phosphatase to remove the 5'-phosphate group. Also added to the fraction were 3M sodium acetate (pH 5.2) in 1/10 the volume of the fraction and ethanol in 2.5 times the volume thereof. The mixture was allowed to stand at −70° C. for 30 minutes and centrifuged at 4° C. at 15,000 r.p.m. for 15 minutes. The DNA precipitate was washed with 70% ethanol, then dried in a vacuum and dissolved in 7 µl of water.

After addition of 2 µl of 500 mM Tris-HCl (pH 7.5)-100 mM $MgCl_2$, the solution was subsequently maintained at 42° C. for 15 minutes and thereafter cooled to room temperature. To the solution were then added 1 µl of 100 mM DTT, 1 µl of 10 mM ATP and 175 units of T4DNA ligase. The mixture was incubated at 14° C. for 16 hours.

To 10 µl of the reaction mixture was added a λ phage packaging extract (Packagene System, Promega Biotec.), and the mixture was maintained at 22° C. for 2 hours, whereby recombinant phage DNA was packaged in vitro. After addition of 0.5 ml of phage dilution buffer (100 mM NaCl-10 mM Tris-HCl (pH 7.9)-10 mM $MgSO_4 \cdot 7H_2O$) and 25 µl of chloroform, the resulting solution was stored at 4° C.

(4) Screening of cDNA library
(4)-1. Preparation of synthetic probe

The following sequence was used for a synthetic probe based on the information of the amino terminal sequence (27 residues) of AGR-ON.CSF purified from an AGR-ON culture supernatant.

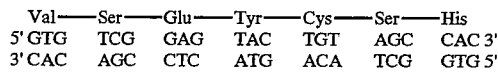

A nucleotide sequence (shown immediate above) complementary to the sequence of the foregoing formula was synthesized by the following procedure in order to use as a probe for selecting a recombinant phage having cDNA coding for M-CSF.

The desired completely protected DNA was synthesized by the solid-phase phosphite triester process (*Nature*, 310, 105 (1984)) wherein an N,N-dialkylmethylphosphoroamidite derivative is used as the condensation unit, using an automatic synthesizer (380A DNA synthesizer, Applied Biosystems Inc.). The completely protected DNA was then treated with 28% of ammonia water at 55° C. for 10 hours, whereby the protective groups (i.e. acyl groups on the amino groups of A, G and C) other than the DMTr (dimethoxytrityl) serving as a protective group and attached to the OH at the 5' terminus were removed to give partially protected DNA (to be referred to as "DMTr unit"). The DMTr unit was then purified by reverse-phase high-performance liquid chromatography (HPLC) using a ODS (product of Yamamura Kagaku Kenkyusho Co., Ltd., Japan) column and thereafter treated with 80% acetic acid at room temperature for 20 minutes to obtain a crude oligonucleotide. The product was further purified by reverse-phase HPLC with the ODS column to prepare the desired oligonucleotide.

The DNA (0.8 µg) obtained was reacted with 18 units of T4 polynucleotide kinase (Takara Shuzo Co., Ltd.) at 37° C. for 1 hour in 100 µl of a reaction medium (50 mM Tris-HCl (pH 7.6), 10 mM MgCl$_2$, 10 mM 2-mercaptoethanol, 200 µCi[γ-$^{32}$P]-ATP) to label the 5' end of the DNA with $^{32}$P. To separate the labeled DNA from the unreacted [γ-$^{32}$P]ATP, the reaction mixture was subjected to gel filtration using Biogel P-30 (Bio-Rad Laboratories). The labeled DNA fractions were pooled and preserved at –20° C. The probe obtained was at least 10$^8$ cpm/µg DNA in specific radioactivity.

(4)-2 Plaque hybridization

*E. coli* Y1090 strain was inoculated in 40 ml of LB medium (10 g/l of Bacto-tryptone, 5 g/l of Bacto-yeast extract and 5 g/l of NaCl) containing 50 µg/ml of ampicillin and 0.2% of maltose and incubated with shaking in a 300-ml flask overnight at 37° C. The culture was centrifuged at 4° C. at 3,000 r.p.m. for 15 minutes to collect cells. The cell pellets were suspended in 20 ml of SM medium (100 mM NaCl-50 mM Tris-HCl (pH 7.5)-10mM MgSO$_4$.7H$_2$O-0.01% gelatin) and stored at 4° C.

To a 0.3 ml portion of the cell suspension was added 0.1 ml of the recombinant phage solution which was obtained by the procedure (3) and diluted to 3.5×10$^5$ pfu (plaque forming units)/ml with SM medium, and the mixture was then incubated at 37° C. for 15 minutes. Subsequently, LB soft agar medium (10 g of Bacto-tryptone, 5 g of Bacto-yeast extract, 5 g of NaCl and 7 g/liter of agarose) prewarmed to 47° C. was admixed with the mixture, and the resulting mixture was overlayered onto LB agar plate (10 g of Bacto-tryptone, 5 g of Bacto-yeast extract, 5 g of NaCl and 15 g/liter of Bacto-agar), and incubated at 42° C. overnight. Same procedure was repeated in each of 20 petri dishes.

A nylon filter (BNRG 132, Pall Ultrafine Filtration Corp.) having a diameter of 132 mm was placed over each agar plate having a plaque formed thereon to prepare a replica filter. The agar plate was preserved at 4° C. as a master plate.

The filter was treated with 0.5M NaOH-1.5M NaCl, then with 0.5M Tris-HCl (pH 7.5)-1.5M NaCl and thereafter with 0.3M NaCl-0.02M NaH$_2$PO$_4$ (pH 7.4)-0.002M EDTA (pH 7.4), dried in air and baked under vacuum at 80° C. for 1 hour.

The baked filter was maintained with gentle shaking at 42° C. for 6 hours in 50 ml of 0.75M NACl-0.075M sodium citrate-1.0 mg/ml of Ficoll-1.0 mg/ml of polyvinylpyrrolidone-1.0 mg/ml BSA-10 mM sodium phosphate (pH 6.5)-0.2% SDS-0.1 mg/ml salmon sperm DNA. Subsequently, the filter was placed into the same solution as above having the probe added thereto at a concentration of 10$^6$ cpm/ml and hybridized at 42° C. for 20 hours with gentle shaking.

After the hybridization, the filter was withdrawn from the solution, washed with 0.9M NaCl-0.09M sodium citrate at room temperature three times and then with the same solution at 56° C. for 5 minutes.

The filter was dried in air and thereafter autoradiographed at –70° C. for 2 days on an X-ray film (XR5, Eastman Kodak Co.) using intensifying screen.

After developing the film, the plaques corresponding to the signal region were scraped off the master plate, and the above procedure is repeated to purify the plagues having a positive signal, whereby positive clone λcM5 and λcM11 were eventually isolated.

(5) Structural analysis of the cDNA clone

Restriction enzyme analysis of λcM5 was carried out, and the result is shown in FIG. 1.

As shown in FIG. 1, the cDNA is about 2.5 kb in entire length and has sites of cleavage by BstEII (product of New England Biolab.), NcoI (product of Takara Shuzo Co., ltd.), SmaI (Takara), KpnI (Takara), EcoRI (Takara) and NdeI (product of New England Biolab.), one cleavage site for each, and two sites of cleavage by each of ScaI, StuI and BamHI (all products of Takara).

Next, the nucleotide sequence of the cDNA was determined by the Maxam-Gilbert chemical modification method and the dideoxynucleotide chain termination method using M13 phage. FIG. 2 (FIGS. 2-1 to 2-4) shows the result.

FIG. 2 reveals that the region (shown as underlined) of the 227th to the 247th bases from the 5' terminus is complementary to the synthetic probe.

When the cDNA of λcM5 is searched for the longest reading frame, the region of the 125th to the 1240th bases from the 5' terminus was found to be this frame. The amino acid sequence corresponding to the sequence of the 227th to 307th bases and coded by the codons thereof was completely in match with the 27 amino acids at the N terminal region of AGR-ON.CSF. This indicates that the cDNA of λcM5 is the cDNA coding for an M-CSF precursor protein.

FIG. 3 (FIGS. 3-1 and 3-2) shows the primary structure of the M-CSF precursor protein predicted from these results.

FIG. 4 (FIGS. 4-1 to 4-4) shows the nucleotide sequence of the cDNA of λcM11 determined in the same manner as above and coding for an M-CSF precursor protein, the predicted primary structure of which is shown in FIG. 5 (FIGS. 5-1 to 5-3).

EXAMPLE 2

Preparation of recombinant M-CSF (r-MCSF)
(1) Preparation of COS cell expression vector pcDE COS-1 cell used in this example is a cell line which is obtained by transforming monkey renal cell line, CV1, with replication origin (Ori)-deficient SV40, and thereby made to express SV40 early gene and rendered T antigen positive (*Cell*, 23, 175–182 (1981)).

Plasmid pcDV1 (H. Okayama and P. Berg, *Mol. Cell. Biol.*, 3, 280–289 (1983)) was first cleaved with restriction enzyme KpnI, and the protruding 3' end was converted to blunt end by T4 DNA polymerase (product of BRL).

On the other hand, the 5' end of EcoRI linker (5'-GGAATTCC-3') (product of Takara Shuzo Co., Ltd.) was phosphorylated with T4 polynucleotide kinase and ligated to the blunt-ended DNA fragment using T4 DNA ligase. The resultant ligate is cleaved with restriction enzyme EcoRI and further with restriction enzyme HindIII. The reaction product obtained was subjected to agarose gel electrophoresis, whereby EcoRI-HindIII DNA fragment of 2590 bp was isolated and purified.

Plasmid pL1 (H. Okayama and P. Berg, *Mol. Cell. Biol.*, 3, 280–289 (1983)) was cleaved with restriction enzyme PstI (product of Takara Shuzo Co., Ltd.) and the protruding 3' end was converted to blunt end using T4 DNA polymerase. In the same manner as above, EcoRI linker was ligated to the DNA fragment, the resulting DNA fragment was cleaved with restriction enzyme HindIII, and the reaction product was subjected to agarose gel electrophoresis, whereby EcoRI-HindIII DNA fragment with 580 bp was isolated and purified.

The DNA fragment obtained was ligated to the EcoRI-HindIII DNA fragment previously prepared, using T4 DNA ligase, to afford the desired plasmid pcDE.

Figure 6:
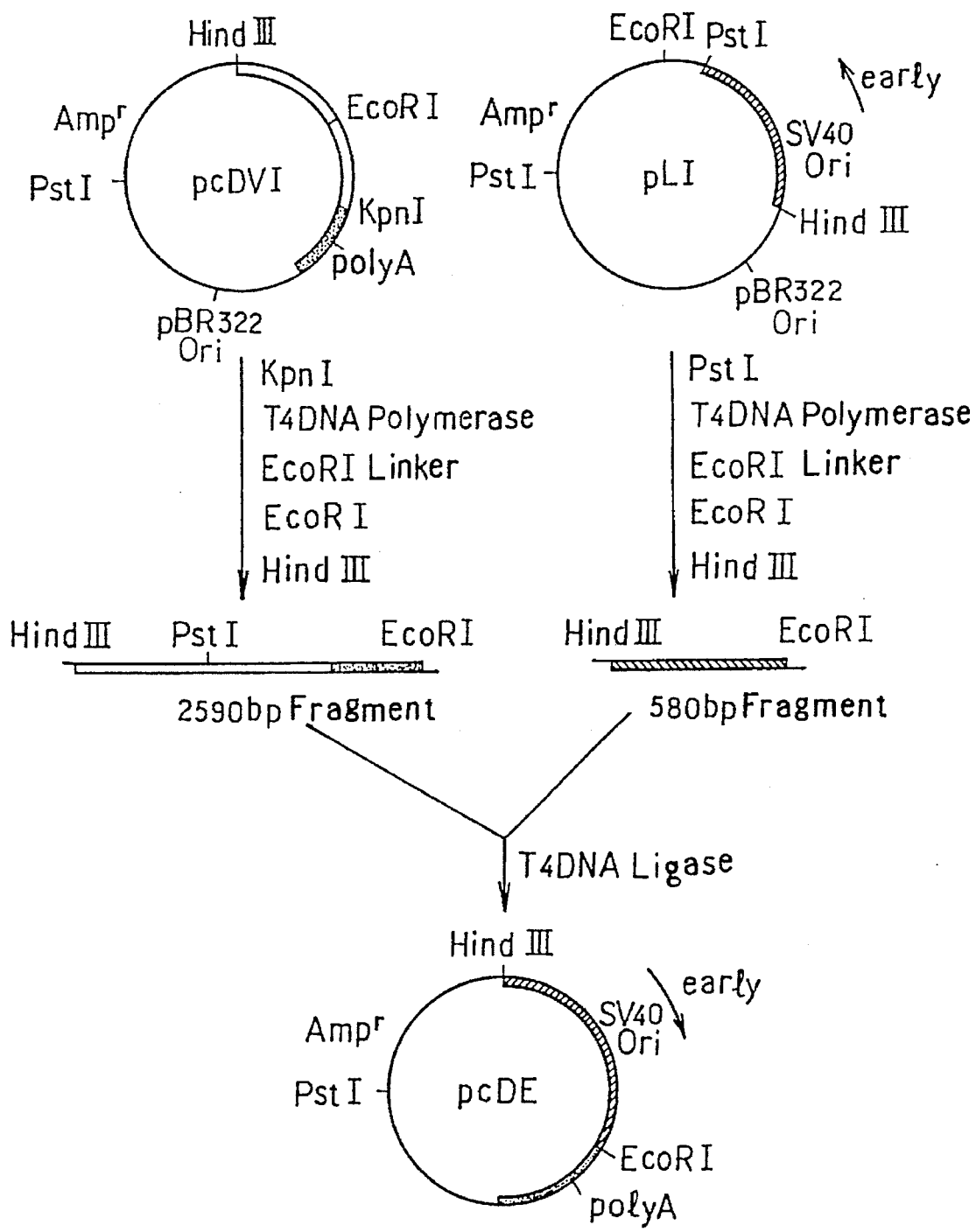
FIG. 6 is a diagram showing a procedure for preparing COS cell expression vector pcDE.

FIG. 6 schematically shows the above procedure.

(2) Preparation of M-CSF expression plasmid pcDM.CSF

λcM5 DNA was partially digested with restriction enzyme EcoRI, and size-fractionated on agarose gel to isolate and purify a cDNA fragment (about 2.5 kb) as a partially digested EcoRI fragment.

The COS cell expression vector pcDE obtained by the procedure (1) was cleaved with restriction enzyme EcoRI and ligated to the cDNA fragment prepared above, using T4 DNA ligase, whereby the desired plasmid pcDM.CSF was obtained.

The plasmid thus obtained was introduced into *E. coli* HB101 strain. The desired transformant was selected by the restriction enzyme analysis of the plasmid DNA obtained according to the alkaline lysis method (T. Maniatis et al., Molecular Cloning, pp. 90, Cold Spring Harbor Laboratory (1982)).

Figure 7:
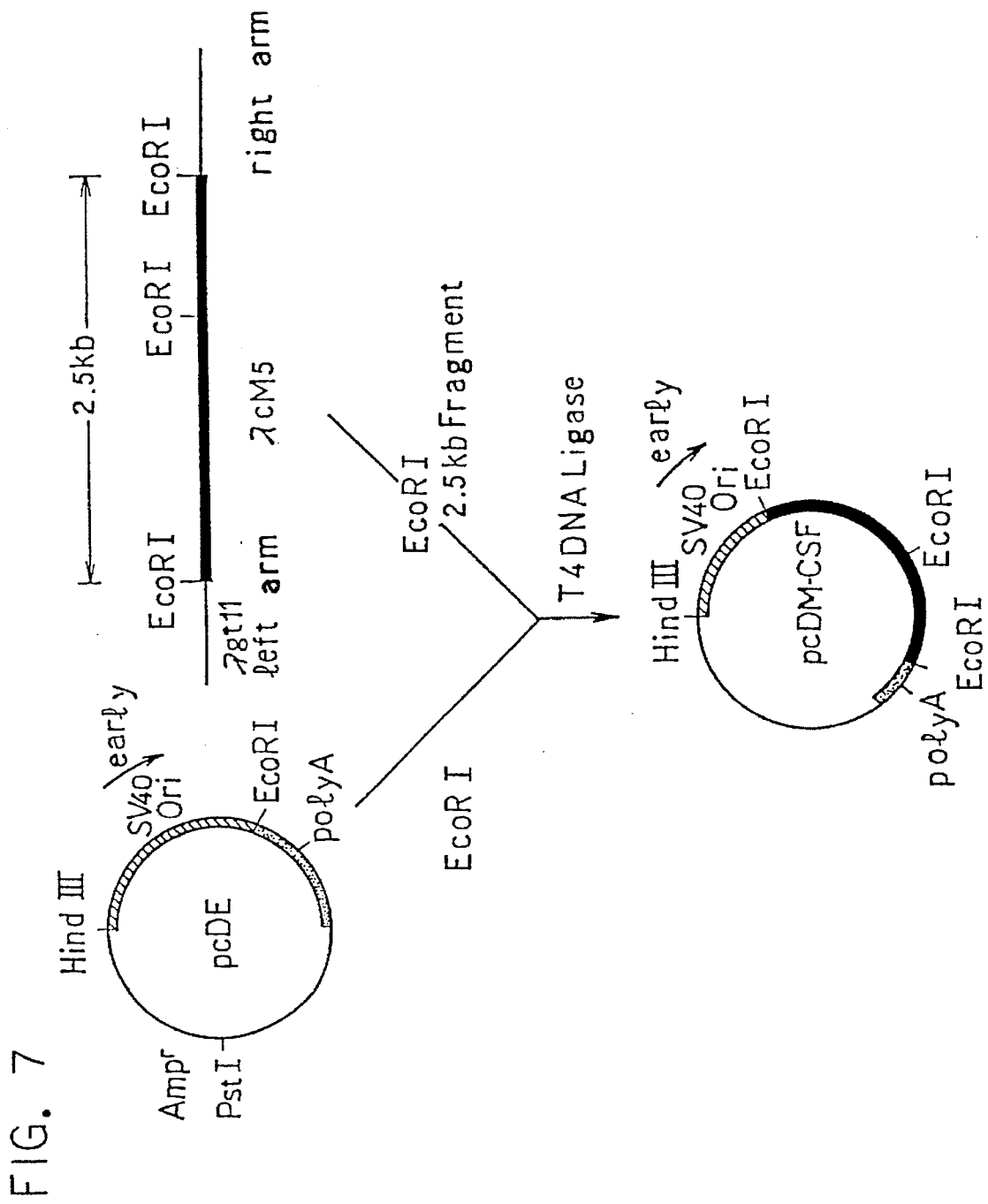
FIG. 7 is a diagram showing a procedure for preparing M-CSF expression plasmid pcDM.CSF.

FIG. 7 schematically shows the above procedure.

(3) Preparation of r-MCSF

COS-1 cells were transfected with the pcDM.CSF prepared by the procedure (2), by the DEAE-dextran method (*Proc. Natl. Acad. Sci. U.S.A.*, Vol. 81, p1070 (1984)) and tested for the production of r-MCSF by the following procedure.

COS-1 cells were first suspended to a concentration of about $2.5 \times 10^5$ cells/ml in RPMI-1640 medium supplemented with 10% fetal calf serum (FCS). The suspension was placed into Tissue Culture Cluster-6 (product of Costar Corp.) in an amount of 2 ml in each well and incubated overnight at 37° C. in a $CO_2$ incubator.

Subsequently, the medium was removed, the cells were washed with RPMI-1640 medium twice, 1 ml of RPMI-1640 (containing 50 mM Tris-HCl (pH 7.4) and 400 µg/ml DEAE-dextran (Pharmacia)) containing 10 µg of pcDM.CSF obtained by the procedure (2) was then added to the cells, and the mixture was allowed to stand in a $CO_2$ incubator for 4 hours. After removing the medium, the cells were washed twice with RPMI-1640 medium and then incubated for 3 hours with addition of 3 ml of RPMI-1640 medium containing 150 µM chloroquine (Sigma Chemical Company). The medium was subsequently removed, and the cells were washed with RPMI-1640 medium and thereafter incubated in 10% FCS-containing RPMI-1640 medium at 37° C. for 72 hours in a $CO_2$ incubator.

The culture supernatant and the extract therefrom were assayed for CSF activity at each dilution ratio.

The results are given in Table 1 below, which also shows the results achieved by the same procedure as above using pcDE as a control in place of pcDM.CSF. The assay was conducted in duplicate.

TABLE 1

| Dilution ratio | 16 | 32 | 64 | 128 |
| --- | --- | --- | --- | --- |
| pcDM.CSF | | | | |
| Supernatant | 282 | 274 | 159 | 79 |
| Extract | 97 | 41 | 0 | 0 |
| pcDE (Control) | | | | |
| Supernatant | 0 | 0 | 0 | 0 |
| Extract | 0 | 0 | 0 | 0 |

Each value listed in Table 1 is the number of colonies per plate, the same as in the tables to follow showing the CSF activity.

(4) Preparation of M-CSF expression plasmid pcDM.CSF-185

Using the plasmid pcDM.CSF obtained by the procedure (2), the desired M-CSF expression plasmid pcDM.CSF-185 was prepared according to the site-specific mutagenesis method (*Proc. Natl. Acad. Sci.*, 81, 5662–5666 (1984)) by replacing the codon (AAG) coding for the 186th amino acid (Lys) in FIG. 3 by an termination codon (TAG), the expression plasmid therefore having the 185th amino acid (Thr) in FIG. 3 at its C terminus.

This procedure will be described in detail below.

EcoRI-EcoRI DNA fragment (1.8 kb in size) was excised from plasmid pcDM.CSF and cloned in M13mp11 phage (RF) at EcoRI sites to thereby obtain a single-stranded (ss) DNA (M13-CSF), which was used as a template for mutagenesis.

On the other hand, synthetic oligonucleotide [5'-GTGGTGACCTAGCCTGATT-3' (primer)] was phosphorylated with T4 polynucleotide kinase and then hybridized with the ssDNA (M13-CSF). After annealing, the hybrid was treated with DNA polymerase I (Klenow fragment) and T4 DNA ligase in the presence of dNTP and incubated at 15° C. for 18 hours.

The resulting DNA was introduced into JM105 competent cells, and 50 plaques among the plaques formed were inoculated on agar plate and incubated at 37° C. for 18 hours. A filter containing the colonies was alkaline-denatured in a usual manner, dried and thereafter baked at 80° C. for 2 hours. The filter was prehybridized and thereafter hybridized with $^{32}P$-probe prepared by labeling the 5' end of the above primer with $[\gamma-^{32}P]ATP$ at room temperature. The hybridized filter was washed with 6 x SSC (saline sodium citrate) first at room temperature for 10 minutes and then at 56° C. for 4 minutes, dried and thereafter subjected to autoradiography at −70° C. for 18 hours.

M13-CSF-185 was selected from among the mutant clones and transfected to JM105 to prepare ssDNA and RF DNA.

The exactness of the mutated sequence was confirmed by sequencing the ssDNA by the dideoxynucleotide chain termination method.

The desired plasmid pcDM.CSF-185 was obtained by preparing EcoRI-EcoRI fragment from the RF DNA amplified in the JM105 and inserting the fragment into an expression plasmid in the same manner as in the procedure (3).

Using this plasmid, COS-1 cells were caused to express r-MCSF in the same manner as in the procedure (3). Table 2 below shows the results.

TABLE 2

| Dilution ratio | 1 | 3 | 9 | 27 | 81 |
|---|---|---|---|---|---|
| pcDM.CSF-185 Supernatant | 288 | 243 | 238 | 173 | 90 |

(5) Preparation of M-CSF expression plasmid pcDM.CSF-177

Using 5'-GCTGAATGATCCAGCCAA-3' as a primer, the desired M-CSF expression plasmid pcDM.CSF-177 was prepared in the same manner as in the procedure (4) by replacing the codon (TGC) coding for the 178th amino acid (Cys) in FIG. 3 by a termination codon (TGA), the expression plasmid therefore having the 177th amino acid (Glu) in FIG. 3 at its C terminus.

Using this plasmid, COS-1 cells were caused to express r-MCSF in the same manner as in the procedure (3). Table 3 below shows the results.

TABLE 3

| Dilution ratio | 1 | 3 | 9 | 27 | 81 |
|---|---|---|---|---|---|
| pcDM.CSF-177 Supernatant | 249 | 254 | 166 | 83 | 28 |

The results given in Tables 2 and 3 reveal that the desired r-MCSF having M-CSF activity can be expressed by the use of plasmids pcDM.CSF-185 and pcDM.CSF-177 having the gene of the invention.

This indicates that the portion of the amino acid sequence shown in FIG. 3 from the 178th amino acid to the amino acid at the C terminus exerts substantially no influence on the expression of M-CSF molecules having the desired biological activity.

(6) Preparation of M-CSF expression plasmid pcDM.CSF11

Plasmid pcDM.CSF11 was obtained by the procedure (2) using λcM11cDNA in place of λcM5cDNA. r-MCSF was prepared by the procedure (3) with use of the plasmid, achieving substantially the same results as previously attained.

More specifically stated, λcM11 DNA was partially digested with restriction enzyme EcoRI, subjected to agarose gel electrophoresis, and the cDNA fragment (about 2.5 kb) was purified as partially digested EcoRI fragment.

The COS cell expression vector pcDE obtained by the procedure (1) was cleaved with restriction enzyme EcoRI and ligated to the cDNA fragment prepared above, using T4 DNA ligase, whereby the desired plasmid pcDM.CSF11 was obtained.

The plasmid thus obtained was introduced into *E. coli* HB101 strain. The desired transformant was selected by the restriction enzyme analysis of it's plasmid DNA according to the alkaline lysis method (T. Manjarls et al., Molecular Cloning, pp 90, Cold Spring Harbor Laboratory (1982)).

Further the cDNA (fragment partially digested with EcoRI) of the λcM11 DNA was inserted into cloning vector pUC19 DNA (product of Takara Shuzo Co., Ltd.) at EcoRI cloning site, giving plasmid pUC MCSF.11. The transformant obtained by introducing the plasmid into *E.*

*coli* HB101 strain has been deposited under the name of *Escherichia coli* HB101/pUC MCSF.11 with deposition number FERM BP-1409 in Fermentation Research Institute Agency of Industrial Science & Technology since Jul. 16, 1987.

(7) Preparation of M-CSF expression plasmid pcDM.CSF11-185

Plasmid pcDM CSF11 was digested with restriction enzymes EcoRI and BstEII to isolate and purify EcoRI-BstEII DNA fragment of about 670 bp.

To the BstEII end of the DNA fragment was ligated a synthetic linker,

The resultant DNA fragment was then ligated to the above-mentioned plasmid pcDE digested with EcoRI, using T4 DNA ligase to obtain the desired plasmid pcDM.CSF11-185. This plasmid has translation termination codon TGATAA at the site of the synthetic linker and therefore codes for a polypeptide having the 185th amino acid (Thr) in FIG. 5 at its C terminus.

Figure 8:
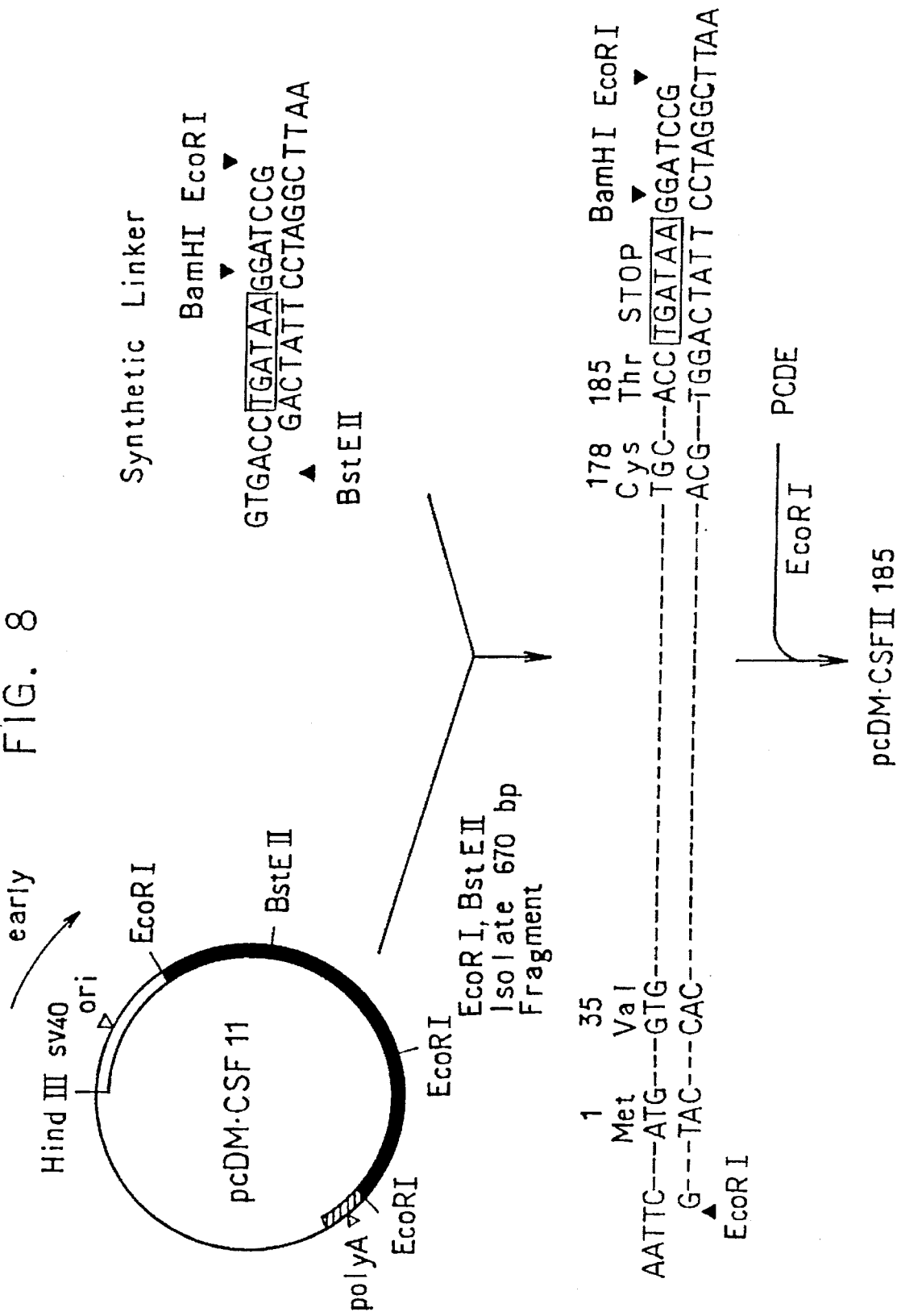
FIG. 8 is a diagram showing a procedure for preparing M-CSF expression plasmid pcDM.CSF11-185.

FIG. 8 schematically shows the above process.

Table 4 shows the result achieved in the same manner as in the procedure (3) using the plasmid.

TABLE 4

| Dilution ratio | 1 | 2 | 4 | 8 |
|---|---|---|---|---|
| pcDM.CSF11-185 Supernatant | >200 | >200 | 191 | 171 |
| Dilution ratio | 16 | 32 | 64 | |
| pcDM.CSF11-185 Supernatant | 110 | 84 | 60 | |

(8) Preparation of M-CSF expression plasmid pcDM.CSF11-177

Using the plasmid pcDM.CSF11-185 obtained by the procedure (7), the desired M-CSF expression plasmid pcDM.CSF11-177 was prepared by replacing the codon (TGC) coding for the 178th amino acid (Cys) in FIG. 5 by a termination codon (TGA) according to the procedure (5), the expression plasmid thus having the 177th amino acid (Glu) in FIG. 5 at its C terminus. The plasmid was used for expression in the same manner as in the procedure (3), with the result shown in Table 5 below.

TABLE 5

| Dilution ratio | 1 | 2 | 4 | 8 | 16 |
|---|---|---|---|---|---|
| pcDM.CSF11-177 Supernatant | 192 | >200 | >200 | 180 | 70 |

(9) Preparation of M-CSF expression plasmid pcDM.CSF11-163

In the same manner as the procedure (4) and using the plasmid pcDM.CSF11-185 obtained by the procedure (7) and 5'-AAGGACTGAAATATTTTC-3' as a primer, the desired M-CSF expression plasmid pcDM.CSF11-163 was prepared by replacing the codon (TGG) coding for the 164th amino acid in FIG. 5 by a termination codon (TGA), the expression plasmid having the 163rd amino acid (Asp) in FIG. 5 at its C terminus.

In the same manner as the procedure (3), the plasmid was caused to express r-MCSF in COS-1 cells. The CSF activity of the resulting supernatant was 12 colonies/plate.

The result indicates that at least the amino acid sequence from the 164th amino acid to the C terminus in the amino acid sequence of the formula (1) exerts no substantial influence on the expression of M-CSF molecules having the desired biological activity.

(10) Preparation of M-CSF secretory expression plasmid pIN-III(lpp$^P$-5)-OmpA-MCSF11-NV151

Plasmid pcDM.CSF11-185 DNA was digested with EcoRI and BamHI to isolate and purify EcoRI-BamHI DNA fragment (about 680 bp), which was inserted into the EcoRI-BamHI cloning site of secretory expression vector pIN-III-OmpA3 (EMBO J., 3, 2437–2442(1984)) to obtain plasmid pIN-III-OmpA3-MCSF11-185.

The plasmid DNA was digested with XbaI and BamHI to isolate and purify XbaI-BamHI DNA fragment (about 770 bp), which was then inserted into the XbaI-BamHI cloning site of cloning vector pUC118 DNA (product of Takara Shuzo Co., Ltd.) for preparing a single-stranded DNA, whereby plasmid pUC118-OmpA3-MCSF11-185 was obtained.

Using the plasmid, plasmid pUC118-OmpA-MCSF11-NV151 was obtained by such modification in which the codon (GTG) coding for the 35th amino acid (Val) of the polypeptide shown in FIG. 5 can follow the codon (GCC) coding for the C-terminal amino acid (Ala) of OmpA signal peptide, according to the aforementioned method of site-specific mutagenesis.

Stated more specifically, E. coli JM105 transformed by plasmid pUC118-OmpA3-MCSF11-185 DNA was infected with helper phage K07 (product of Takara Shuzo Co., Ltd.), followed by incubation at 37° C. for 14 hours, to obtain single-stranded (ss) pUC118-OmpA3-MCSF11-185DNA. With use of this DNA as a template for mutagenesis and also using 5'-TACCGTAGCGCAGGCCGTGTCGGAGTACT GTAGC-3' as a primer, the desired plasmid pUC118-OmpA-MCSF11-NV151 was obtained in the same manner as in the procedure (4).

The plasmid DNA was then digested with XbaI and BamHI to isolate and purify XbaI-BamHI DNA fragment (about 540 bp). The DNA fragment thus obtained was inserted into the XbaI-BamHI site of expression vector pIN-III(lpp$^P$-5)-A3 (Nucl. Acids Res., 13, 3101–3110 (1985)), whereby the desired secretory expression plasmid pIN-III(lpp$^P$-5)-OmpA-MCSF11-NV151 was prepared for expressing a polypeptide comprising the portion of the sequence shown in FIG. 5 from the 35th amino acid (Val) to the 185th amino acid (Thr).

FIGS. 9-1 to 9-3 schematically show the above process. FIG. 10 shows the amino acid sequence encoded in the secretory expression plasmid. In FIG. 10, the underlined portion of the sequence represents the OmpA signal peptide, while the processing site is marked with ↓.

(11) Secretory expression of M-CSF

The pIN-III(lpp$^P$-5)-OmpA-MCSF11-NV151 obtained by the procedure (10) was introduced into E. coli HB101 and JM109 for the secretory production of the polypeptide into the periplasm and the periplasmic fraction having CSF activity was collected.

More specifically stated, the strain harboring the M-CSF secretory expression vector was incubated with shaking in 500 ml of LB medium containing 50 µg/ml of ampicillin at 37° C. for 14 hours within a 2-liter flask, followed by centrifugation at room temperature at 5,000 r.p.m. for 5 minutes. The cell pellets were suspended in 50 ml of 50 mM Tris-HCl (pH 8.0)-25% sucrose solution, and after addition of 1.25 ml of 250 mM EDTA (pH 8.0), the suspension was maintained at room temperature for 30 minutes with gentle shaking. The suspension was then centrifuged to obtain cell pellets, which were suspended again in 25 ml of ice-cold distilled water. The suspension was cooled in ice for 30 minutes with intermittent gentle shaking and thereafter centrifuged at 4° C. at 10,000 r.p.m. for 5 minutes to collect a supernatant as the periplasmic fraction.

(12) Preparation of M-CSF secretory expression plasmid, pIN-III(lpp$^P$-5)-OmpA-MCSF11-NV143

The desired M-CSF secretory expression plasmid, pIN-III(lpp$^P$-5)-OmpA-MCSF11-NV143, was obtained for expressing a polypeptide comprising the portion of the sequence shown in FIG. 5 from the 35th amino acid (Val) to the 177th amino acid (Glu), by the procedure (10) using pcDM.CSF11-177 in place of pcDM.CSF11-185.

FIG. 11 shows the amino acid sequence encoded in the plasmid. In FIG. 11, the underlined portion of the sequence represents OmpA signal peptide, and the mark ↓ indicates the processing site. In the same manner as in the procedure (11), the plasmid was introduced into E. coli, from which a supernatant exhibiting CSF activity was obtained as a periplasmic fraction.

(13) HPLC of M-CSF

The supernatants obtained by the procedures (6), (7), (8) and (11) were subjected to HPLC under the following conditions.

Column: TSK Gel G3000SW (60 cm×7.5 mm(diam.), Tosoh Corporation

Eluent: PBS$^-$-containing 0.005% polyethylene glycol and 0.15M NaCl.

Flow rate: 0.8 ml/min.

Fraction volume: 0.8 ml/tube/min.

The following results were obtained for the samples with reference to molecular weight markers (glutamate dehydrogenase: 290,000, lactate dehydrogenase: 142,000, enolase: 67,000, adenylate kinase: 32,000, cytochrome C: 12,400).

Sample: Four ml of the culture supernatant obtained by the procedure (6) was concentrated to about 150 µl by Centricon-10 (product of Amicon)

CSF activity was found in a fraction corresponding to 320,000 to 700,000 in molecular weight range (480,000 on the average).

Sample: Four ml of the culture supernatant obtained by the procedure (7) was treated in the same manner as above.

CSF activity was found in a fraction corresponding to 66,000 to 86,000 in molecular weight range (76,000 on the average).

Sample: Four ml of the culture supernatant obtained by the procedure (8) was treated in the same manner as above.

CSF activity was found in a fraction corresponding to 52,000 to 86,000 in molecular weight range (67,000 on the average).

Sample: Two ml of the supernatant of periplasmic fraction obtained by the procedure (11) was concentrated to about 110 µl in the same manner as above.

CSF activity was found at a position corresponding to about 30,000 to 40,000 in molecular weight range (35,000 on the average).

(14) SDS-PAGE of M-CSF

Ten ml of the culture supernatant obtained by the procedure (6), (7) or (8) was passed through a column packed with 1 ml of ConA-Sepharose, which was then washed with 5 ml of PBS$^-$ and eluted with PBS$^-$ (10 ml) containing 0.5M methyl-α-D-mannoside. A 4-ml portion of the resulting eluate was concentrated with Centricon-10, and the concentrate was used for SDS-PAGE mentioned below.

The periplasmic supernatant as obtained by the procedure (11) was used as another sample therefor.

M-CSF was detected by using a rabbit anti-serum against M-CSF prepared in the conventional manner, after Western blotting of the SDS-PAGE gels.

More specifically, SDS-PAGE was carried out according to the method of Laemmli, U. K. (Nature, 277, 680 (1970)) using a mini-vertical slab cell (gel concentration 15%). Western blotting was conducted using Transblot Cell (product of Bio-Rad Laboratories). The nitrocellulose filter having the desired substance transferred thereto, was blocked with PBS⁻ containing 1% bovine serum albumin and then reacted with the rabbit anti-serum against M-CSF first and further with peroxidase-labeled goat anti-rabbit antibody (product of Bio-Rad Laboratories). The resulting nitrocellulose filter was reacted with 4-chloro-1-naphthol solution serving as a color developing substrate for the detection of M-CSF band. Table 6 shows the results.

TABLE 6

| Sample | Molecular weight of detectd band (kd) | |
|---|---|---|
| | Non-reducing condition | Reducing condition |
| Supernatant Obtained by (6) | 82 | 43.5 |
| | 150 | 58 |
| | At least 200 (in stacking gel) | At least 70 (plural) |
| Supernatant obtained by (7) | 40 (faint) | 15 (faint) |
| | 43 | 20.5 |
| | 45 | 26 |
| | 47 | |
| Supernatant obtained by (8) | 44 | 19 (faint) |
| | 46 | 25 |
| | 50 | |
| Supernatant obtained by (11) | 32 | 17 |

(15) Preparation of M-CSF expression plasmid pcDM.CSF11-dhfr

Plasmid pSV2-dhfr (Mol. Cell. Biol., 1, 854 (1981)) was cleaved into two fragments with restriction enzymes HindIII and BamHI, and the fragment containing a dihydrofolate reductase (DHFR) gene was isolated and purified.

Next, plasmid pRSV-CAT (Proc. Natl. Acad. Sci. U.S.A., 79, 6777(1981)) was similarly cleaved with HindIII and BamHI, and the fragment containing the LTR (long terminal repeat) portion of Rous sarcoma virus (RSV) was isolated and purified. The two purified fragments were ligated together using T4 DNA ligase.

E. coli HB101 competent cells were transformed by adding the above ligated product. Plasmid DNAs were prepared from ampicillin-resistant colonies and were digested with restriction enzymes. The desired plasmid pRSV-dhfr which showed the predicted restriction enzyme map was obtained.

This plasmid contains the LTR portion of RSV, DHFR gene, intervening sequence and polyadenylation signal derived from SV40, and further a replication origin and ampicillin-resistant gene derived from E. coli plasmid pBR322, and expresses DHFR under the control of a promotor contained in the LTR portion.

The plasmid pRSV-dhfr was cleaved into two fragments with NdeI and BamHI, and the fragment containing the DHFR gene was isolated and purified. The DNA fragment obtained was treated with DNA polymerase I (Klenow fragment) to convert the cohesive ends to blunt ends.

On the other hand, the plasmid pcDM.CSF11 obtained by the procedure (6) was cleaved with SalI, and the cleaved ends were similarly converted to the blunt ends by treatment with DNA polymerase I.

The two fragments obtained were ligated together with T4 DNA ligase, and the ligated product was transformed to E. coli JM-109 competent cells. Plasmid DNAs were prepared from the ampicillin-resistant colonies obtained, restriction enzyme maps prepared, and the desired pcDM.CSF11-dhfr for expressing both M-CSF and DHFR genes was obtained.

This plasmid contains the following sequences: with respect to M-CSF gene expression, SV40 early promoter (SV40 early), SV40-derived intervening sequence (SV40 intron), M-CSF gene and polyadenylation signal (SV40 polyA), and also with respect to DHFR gene expression, RSV-derived LTR (RSV-LTR), DHFR gene (dhfr), SV40-derived intervening sequence (SV40 intron) and polyadenylation signal (SV40 polyA). The plasmid further contains a replication origin (Ori) and ampicillin-resistant gene (Amp$^r$) derived from E. coli plasmid pBR322. The transformant obtained by introducing the plasmid into E. coli HB101 strain has been deposited under the name of Escherichia coli HB101/pcDM-CSF11-dhfr with deposition number FERM BP-2224 in Fermentation Research Institute, Agency of Industrial Science & Technology since Dec. 26, 1988.

Figure 12:
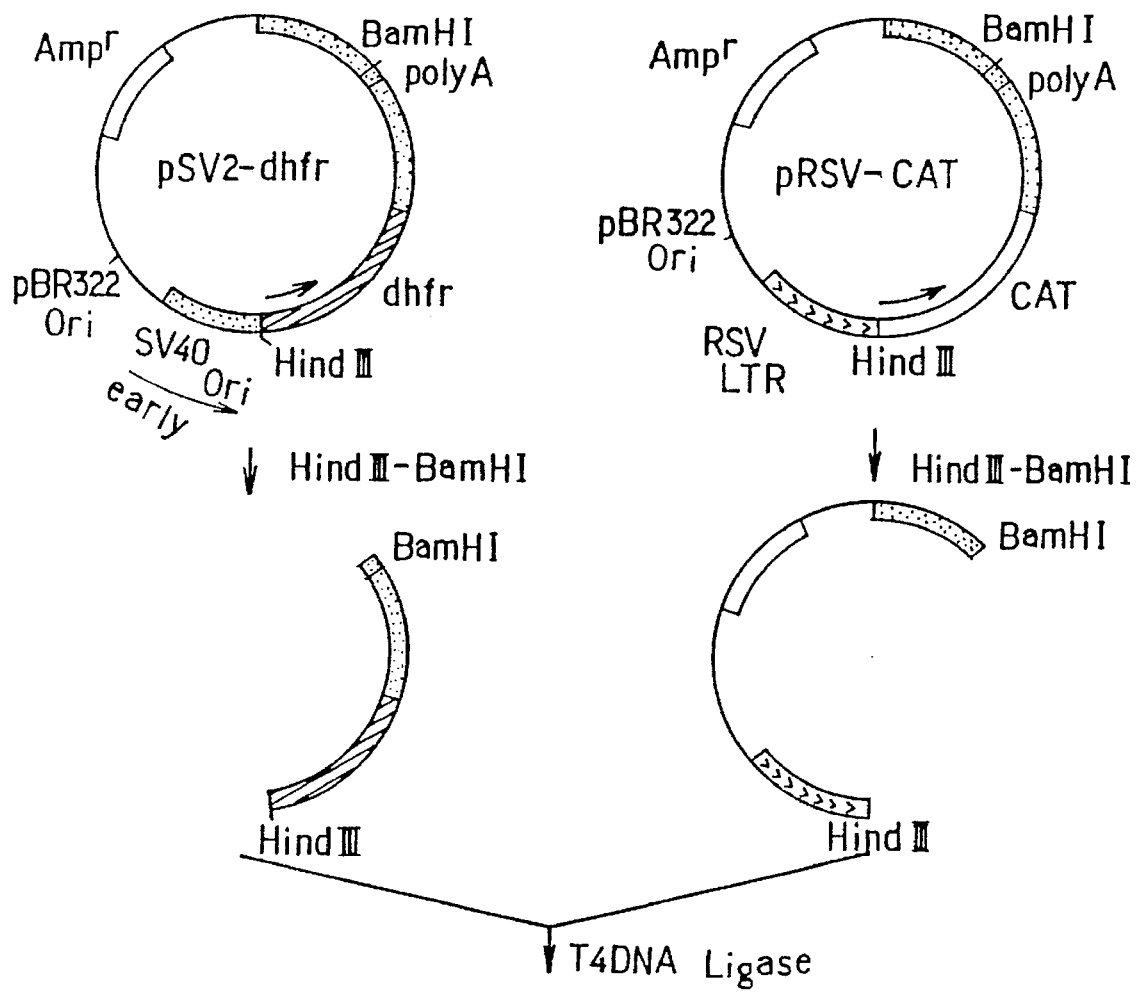
Figure 1:
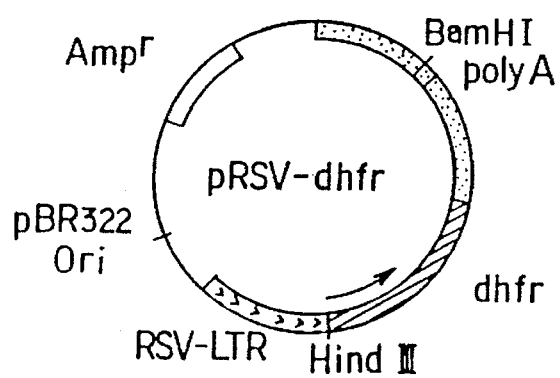
Figures 2, 12:
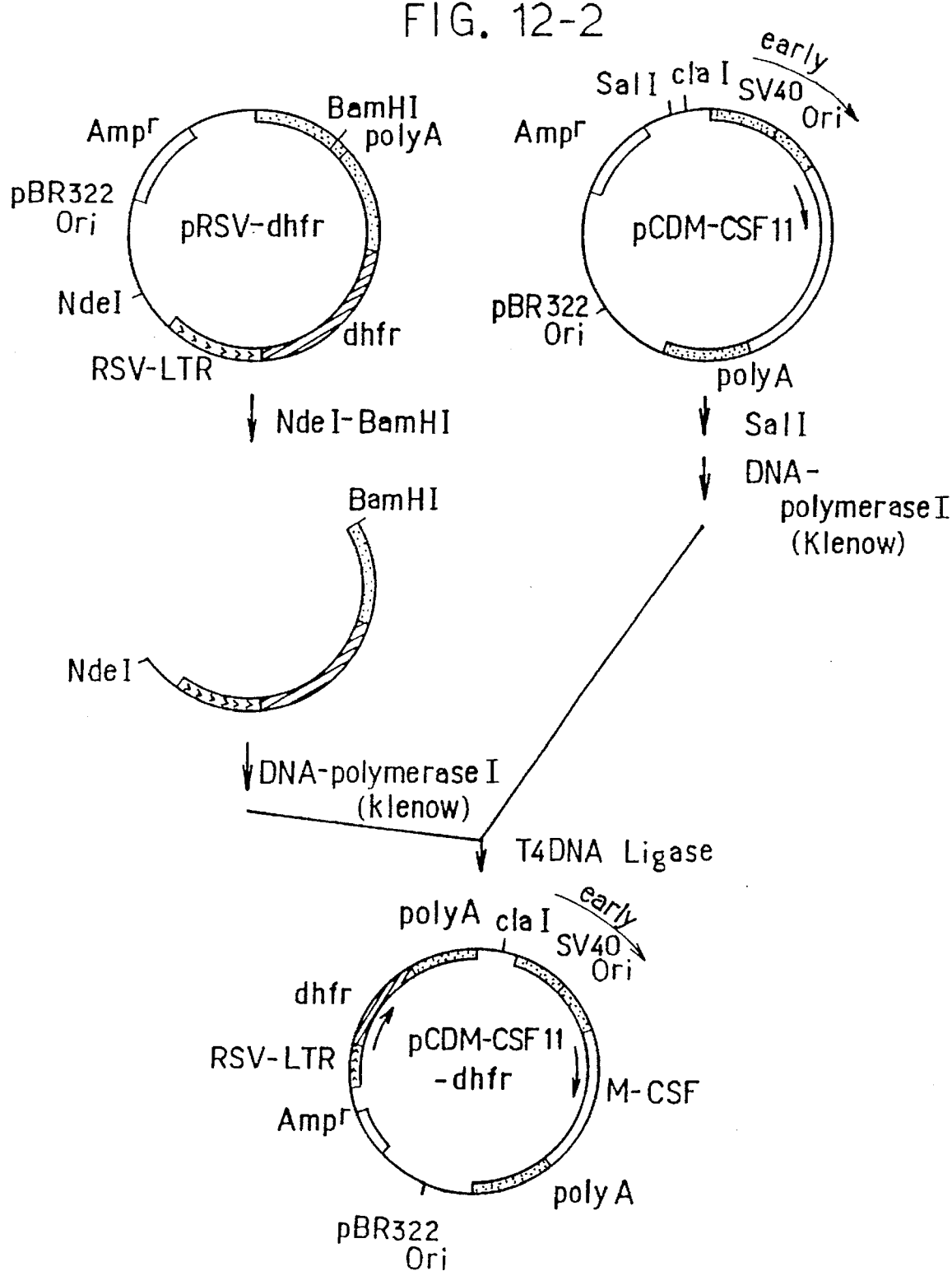

FIGS. 12-1 and 12-2 schematically show the above process.

(16) Preparation of r-MCSF

Using the plasmid pcDM-CSF11-dhfr thus obtained, r-MCSF was produced by the procedure (3). The CSF activity of the culture supernatant obtained was 68 in terms of the number of colonies (average) per plate (0 for plasmid pcDE as a control).

(17) Expression of M-CSF by pcDM.CSF11-dhfr in CHO cells

Dulbecco's modified minimum essential medium (DMEM medium, product of GIBCO Laboratories) was supplemented with 10% FCS, 10 ml of 100 mM sodium pyruvate, 10 ml of nonessential amino acids, 100,000 units of penicillin G, 200 mg of streptomycin, 80 mg of gentamicin and 53 ml of 7% sodium hydrogencarbonate per liter. To the medium was added chinese hamster ovary dhfr-deficient cells (CHO-DuK dhfr⁻ cells; Proc. Natl. Acad. Sci. U.S.A., 77, 4216(1980)) in the ratio of about $2 \times 10^6$ cells per 40 ml of the medium in 75-cm² incubator flask (product of Costar Corp.). The cells were incubated for 6 to 8 days and the supernatant of the culture was collected. CHO-Duk dhfr⁻ cells were also treated with trypsin (product of Flow Lab. Inc.) in the usual manner, suspended in the same DMEM, washed with the same medium and separated from the medium.

The cells were then suspended in a DNA injection solution (0.25M mannitol-0.1 mM $CaCl_2.2H_2O$-0.1 mM $MgSO_4.7H_2O$-0.2 mM Tris-HCl (pH 7.2), Wako Pure Chemical Industries Ltd.).

The M-CSF expression plasmid pcDM.CSF11-dhfr obtained by the procedure (15) was cleaved into linear form with ClaI and thereafter dissolved in the DNA injection solution.

The cell suspension (200 μl, $2 \times 10^6$ cells) and the DNA solution (200 μl, 30 μg of DNA) were mixed together, and the mixture was placed into Fusion Chamber CH-2 (product of Shimadzu Seisakusho Ltd.), which was connected to Electric Fusion Device SSH-1 (product of Shimadzu Seisakusho Ltd.). 4.2 kV/cm² pulse was applied to the mixture twice at an interval of 1 second to electrically transfect the DNA into the cells.

The cells having the DNA transfected therein were suspended in 10% dialyzed FCS-1% nonessential amino acid solution (product of Flow Lab. Inc.)-2% HT solution (product of Flow Lab. Inc.)-DMEM medium and incubated on a 24-well plate (product of Costar Corp.).

After incubation for 48 hours, the medium was replaced by a selective medium (DMEM medium containing 10% dialyzed FCS and 1% nonessential amino acid solution). The medium was thereafter replaced by a fresh one every 3 to 4 days.

From among about 200 clones of transformant cells obtained by incubating for 10 to 14 days, 50 clones were selected, treated with trypsin in the usual manner and transferred to a new 24-well plate.

The amplification of the DHFR gene gives resistance to methotrexate (MTX) of high concentration (J.B.C., 253, 1357(1978)), while the gene cotransfected with a DHFR gene are amplified by MTX (J. Mol. Biol., 159, 601 (1982)).

The 50 clones of transformant cells were further incubated in a selective medium containing 20 nM MTX. The proliferated resistant clones were treated with trypsin, then suspended in a selective medium containing 50 nM MTX and incubated. Similarly, the proliferated resistant clones were further incubated in a selective medium containing 100 nM MTX, eventually affording clones which were resistant to 400 nM MTX.

Table 7 below shows the CSF activity of the supernatants of cultures of these resistant clones.

TABLE 7

| CHO cells | Resistant to: | |
|---|---|---|
| Clone No. | MTX 100 nM | MTX 400 nM |
| 2, 3-8 | 2,940 | 30,240 |
| 2, 3-15 | 2,480 | 13,770 |
| 2, 3-18 | 6,060 | 22,770 |
| 2, 3-20 | 4,380 | 24,030 |
| 2, 3-42 | 3,900 | 19,530 |

The culture supernatant of CHO cells as prepared by the above procedure was directly used as a sample for SDS-PAGE and analyzed for molecular weight in the same manner as in the procedure (14). Consequently, the M-CSF band was detected at a position corresponding to 90,000 under a non-reducing condition and to 44,000 under a reducing condition.

(18) Separation and purification of CHO.M-CSF

Dulbecco's modified minimum essential medium (DMEM medium, product of GIBCO Laboratories) was supplemented with 10% FCS, 10 ml of 100 mM sodium pyruvate, 10 ml of nonessential amino acids, 100,000 units of penicillin G, 200 mg of streptomycin, 80 mg of gentamicin and 53 ml of 7% sodium hydrogen carbonate per liter. To the medium was added CHO cell clone No.2, 3-8 obtained by the procedure (17) in the ratio of about $2 \times 10^6$ cells per 40 ml of the medium. The clone was cultivated for 6 to 8 days.

The desired homogeneous human M-CSF (CHO.M-CSF) was isolated from the supernatant of the culture by the following purification steps.

In the following steps, the desired protein was detected by the Western blotting method.

1) ConA-Sepharose affinity chromatography

To 650 ml of the CHO cell culture supernatant was added 650 ml of 50 mM sodium borate buffer (pH 8.0) containing 1.0M NaCl and the mixture was stirred to prepare a sample solution.

The sample solution was applied to a column, 5×60 cm, packed with ConA-Sepharose gel (350 ml in volume) and equilibrated with 50 mM sodium borate buffer (pH 8.0) containing 0.5M NaCl. After thoroughly washing the column with the same buffer, the solution was eluted with the same buffer containing 0.5M methyl-α-D-mannoside.

CHO.M-CSF was detected only in methyl-α-D-mannoside-eluted fractions.

2) TSKgel DEAE-5PW ion exchange HPLC

The active fraction obtained by step 1) was concentrated by ultrafiltration using YM-10 membrane. The concentrate was dialyzed against 50 mM sodium borate buffer (pH 8.0), followed by anion exchange HPLC under the following conditions four times separately.

Column: TSKgel DEAE-5PW (21.5 mm I.D.×15 cm, product of TOSOH CORPORATION)

Eluent A: 50 mM sodium borate buffer (pH 8.0) containing 5% methanol

Eluent B: 50 mM sodium borate buffer (pH 8.0) containing 1.0M NaCl and 5% methanol Flow rate: 3.0 ml/min Fraction volume: 6 ml/tube/2 min

| Gradient programn: | |
|---|---|
| Time (min) | % B |
| 0 | 0 |
| 10 | 0 |
| 20 | 10 |
| 95 | 29 |
| 100 | 100 |
| 110 | 100 |
| 115 | 0 |
| 130 | 0 |

Consequently, CHO.M-CSF was eluted in fractions No.34 to No.38 (0.23 to 0.25M NaCl). Fraction was commenced immediately after the injection of the sample. These fractions were collected and used for the following steps.

3) Gel filtration HPLC

The CHO.M-CSF fraction obtained by step 2) was concentrated by ultrafiltration using YM-10 membrane and thereafter subjected to gel filtration HPLC under the following conditions six times separately.

Column: TSKgel G3000SW (60 cm×21.5 mm I.D., product of TOSOH CORPORATION)

Eluent: 50 mM sodium phosphate buffer (pH 6.8) containing 0.3M NaCl

Flow rate: 3.0 ml/min

Fraction volume: 6 ml/tube/2 min

Consequently, CHO.M-CSF was eluted in fractions No.23 to No.26.

The molecular weight of CHO.M-CSF was estimated to be 114,000 from the eluted position of a standard protein for gel filtration HPLC (product of Oriental Yeast Co., Ltd.)

4) Reverse phase HPLC (RP-HPLC)

The CHO.M-CSP fraction obtained by step 3) was concentrated by ultrafiltration using YM-10 membrane and then subjected to RP-HPLC under the following conditions.

Column: $C_4$ Hi-pore reverse phase column (Hi-pore RP-304, product of Bio-Rad Laboratories, 4.6 mm I.D.×250 mm)

Eluent A: 0.1% TFA

Eluent B: acetonitrile-1% TFA (9:1)

Flow rate: 1 ml/min

Fraction volume: 2 ml/tube/2 min

| Gradient programm: | |
|---|---|
| Time (min) | % B |
| 0 | 0 |
| 10 | 0 |
| 15 | 40 |
| 85 | 60 |
| 90 | 100 |
| 95 | 100 |
| 100 | 0 |
| 110 | 0 |

The $C_4$ RP-HPLC gave fractions No.31 and No.32 (52 to 53% B) containing CHO.M-CSF. These fractions were combined together, neutralized with 200 mM sodium borate buffer (pH 8.0) and thereafter concentrated in vacuo by a centrifugal concentrator (product of TOMY SEIKO CO., LTD.).

5) TSKgel DEAE-5PW ion exchange HPLC

The CHO.M-CSF fraction obtained by step 4) was subjected to TSKgel DEAE-5PW ion exchange HPLC under the following conditions.
Column: TSKgel DEAE-5PW (7.5 mm I.D.×75 mm, product of TOSOH CORPORATION)
Eluent A: 50 mM sodium borate buffer (pH 8.0) containing 5% methanol
Eluent B: 50 mM sodium borate buffer (pH 8.0) containing 1.0M NaCl and 5% methanol
Flow rate: 1.0 ml/min
Fraction volume: 1 ml/tube/min

| Gradient programm: | |
|---|---|
| Time (min) | % B |
| 0 | 0 |
| 7 | 0 |
| 42 | 30 |
| 47 | 100 |
| 52 | 100 |
| 57 | 0 |
| 62 | 0 |

Figure 13:
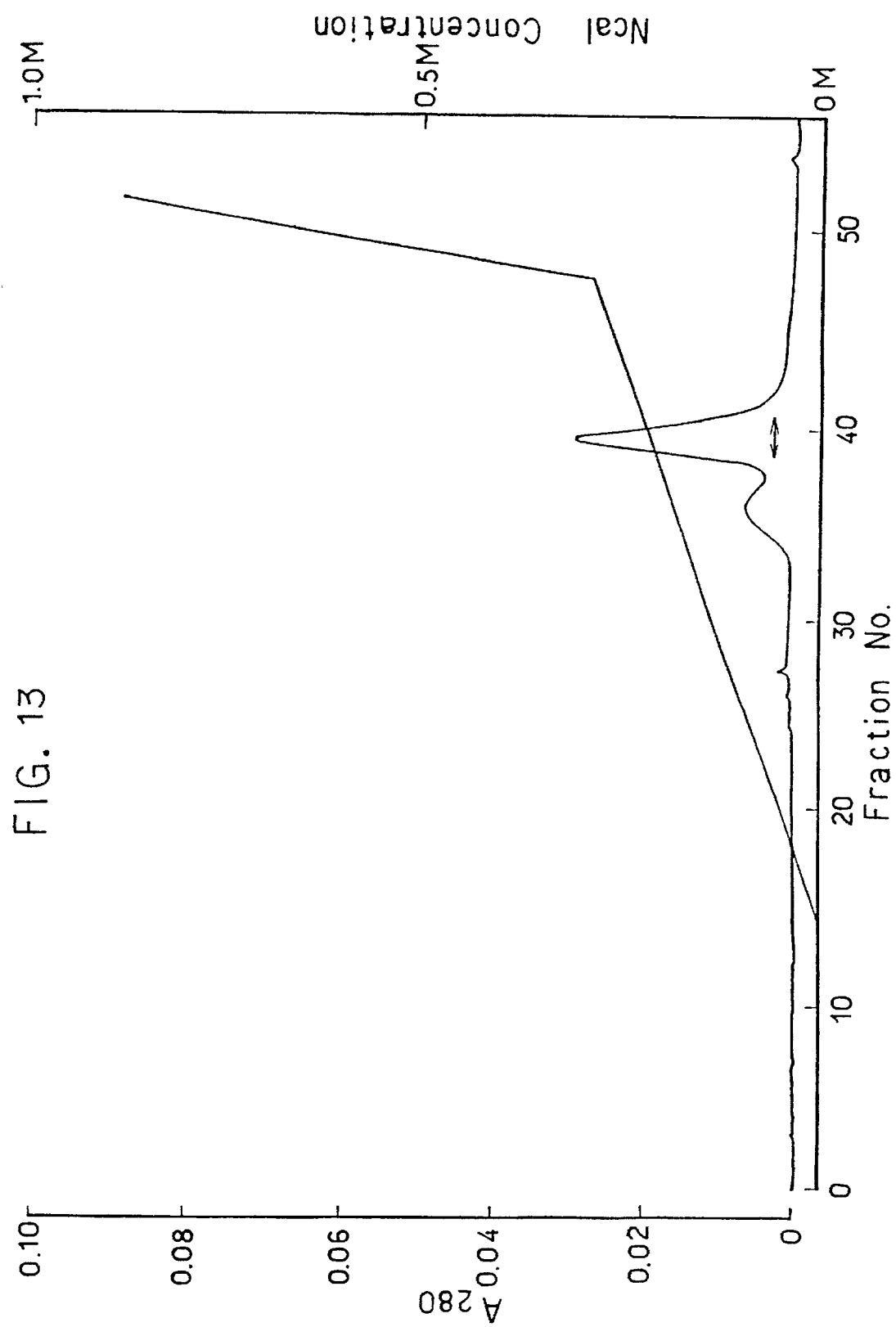
FIG. 13 shows CHO.M-CSF elution profile obtained by DEAE-5PW ion exchange high performance liquid chromatography.

FIG. 13 shows the elution profile.

In the figure, plotted as ordinate are the absorbance of protein at 280 nm ($A_{280}$) and NaCl concentration (M) vs. the fraction No. as abscissa. The double arrow (⇆) shown indicates the eluted position of CHO.M-CSF as detected by Western blotting.

The figure shows that CHO.M-CSF is present and detected in fractions Nos. 39 and 40.

These fractions were collected, concentrated in vacuo by a centrifugal concentrator and subjected to SDS-PAGE, whereby a single protein band was detected. The band was in coincidence with the band position determined by the Western blotting.

6) N-terminal amino acid sequence of CHO.M-CSF

The N-terminal amino acid sequence of the CHO.M-CSF thus obtained by step 5) was determined using a gas phase sequencer (Applied Biosystems).

Consequently, it was found that the CHO.M-CSF had the following sequence of ten N-terminal amino acids.

Glu-Glu-Val-Ser-Glu-Tyr-X'-Ser-His-Met-

It was impossible to identify the amino acid (X') in cycle 7. The cDNA sequence suggests that this amino acid residue is Cys.

7) SDS-PAGE of CHO.M-CSF

According to the method of Laemmli (Laemmli, U.K., Nature, 277, 680 (1970)), the CHO.M-CSF concentrate obtained by step 5) was dissolved in Laemmli's sample buffer with (2-ME$^+$) or without 2-mercaptoethanol (2-ME$^-$). The solutions were heat-treated at 95° C. for 5 minutes and then subjected to SDS-PAGE under the following conditions.
Gel: 12% polyacrylamide gel, 1.5 mm in thickness.
Device: PROTEAN (product of Bio-Rad Laboratories)
Electrophoresis conditions: constant current of 20 mA for stacking gel, and 30 mA for separating gel. Electrophoresed for about 4 hours.
Staining: Silver Stain Kit (product of Wako Pure Chemical Industries, Ltd.)
Molecular weight marker: Prestained Marker (product of Bio-Rad Laboratories)

From the result of SDS-PAGE, the molecular weight of CHO.M-CSF was estimated to be about 76000 under non-reducing condition (2-ME$^-$) and about 38000 under reducing condition (2-ME$^+$). The CSF was electrophoresed as a single band at these positions.

8) Isoelectric point of CHO.M-CSF

Using the partially purified sample obtained by step 2), the isoelectric point of CHO.M-CSF was determined by the following method.

The sample (100 µl) was applied to a gel (LBK Ampholine PAG plate, pE 3.5–9.5) and electrophoresed at 10 W for 2 hours. The gel was thereafter sliced at a spacing of 5 mm, then placed into 1 ml of 50 mM sodium borate (pH 8.0) and tested for activity after elution for 24 hours. The gel was also sliced at a spacing of 1 cm, then allowed to stand in 500 µl of distilled water for 24 hours and then subjected to pH determination.

Figure 14:
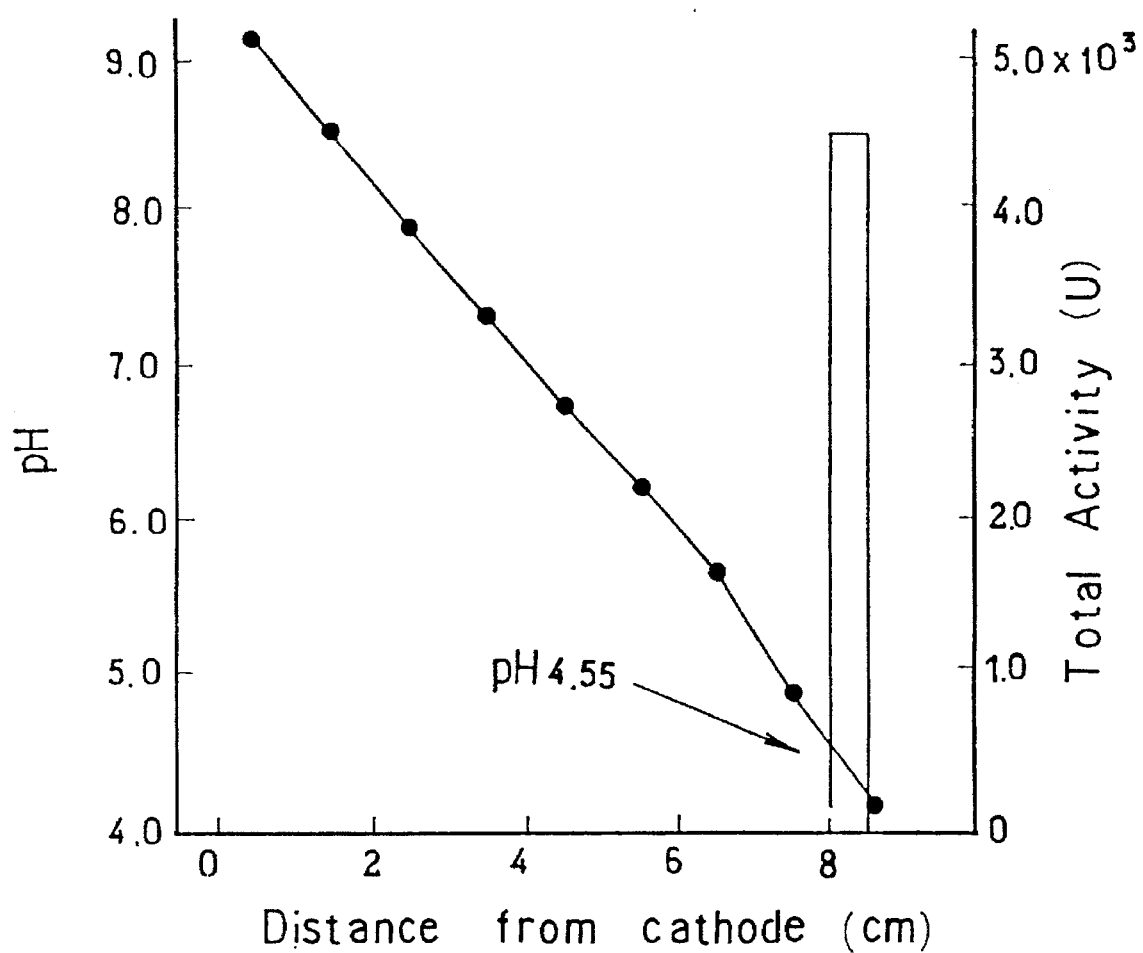
FIG. 14 is a graph showing the result obtained by measuring the isoelectric point of CHO.M-CSF.

The result is shown in FIG. 14, in which the pH and total activity (U) are plotted as ordinate vs. the distance (cm) from the cathode as abscissa.

The results shows that the isoelectric point of CHO.M-CSF is pH 4.55.

(19) Preparation of M-CSF expression plasmid pcDM.CSF11-185-dhfr

The plasmid pcDM.CSF11-dhfr prepared by the procedure (15) was cleaved with restriction enzyme XhoI into two fragments, and the fragment containing DHFR gene was isolated and purified.

On the other hand, the plasmid pcDM.CSF11-185 prepared by the procedure (7) was cleaved with restriction emzyme XhoI into two fragments, and the fragment containing M-CSF11-185cDNA was isolated and purified.

The two kinds of fragments thus obtained were ligated together with T4DNA ligase, and the product was introduced into E. coli HB101 competent cells (Takara Shuzo Co., Ltd.) for transformation. Plasmid DNA was prepared from the resulting colonies which were resistant to ampicillin, a restriction enzyme map was then determined, and the desired plasmid pcDM.CSF11-185-dhfr was obtained.

The plasmid is plasmid pcDM.CSF11-dhfr wherein M-CSF11 DNA is converted to M-CSF11-185 DNA. Except this, the plasmid is identical with pcDM.CSF11-dhfr. The transformant obtained by introducing the plasmid pcDM.CSF11-185-dhfr into E. coli HB101 strain has been deposited under the name of Escherichia coli HB101/ pcDM.CSF11-185-dhfr with deposition number FERM BP-2223 in Fermentation Research Institute Agency of Industrial Science & Technology since Dec. 26, 1988.

(20) Expression in CHO cells

The plasmid pcDM.CSF11-185-dhfr obtained by the procedure (19) was introduced into CHO-Duk dhfr$^-$ cells, which were then incubated in the same manner as in the procedure (17) to eventually obtain 50 clones resistant to 400 nM MTX.

Six clones were selected from among these resistant clones and checked for the CSF activity of culture supernatant. Table 8 shows the result.

TABLE 8

| CHO cells | CSF activity | |
|---|---|---|
| Clone No. | Active Unit (U/ml) | Number of colonies |
| 4-1 | 188,800 | 25,800 |
| 4-7 | 180,500 | 24,600 |
| 4-12 | 338,200 | 46,100 |
| 4-16 | 105,200 | 14,300 |
| 4-20 | 75,700 | 10,300 |
| 4-32 | 296,900 | 40,500 |

The CSF activity (U/ml) was calculated from the following equation;
CSF activity (U/ml)=(Number of colonies)×(Dilution ratio) ÷1.5.

CHO cells (clones No.4 to No.12) were cultivated in the same manner as in the procedure (18) and the desired M-CSF in the supernatant was similarly purified (by ConA-Sepharose chromatography, TSKgel DEAE-5PW ion exchange HPLC, gel filtration HPLC, reverse phase HPLC and TSKgel DEAE-5PW HPLC).

The desired protein, i.e. M-CSF, resulting from the purification steps was detected by the Western blotting method.

In the same manner as in the procedure (14), the M-CSF fraction obtained by the final purification step was subjected to SDS-PAGE and its molecular weight was determined by the Western blotting method.

The fraction was also electrophoresed for the determination of the isoelectric point in the same manner as in the procedure (18), 8). M-CSF was thereafter detected by staining with Coomassie Brilliant Blue R250 and also by Western blotting with use of 10% methanol-containing 1% acetic acid solution as a transfer buffer.

As a results, the M-CSF had a molecular weight of 42,000 and 46,000 under nonreducing condition and contained a minor component with a molecular weight of 39,000. Under reducing condition, the molecular weight of the main component was 22,000 and 27,000. A band was also detected at 16,000 as a minor component.

The isoelectric point (pI) of the M-CSF was 3.5 to 4.6. It was found that the CSF was composed primarily of five kinds of molecules.

(21) Preparation of M-CSF expression plasmid pRSVS-MCSF11-dhfr

Plasmid pRSV-S was prepared from the DHFR expression plasmid pRSV-dhfr obtained by the procedure (15), by cleaving the plasmid with restriction enzymes HindIII and BglII to obtain a fragment, which devoided the DHFR gene portion. Both ends of the fragment were converted to SalI ends with SalI linker (Takara Shuzo Co., Ltd.), and ligated with T4 DNA ligase.

A DNA fragment including RSV-LTR was isolated from the plasmid pRSV-S and purified, by cleaving the plasmid with restriction enzyme BamHI, making the fragment blunt-ended with DNA polymerase and further cleaving the fragment with restriction enzyme NdeI.

On the other hand, plasmid pSV2-dhfr (Mol. Cell. Biol., 1, 854 (1981)) was cleaved with restriction enzyme EcoRI and ClaI cleavage site was added with ClaI linker (Takara Shuzo Co., Ltd.) to prepare plasmid pSV2-dhfr-EC. This plasmid was cleaved with restriction enzymes NdeI and PvuII to isolated and purify a DNA fragment containing DHFR gene.

The two DNA fragments thus purified were ligated together with T4DNA ligase to obtain plasmid pRSVS-dhfr.

The plasmid pcDM.CSF11-dhfr separately prepared by the procedure (15) was cleaved with restriction enzyme EcoRI to obtain M-CSF gene. Both ends of the fragment were converted to SalI ends using SalI linker (Takara Shuzo Co., Ltd.). The fragment was ligated with the above plasmid pRSVS-dhfr at SalI site using T4DNA ligase. The plasmid was then introduced into E. coli EB101 (Takara Shuzo Co., Ltd.).

The resulting M-CSF expression plasmid pRSVS-MCSF11-dhfr was mapped with restriction enzymes to identify the plasmid as the desired plasmid.

Figure 22A:
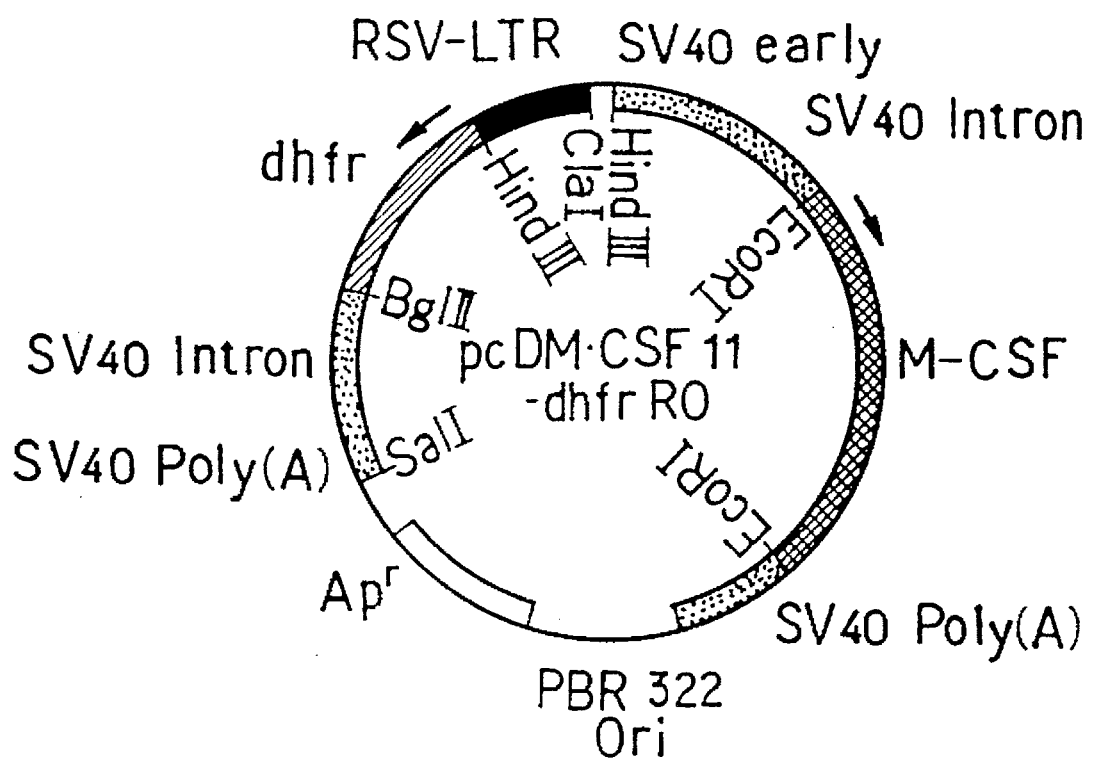
FIGS. 22A–C show the structures of pcDM.CSF11-dhfrRO, pSV2S-MCSF11-dhfr and pRSVS-MCSF11-dhfr which are M-CSF expression plasmids.
Figure 22B:
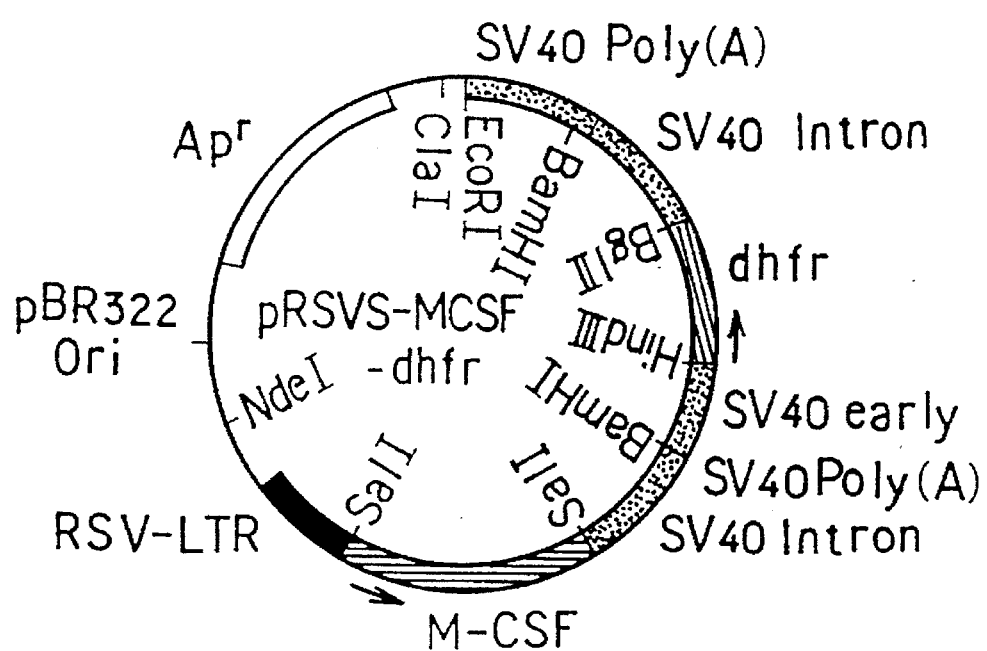

FIG. 22B shows the structure.

As seen in FIG. 22B, the plasmid contains LTR portion of RSV (RSV-LTR) participating in expressing M-CSF, M-CSF gene (M-CSF), SV40-derived intervening sequence (SV40 intron), polyadenylation signal (SV40 polyA), early promoter portion (SV40 early) participating in the expression of DHFR, DHFR gene (dhfr), SV40-derived intervening sequence (SV40 intron) and polyadenylation signal (SV40 polyA). The plasmid further contains replication origin (pBR322 ori) and ampicillin-resistant gene (Ap$^r$) derived from E. coli plasmid pBR322.

(22) Preparation of M-CSF expression plasmid pSV2S-MCSF11-dhfr

Plasmid pSV2-S was obtained from the DHFR expression vector pSV2-dhfr-EC prepared by the procedure (21), by cleaving the vector with restriction enzymes HindIII and BglII to remove DHFR gene, converting both ends of the fragment to SalI ends with SalI linker and ligating the ends with T4DNA ligase.

On the other hand, a DNA fragment containing DHFR gene was isolated from plasmid pRSV-dhfr and purified, by cleaving the plasmid with restriction enzyme NdeI, converting both ends of the fragment to BamHI ends with BamHI linker (Takara Shuzo Co., Ltd.) and further cleaving the fragment with restriction enzyme BamHI.

The DNA fragment obtained was ligated at BamHI site of the plasmid pSV2-S with T4DNA ligase to prepare plasmid pSV2S-dhfr.

M-CSF expression plasmid pcDM.CSF11-dhfr was cleaved with restriction enzyme EcoRI, M-CSF gene was separated, both ends of the fragment were converted to SalI ends with SalI linker, the fragment was ligated at SalI site of the plasmid pSV2S-dhfr with T4DNA ligase, and the plasmid was introduced into E. coli HB101.

The plasmid thus obtained was found to the desired plasmid pSV2S-MCSF11-dhfr by restriction enzyme mapping.

Figure 22C:
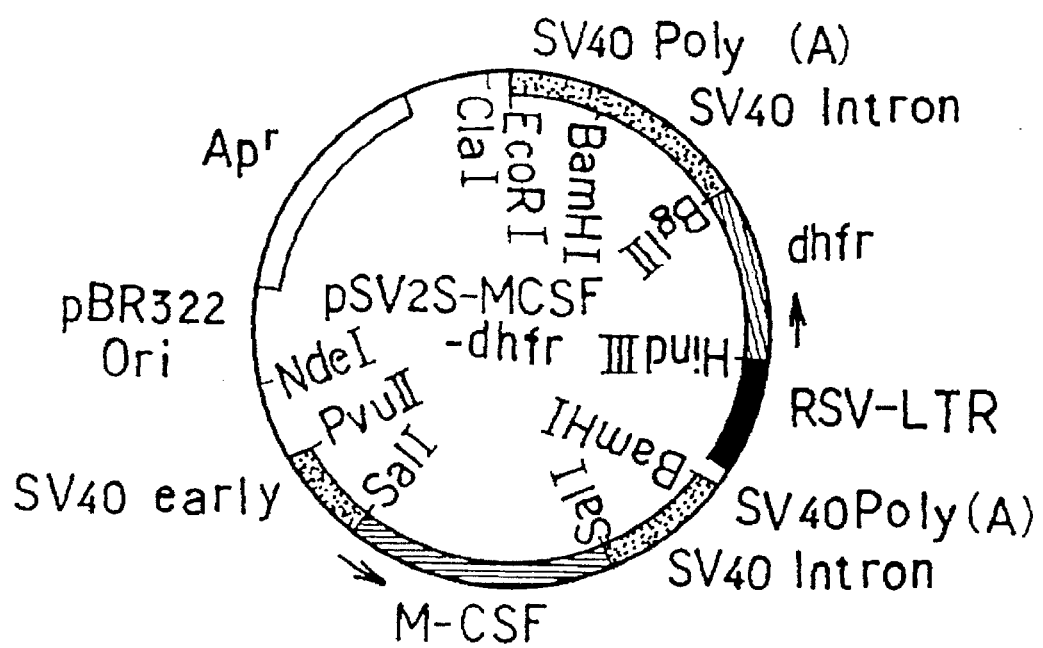

FIG. 22C shows the structure of the plasmid. With reference to FIG. 22C, the plasmid contains an early promoter portion (SV40 early) derived from SV40, M-CSF gene (M-CSF), intervening sequence (SV40 intron) derived from SV40, polyadenylation signal (SV40 polyA), LTR portion derived from RSV (RSV-LTR), DHFR gene (dhfr), intervening sequence (SV40 intron) derived from SV40, and polyadenylation signal (SV40 polyA). The plasmid further contains a replication origin (pBV322 ori) and ampicillin-resistant gene (Ap$^r$) derived from E. coli plasmid pBR322.

(23) Preparation of M-CSF expression plasmid pcDM.CSF11-dhfrRO

DHFR expression vector pRSV-dhfr was cleaved with restriction enzyme BamHI, the cleavage site was made to have SalI end with SalI linker, the fragment was further cleaved with restriction enzyme NdeI, and ClaI end was formed at the cleave site with ClaI linker to obtain plasmid pRSV-dhfr-CS.

This plasmid was cleaved with restriction enzymes ClaI and SalI to isolate and purify a DNA fragment containing DHFR gene.

On the other hand, M-CSF expression plasmid pcD-M.CSF11 was cleaved with restriction enzymes ClaI and SalI to isolate and purify a DNA fragment containing M-CSF gene, which was then ligated with the above DNA fragment containing DHFR gene with T4DNA ligase. The resulting fragment was transformed into E. coli HB101. Restriction enzyme mapping of the plasmid consequently obtained indicated that M-CSF gene and DHFR gene therein were opposite in the direction of transcription, revealing that the plasmid was the desired plasmid pcDM.CSF11-dhfrRO.

FIG. 22A shows the structure of the plasmid. With reference to this diagram, the plasmid contains an early promoter portion (SV40 early) derived from SV40, intervening sequence (SV intron), M-CSF gene (M-CSF) and polyadenylation signal (SV40 polyA). The plasmid further contains, as arranged in opposite relation to these in transcription direction, LTR portion of RSV (RSV-LTR), DHFR gene (dhfr), intervening sequence derived from SV40 (SV40 intron) and polyadenylation signal (SV40 polyA). The plasmid further contains a replication origin (pBR322 ori) and ampicillin-resistant gene (Ap$^r$) derived from E. coli plasmid pBR322.

(24) Introduction of M-CSF expression plasmid into CHO cells and expression of M-CSF The M-CSF expression plasmids prepared by procedures (15), (19), (22) and (23) were introduced into CHO cells for expressing M-CSF.

The host CHO cells were CHO-dhfr-DG44 cells (Somatic Cell and Molecular Genetics, 12(6), 555 (1986)).

The methods included in procedure (17) were used for the introduction of plasmids, incubation of CHO cells and gene amplification with MTX.

The cells having each plasmid introduced therein were incubated in a selective medium containing 400 nM MTX to obtain resistant clones, which were further incubated in the same medium containing 1 µM MTX. The clone which was grown in the medium was further incubated in the same medium containing 3 µM MTX to obtain resistant clones.

The resulting clones resistant to 3 µM MTX were incubated on a 24-well plate (product of Costar). When cells grown confluently, the cells were collected. A one-fifth volume of the resulting cell suspension was freshly inoculated into 1 ml of MTX-free D-MEM medium containing 10% FCS on a 24-well plate, followed by culturing for 6 days and collection of the culture supernatants.

Each supernatant was checked for the production of M-CSF by determining the molecular weight of M-CSF by Western blotting. The clones with high yields of M-CSF where checked for M-CSF activity.

Table 9 shows the results.

TABLE 9

| Plasmid | Clone | CSF activity Active Unit (u/ml) | Number of colonies |
|---|---|---|---|
| pcDM.CSF11-dhfr | 5-8 | $2.55 \times 10^5$ | $3.48 \times 10^4$ |
|  | 5-9 | $1.83 \times 10^5$ | $2.50 \times 10^4$ |
|  | 5-10 | $2.27 \times 10^5$ | $3.10 \times 10^4$ |
|  | 5-14 | $1.05 \times 10^5$ | $1.43 \times 10^4$ |
|  | 5-15 | $1.38 \times 10^5$ | $1.88 \times 10^4$ |
|  | 5-17 | $1.11 \times 10^5$ | $1.51 \times 10^4$ |
|  | 5-22 | $1.54 \times 10^5$ | $2.10 \times 10^4$ |
|  | 5-24 | $1.81 \times 10^5$ | $2.47 \times 10^4$ |
| pcDM.CSF11-dhfrRO | 6-2 | $2.35 \times 10^5$ | $3.21 \times 10^4$ |
|  | 6-8 | $1.15 \times 10^5$ | $1.57 \times 10^4$ |
|  | 6-14 | $3.53 \times 10^5$ | $4.81 \times 10^4$ |
|  | 6-17 | $2.35 \times 10^5$ | $3.21 \times 10^4$ |
|  | 6-19 | $2.59 \times 10^5$ | $3.53 \times 10^4$ |
|  | 6-20 | $1.65 \times 10^5$ | $2.25 \times 10^4$ |
|  | 6-22 | $1.61 \times 10^5$ | $2.20 \times 10^4$ |
|  | 6-24 | $2.98 \times 10^5$ | $4.06 \times 10^4$ |
| pSV2S-MCSF11-dhfr | 7-1 | $0.18 \times 10^5$ | $0.24 \times 10^4$ |
|  | 7-2 | $1.53 \times 10^5$ | $2.09 \times 10^4$ |
|  | 7-4 | $4.03 \times 10^5$ | $5.50 \times 10^4$ |
|  | 7-10 | $2.35 \times 10^5$ | $3.21 \times 10^4$ |
|  | 7-16 | $1.49 \times 10^5$ | $2.03 \times 10^4$ |
|  | 7-17 | $1.15 \times 10^5$ | $1.57 \times 10^4$ |
|  | 7-20 | $0.08 \times 10^5$ | $0.11 \times 10^4$ |
|  | 7-21 | $2.96 \times 10^5$ | $4.04 \times 10^4$ |
|  | 7-23 | $1.10 \times 10^5$ | $1.50 \times 10^4$ |
| pRSVS-MCSF11-dhfr | 8-11 | $2.18 \times 10^5$ | $2.97 \times 10^4$ |
|  | 8-21 | $4.27 \times 10^5$ | $5.82 \times 10^4$ |
|  | 8-22 | $1.12 \times 10^5$ | $1.53 \times 10^4$ |
| pcDM.CSF11-185-dhfr | 9-2 | $7.88 \times 10^5$ | $10.75 \times 10^4$ |
|  | 9-7 | $2.82 \times 10^5$ | $3.85 \times 10^4$ |
|  | 9-8 | $9.02 \times 10^5$ | $12.30 \times 10^4$ |
|  | 9-11 | $5.62 \times 10^5$ | $7.67 \times 10^4$ |

All M-CSF expression plasmids used expressed M-CSF in the CHO cells.

The M-CSF of all samples checked by Western blotting was equivalent in molecular weight to the M-CSF (CHO.M-CSF) obtained from host CHO-Dukdhfr$^-$ cells in procedure (17).

EXAMPLES 3

Preparation of recombinant M-CSF (r-MCSF) by two-cistron systems (1) Preparation of M-CSF expression plasmid ptrpIL-2X.M.CSF101

The plasmid pcDM.CSF11-185 obtained in Example 2, procedure (7) was digested with restriction enzymes ScaI and BamHI, and ScaI-BamHI DNA fragment (about 450 bp) was isolated and purified by agarose gel electrophoresis.

The synthetic linker (I) given below was ligated with the cleaved ScaI end of the DNA fragment using T4DNA ligase to obtain XbaI-BamHI DNA fragment (about 480 bp) having XbaI cleavage site toward the ScaI end.

Synthetic linker (I):

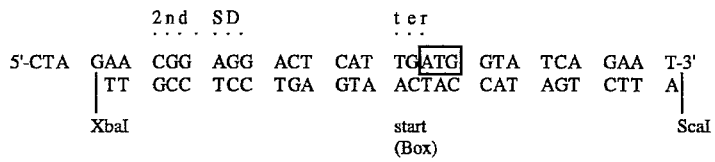

The DNA fragment obtained was inserted into XbaI-BamHI cleavage site of human IL-2 expression plasmid ptrpIL-2D8Δ (see Unexamined Japanese Patent Publication SHO 63-12958), giving the desired plasmid ptrpIL-2X.M.CSF101. The transformant obtained by introducing the plasmid into *E. coli* HB101 strain has been deposited under the name of *Escherichia coli* HB101/ptrpIL-2X-M-CSF101 with deposition number FERM BP-2226 in Fermentation Research Institute Agency of Industrial Science & Technology since Dec. 26, 1988.

This plasmid has two polypeptides coded for within a transcription unit governed by *E. coli* tryptophan promoter: one polypeptide having 65 amino acids including translation starting methionine, N-terminal 60 amino acids of human IL-2 and 4 amino acids coded for by an intercistronic sequence, and the other having 152 amino acids including translation starting methionine and human M-CSF with 151 amino acids from 35th amino acid (Val) to 185th amino acid (Thr) shown in FIG. 5.

In this two-cistron expression system, translation of the second cistron is initiated by the attachment of ribosome to the second SD sequence positioned in the intercistronic sequence.

FIG. 15 schematically shows the structure of the above two-cistron expression system.

(2) Preparation of M-CSF expression plasmid ptrpIL-2X.M.CSF102

The desired plasmid ptrpIL-2X.M.CSF102 different from the above plasmid only in intercistronic sequence was prepared in the same manner as in procedure (1) except that the linker (II) given below was used.

FIG. 16 shows the structure of the plasmid.

Synthetic linker (II):

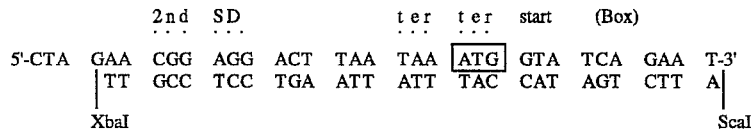

(3) Preparation of M-CSF expression plasmid ptrpIL-2X.M.CSF103

The desired plasmid ptrpIL-2X.M.CSF103 was prepared in the same manner as in procedure (1) except that the synthetic linker (III) given below was used.

Synthetic linker (III):

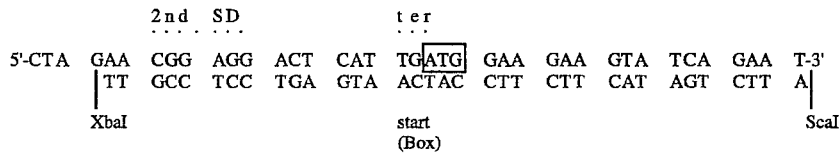

The plasmid is characterized in that the second cistron thereof codes for a polypeptides comprising 154 amino acids, i.e. translation starting methionine and human M-CSF with 153 amino acids from the 33rd amino acid (Glu) to the 185th amino acid (Thr) shown in FIG. 5.

FIG. 17 shows the above structure.

(4) Preparation of M-CSF expression plasmids ptrpIL-2X.M.CSF104, ptrpIL-2X.M.CSF105 and ptrpIL-2X.M.CSF106

Using the plasmid pcDM.CSF-185 obtained in Example 2, procedure (4) in place of plasmid pcDM.CSF11-185, the foregoing procedures (1) to (3) were repeated to respectively give the desired plasmids ptrpIL-2X.M.CSF104 (prepared with use of the synthetic linker (I) and having the structure shown in FIG. 18), ptrpIL-2X.M.CSF105 (prepared with use of the synthetic linker (II) and having the structure of FIG. 19), and ptrpIL-2X.M.CSF106 (prepared with use of the synthetic linker (III) and having the structure of FIG. 20). The transformant obtained by introducing the plasmid ptrpIL-2X.M.CSF104 into *E. coli* HB101 strain has been deposited under the name of *Escherichia coli* HB101/ptrpIL-2X-M-CSF104 with deposition number FERM BP-2225 in Fermentation Research Institute Agency of Industrial Science & Technology since Dec. 26, 1988.

(5) Introduction of M-CSF expression plasmids into *E. coli* and incubation of transformants Each of the plasmids obtained by procedures (1) to (4) was introduced into *E. coli* strain SG21058 (J. Bacteriol., 164, 1124–1135 (1985)), each of the transformants obtained was incubated and each of the protein obtained was analysed by SDS-PAGE and Western blotting by the following method.

The *E. coli* SG21058 harboring the plasmid was incubated with shaking at 37° C. for 8 hours in a 300-ml flask containing 50 ml M9 medium and supplemented with 1% Casamino acid, 0.4% glucose, 5 µg/ml of thiamine hydrochloride, 20 µg/ml of L-cysteine and 50 µg/ml of ampicillin, the culture broth was centrifuged (5,000 r.p.m. for 5 minutes at room temperature) to collect the cell pellets, and the protein produced was analyzed. SDS-PAGE and Western blotting were conducted for detecting M-CSF in the same manner as in Example 2, procedure (14).

The culture of *E. coli* transformed with the plasmid of procedure (1) yielded a large quantity of polypeptides, about 8 kd and about 17 kd in molecular weight as determined from CBB-stained images by SDS-PAGE under reducing condition. The former molecular weight was in match with the expected molecular weight of the polypeptide coded for by the first cistron, and the latter with that of the polypeptide coded for by the second cistron.

Analysis conducted by Western blotting using anti-human IL-2 antibody and anti-human M-CSF antibody revealed that the polypeptide with 8 kd was a first cistron translation product containing N-terminal 60 amino acids of IL-2, and that the polypeptide with 17 kd was a second cistron translation product containing M-CSF.

The cultures of *E. coli* transformed with the other plasmids of procedures (2) to (4) were similarly analyzed in the same manner as above to confirm that they produced the translation product (M-CSF) of the second cistron.

(6) Separation and purification of M-CSF

1) Preparation of M-CSF fraction from *E. coli*

To 1.5 g (wet weight) of *E. coli* harboring the plasmid ptrpIL-2X.M.CSF101 obtained by procedure (1) was added 50 ml of 50 mM Tris HCl buffer (pH 7.0) containing 0.5M sucrose, and the mixture was thoroughly stirred. Next, 6 ml of lysozyme (2 mg/ml) and then 4 ml of 0.14M EDTA were added to the mixture, followed by stirring at 4° C. for 15 minutes. The mixture was thereafter centrifuged at 10,000 r.p.m. for 20 minutes.

The supernatant was discarded, and the precipitate was washed with the same buffer as above (50 mM Tris HCl containing 0.5M sucrose, pH 7.0) and similarly centrifuged at 10,000 r.p.m. for 20 minutes to obtain spheroplasts as a precipitate.

Subsequently, 50 ml of 50 mM Tris HCl (pH 7.0) was added to the precipitate to obtain a suspension, which was sonicated at 20 kHz for 10 minutes, followed by centrifugation at 10,000 r.p.m. for 20. minutes, then by washing with the same buffer (50 mM Tris HCl, pH 7.0) and thereafter by centrifugation again under the same condition as above, whereby an M-CSF fraction was obtained as precipitate.

2) Refolding of M-CSF from M-CSF fraction

To the M-CSF fraction obtained by the above step 1) was added 100 ml of 50 mM Tris HCl (pH 7.0) containing 7.0M guanidine hydrochloride, and the mixture was stirred at 4° C. for 1 hour to obtain a solution. The solution was slowly added dropwise into a beaker containing 300 ml of 10 mM Tris HCl (pH 8.5) with stirring. The mixture was thereafter thoroughly dialized against 10 mM Tris HCl (pH 8.5) at 4° C. The dialyzate was centrifuged at 10,000 r.p.m. for 20 minutes to remove the precipitate and obtain a supernatant.

Refolded M-CSF was present in the supernatant.

3) Purification of M-CSF

The M-CSF obtained by the step 2) was purified in the same manner as in Example 2, procedure (18) as will be described below.

3-1) Gel filtration HPLC

The supernatant obtained by the step 2) above was concentrated by a ultrafiltration device (product of Amicon, membrane: YM-10, product of Amicon), the concentrate was passed through 0.45-µm Millipore Filter and subjected to gel filtration HPLC under the following conditions.

Column: TSKgel G3000SW (60 cm×21.5 mm I.D., product of TOSOH CORPORATION)

Eluent: 50 mM sodium phosphate buffer (pH 6.8) containing 0.3M NaCl

Flow rate: 3.0 ml/min

Fraction volume: 6 ml/tube/2 min

From the above procedure, the molecular weight of M-CSF was estimated to be 32,000 in view of the eluted positions of gel filtration HPLC standard proteins (products of ORIENTAL YEAST CO., LTD.), i.e., glutamate dehydrogenase (290,000 in molecular weight), lactate dehydrogenase (142,000 in molecular weight), enolase (67,000 in molecular weight) and adenytate kinase (32,000 in molecular weight).

The active fraction was collected and buffer-exchanged to 40 mM sodium borate (pH 8.0) by ultra-filtration.

3-2) TSKgel DEAE-5PW ion exchange HPLC

The active fraction obtained by the step 3-1) was subjected to TSKgel DEAE-5PW ion exchange HPLC under the following conditions.

Column: TSKgel DEAE-5PW (7.5 mm I.D.×75 mm, product of TOSOH CORPORATION)

Eluent A: 40 mM sodium borate buffer (pH 8.0) containing 5% methanol

Eluent B: 40 mM sodium borate buffer (pH 8.0) containing 1.0M NaCl and 5% methanol Flow rate: 1.0 ml/min Fraction volume: 1.0 ml/tube/min

| Gradient programm: | |
| --- | --- |
| Time (min) | % B |
| 0 | 0 |
| 7 | 0 |
| 42 | 30 |
| 47 | 100 |
| 52 | 100 |
| 57 | 0 |
| 62 | 0 |

Figure 21:
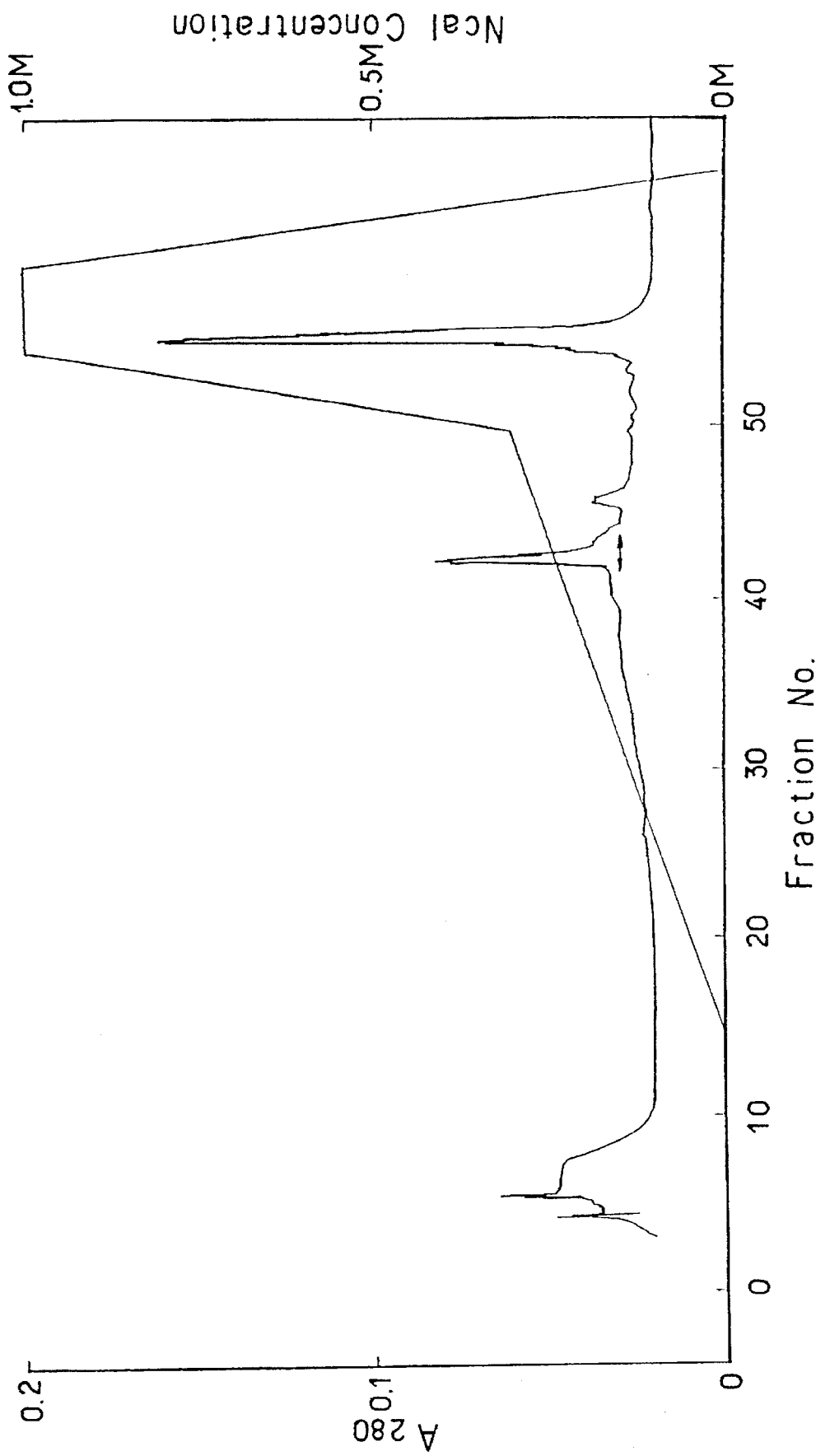
FIG. 21 shows M-CSF elution profile obtained by DEAE-5PW ion exchange high performance liquid chromatography.

FIG. 21 shows the result of the chromatography (elution profile). In the figure, plotted as ordinate are the absorbance ($A_{280}$) of protein at 280 nm and the NaCl concentration (M) vs. the fraction No. as abscissa. The double arrow (⇔) shown indicates M-CSF activity.

The peak for fractions No.42 and No.43 (NaCl concentration 0.23 to 0.25M) corresponds to M-CSF activity.

These fractions were collected to obtain M-CSF from *E. coli*.

3-3) N-terminal amino acid sequence of M-CSF

In the same manner as in Example 2, procedure (18), 6), the N-terminal amino acid sequence of the M-CSF obtained above was determined.

Consequently, the following sequence was determined.

Met-Val-Ser-Glu-Tyr-

4) SDS-PAGE of M-CSF

In the same manner as in Example 2, procedure (18), 7) except for using molecular weight marker from Pharmacia Fine Chemicals (electrophoresis calibration kit), the molecular weight of M-CSF prepared by step 3-2) was determined by SDS-PAGE.

From the result of SDS-PAGE, the molecular weight of M-CSF was estimated to be about 29,500 under nonreducing condition (2-ME⁻) and about 17,400 under reducing condition (2-ME⁺). The CSF was electrophoresed as a single band at these positions.

5) Refolding of M-CSF

To 7.5 g (wet weight) of *E. coli* harboring the plasmid ptrpIL-2X.M.CSF101 obtained by the procedure (1) was added 50 mM Tris HCl buffer (pH 7.0) containing 0.5M sucrose to obtain 100 ml of suspension, which was then thoroughly stirred. Next, 6 ml of lysozyme (24 mg/ml) and then 4 ml of 0.14M EDTA were added to the suspension, followed by stirring at 4° C. for 15 minutes and then by centrifugation at 10,000 r.p.m. for 20 minutes.

The supernatant was discarded, and the precipitate was washed with the same buffer as above (50 mM Tris HCl containing 0.5M sucrose, pH 7.0) and similarly centrifuged at 10,000 r.p.m. for 20 minutes to obtain spheroplasts as a precipitate.

Subsequently, 100 ml of 50 mM Tris HCl (pH 7.0) was added to the precipitate to obtain a suspension, which was sonicated (200 kHz, 2 minutes, 200 W) and then centrifuged at 10,000 r.p.m. for 20 minutes. The resulting precipitate was thoroughly washed with 50 mM Tris HCl (pH 7.5) containing 2% Triton X-100 and then centrifuged again under the same condition to obtain an M-CSF fraction as precipitate.

To the M-CSF fraction obtained was added 20 ml of 50 mM Tris HCl (pH 7.5) containing 7.0M guanidine hydrochloride and 25 mM 2-mercaptoethanol, and the mixture was stirred at room temperature for 4 hours to reduce, denature and solubilize the protein. The solution was slowly placed dropwise into a beaker containing 2,000 ml of 40 mM Tris HCl (pH 8.5), with 0.5 mM reduced glutathione, 0.1 mM oxidized glutathione and 2 mM urea contained therein, while stirring the solution to obtain a 100-fold diluted solution. The solution was thereafter allowed to stand at 4° C. for 1 to 2 days to obtain refolded M-CSF.

6) Isoelectric point of M-CSF

The isoelectric point of the M-CSF prepared by step 5) was determined by the following method.

A 100 μl quantity of M-CSF was applied to a gel (Ampholine PAG plate, pH 3.5–9.5, product of LKB) and electrophoresed at 1W per centimeter (width) of gel. After the current value became constant, the electrophoresis was further continued for 30 minutes. During electrophoresis, the gel was maintained at 10° C. using a cooler (COOLFLOW CFT-25, product of NESLAB Instruments Inc.).

Gel was thereafter sliced at a spacing of 5 mm, then placed into 1 ml of 50 mM sodium borate (pH 8.0) and eluted for 24 hours. The CSF activity of the eluate was determined.

The gel was also sliced at a spacing of 1 cm, and then stood in 1 ml of distilled water for 24 hours. The pH of the water was then measured by a pH meter.

Consequently, the isoelectric point of M-CSF was found to be pH 4.8.

We claim:

1. A process for preparing a biologically active truncated human macrophage colony stimulating factor (M-CSF) polypeptide comprising:

(a) culturing an *Escherichia coli* host cell transformed with an expression plasmid comprising a DNA encoding a biologically active truncated human M-CSF polypeptide under conditions that allow expression of the encoded polypeptides, wherein said truncated M-CSF polypeptide has a sequence beginning at an amino acid selected from the group consisting of 35 (Val), 36 (Ser) and 37 (Glu) of Formula (I) and ending at amino acid 185 (Thr), inclusive, of Formula (I); and (b) purifying the human M-CSF polypeptide expressed therefrom;

Formula (I):

1        10
Met—Thr—Ala—Pro—Gly—Ala—Ala—Gly—Arg—Cys—

20
Pro—Pro—Thr—Thr—Trp—Leu—Gly—Ser—Leu—Leu—

30
Leu—Leu—Val—Cys—Leu—Leu—Ala—Ser—Arg—Ser—

40
Ile—Thr—Glu—Glu—Val—Ser—Glu—Tyr—Cys—Ser—

50
His—Met—Ile—Gly—Ser—Gly—His—Leu—Gln—Ser—

60
Leu—Gln—Arg—Leu—Ile—Asp—Ser—Gln—Met—Glu—

70
Thr—Ser—Cys—Gln—Ile—Thr—Phe—Glu—Phe—Val—

80
Asp—Gln—Glu—Gln—Leu—Lys—Asp—Pro—Val—Cys—

90
Tyr—Leu—Lys—Lys—Ala—Phe—Leu—Leu—Val—Gln—

100
X—Ile—Met—Glu—Asp—Thr—Met—Arg—Phe—Arg—

110
Asp—Asn—Thr—Pro—Asn—Ala—Ile—Ala—Ile—Val—

120
Gln—Leu—Gln—Glu—Leu—Ser—Leu—Arg—Leu—Lys—

130
Ser—Cys—Phe—Thr—Lys—Asp—Tyr—Glu—Glu—His—

140
Asp—Lys—Ala—Cys—Val—Arg—Thr—Phe—Tyr—Glu—

150
Thr—Pro—Leu—Gln—Leu—Leu—Glu—Lys—Val—Lys—

160
Asn—Val—Phe—Asn—Glu—Thr—Lys—Asn—Leu—Leu—

170
Asp—Lys—Asp—Trp—Asn—Ile—Phe—Ser—Lys—Asn—

180
Cys—Asn—Asn—Ser—Phe—Ala—Glu—Cys—Ser—Ser—

190
Gln—Asp—Val—Val—Thr—Lys—Pro—Asp—Cys—Asn—

200
Cys—Leu—Tyr—Pro—Lys—Ala—Ile—Pro—Ser—Ser—

210
Asp—Pro—Ala—Ser—Val—Ser—Pro—His—Gln—Pro—

220
Leu—Ala—Pro—Ser—Met—Ala—Pro—Val—Ala—Gly—

230
Leu—Thr—Trp—Glu—Asp—Ser—Glu—Gly—Thr—Glu—

240
Gly—Ser—Ser—Leu—Leu—Pro—Gly—Glu—Gln—Pro—

250
Leu—His—Thr—Val—Asp—Pro—Gly—Ser—Ala—Lys—

260
Gln—Arg—Pro—Pro—Arg—Ser—Thr—Cys—Gln—Ser—

-continued

```
                                         270
Phe—Glu—Pro—Pro—Glu—Thr—Pro—Val—Val—Lys—
                                         280
Asp—Ser—Thr—Ile—Gly—Gly—Ser—Pro—Gln—Pro—
                                         290
Arg—Pro—Ser—Val—Gly—Ala—Phe—Asn—Pro—Gly—
                                         300
Met—Glu—Asp—Ile—Leu—Asp—Ser—Ala—Met—Gly—
                                         310
Thr—Asn—Trp—Val—Pro—Glu—Glu—Ala—Ser—Gly—
                                         320
Glu—Ala—Ser—Glu—Ile—Pro—Val—Pro—Gln—Gly—
                                         330
Thr—Glu—Leu—Ser—Pro—Ser—Arg—Pro—Gly—Gly—
                                         340
Gly—Ser—Met—Gln—Thr—Glu—Pro—Ala—Arg—Pro—
                                         350
Ser—Asn—Phe—Leu—Ser—Ala—Ser—Ser—Pro—Leu—
                                         360
Pro—Ala—Ser—Ala—Lys—Gly—Gln—Gln—Pro—Ala—
                                         370
Asp—Val—Thr—Gly—Thr—Ala—Leu—Pro—Arg—Val—
                                         380
Gly—Pro—Val—Arg—Pro—Thr—Gly—Gln—Asp—Trp—
                                         390
Asn—His—Thr—Pro—Gln—Lys—Thr—Asp—His—Pro—
                                         400
Ser—Ala—Leu—Leu—Arg—Asp—Pro—Pro—Glu—Pro—
                                         410
Gly—Ser—Pro—Arg—Ile—Ser—Ser—Pro—Arg—Pro—
                                         420
Gln—Gly—Leu—Ser—Asn—Pro—Ser—Thr—Leu—Ser—
                                         430
Ala—Gln—Pro—Gln—Leu—Ser—Arg—Ser—His—Ser—
                                         440
Ser—Gly—Ser—Val—Leu—Pro—Leu—Gly—Glu—Leu—
                                         450
Glu—Gly—Arg—Arg—Ser—Thr—Arg—Asp—Arg—Arg—
                                         460
Ser—Pro—Ala—Glu—Pro—Glu—Gly—Gly—Pro—Ala—
                                         470
Ser—Glu—Gly—Ala—Ala—Arg—Pro—Leu—Pro—Arg—
                                         480
Phe—Asn—Ser—Val—Pro—Leu—Thr—Asp—Thr—Gly—
                                         490
His—Glu—Arg—Gln—Ser—Glu—Gly—Ser—Ser—Ser—
                                         500
Pro—Gln—Leu—Gln—Glu—Ser—Val—Phe—His—Leu—
                                         510
Leu—Val—Pro—Ser—Val—Ile—Leu—Val—Leu—Leu—
                                         520
Ala—Val—Gly—Gly—Leu—Leu—Phe—Tyr—Arg—Trp—
                                         530
Arg—Arg—Arg—Ser—His—Gln—Glu—Pro—Gln—Arg—
                                         540
Ala—Asp—Ser—Pro—Leu—Glu—Gln—Pro—Glu—Gly—
                                         550
Ser—Pro—Leu—Thr—Gln—Asp—Asp—Arg—Gln—Val—
                                         554
Glu—Leu—Pro—Val
``` wherein X is Tyr or Asp.

2. The process of claim 1 wherein the expression plasmid is selected from the group consisting of pIN-III(lpp$^P$-5)-OmpA-MCSF11-NV151 and pIN-III(lpp$^P$-5)-OmpA-MCSF11-NV143.

3. An *Escherichia coli* host cell transformed with an expression plasmid comprising a gene encoding a biologically active truncated human macrophage colony stimulating factor (M-CSF) polypeptide, wherein said truncated human M-CSF polypeptide has a sequence beginning at an amino acid selected from the group consisting of 35 (Val), 36 (Ser) and 37 (Glu) of Formula (I) and ending at amino acid 185 (Thr), inclusive, of Formula (I);

Formula (I):
```
1                                       10
Met—Thr—Ala—Pro—Gly—Ala—Ala—Gly—Arg—Cys—
                                        20
Pro—Pro—Thr—Thr—Trp—Leu—Gly—Ser—Leu—Leu—
                                        30
Leu—Leu—Val—Cys—Leu—Leu—Ala—Ser—Arg—Ser—
                                        40
Ile—Thr—Glu—Glu—Val—Ser—Glu—Tyr—Cys—Ser—
                                        50
His—Met—Ile—Gly—Ser—Gly—His—Leu—Gln—Ser—
                                        60
Leu—Gln—Arg—Leu—Ile—Asp—Ser—Gln—Met—Glu—
                                        70
Thr—Ser—Cys—Gln—Ile—Thr—Phe—Glu—Phe—Val—
                                        80
Asp—Gln—Glu—Gln—Leu—Lys—Asp—Pro—Val—Cys—
                                        90
Tyr—Leu—Lys—Lys—Ala—Phe—Leu—Leu—Val—Gln—
                                        100
X—Ile—Met—Glu—Asp—Thr—Met—Arg—Phe—Arg—
                                        110
Asp—Asn—Thr—Pro—Asn—Ala—Ile—Ala—Ile—Val—
                                        120
Gln—Leu—Gln—Glu—Leu—Ser—Leu—Arg—Leu—Lys—
                                        130
Ser—Cys—Phe—Thr—Lys—Asp—Tyr—Glu—Glu—His—
                                        140
Asp—Lys—Ala—Cys—Val—Arg—Thr—Phe—Tyr—Glu—
                                        150
Thr—Pro—Leu—Gln—Leu—Leu—Glu—Lys—Val—Lys—
                                        160
Asn—Val—Phe—Asn—Glu—Thr—Lys—Asn—Leu—Leu—
                                        170
Asp—Lys—Asp—Trp—Asn—Ile—Phe—Ser—Lys—Asn—
                                        180
Cys—Asn—Asn—Ser—Phe—Ala—Glu—Cys—Ser—Ser—
                                        190
Gln—Asp—Val—Val—Thr—Lys—Pro—Asp—Cys—Asn—
                                        200
Cys—Leu—Tyr—Pro—Lys—Ala—Ile—Pro—Ser—Ser—
```

```
                                          210
Asp—Pro—Ala—Ser—Val—Ser—Pro—His—Gln—Pro—
                                          220
Leu—Ala—Pro—Ser—Met—Ala—Pro—Val—Ala—Gly—
                                          230
Leu—Thr—Trp—Glu—Asp—Ser—Glu—Gly—Thr—Glu—
                                          240
Gly—Ser—Ser—Leu—Leu—Pro—Gly—Glu—Gln—Pro—
                                          250
Leu—His—Thr—Val—Asp—Pro—Gly—Ser—Ala—Lys—
                                          260
Gln—Arg—Pro—Pro—Arg—Ser—Thr—Cys—Gln—Ser—
                                          270
Phe—Glu—Pro—Pro—Glu—Thr—Pro—Val—Val—Lys—
                                          280
Asp—Ser—Thr—Ile—Gly—Gly—Ser—Pro—Gln—Pro—
                                          290
Arg—Pro—Ser—Val—Gly—Ala—Phe—Asn—Pro—Gly—
                                          300
Met—Glu—Asp—Ile—Leu—Asp—Ser—Ala—Met—Gly—
                                          310
Thr—Asn—Trp—Val—Pro—Glu—Glu—Ala—Ser—Gly—
                                          320
Glu—Ala—Ser—Glu—Ile—Pro—Val—Pro—Gln—Gly—
                                          330
Thr—Glu—Leu—Ser—Pro—Ser—Arg—Pro—Gly—Gly—
                                          340
Gly—Ser—Met—Gln—Thr—Glu—Pro—Ala—Arg—Pro—
                                          350
Ser—Asn—Phe—Leu—Ser—Ala—Ser—Ser—Pro—Leu—
                                          360
Pro—Ala—Ser—Ala—Lys—Gly—Gln—Gln—Pro—Ala—
                                          370
Asp—Val—Thr—Gly—Thr—Ala—Leu—Pro—Arg—Val—
                                          380
Gly—Pro—Val—Arg—Pro—Thr—Gly—Gln—Asp—Trp—
                                          390
Asn—His—Thr—Pro—Gln—Lys—Thr—Asp—His—Pro—
                                          400
Ser—Ala—Leu—Leu—Arg—Asp—Pro—Pro—Glu—Pro—
                                          410
Gly—Ser—Pro—Arg—Ile—Ser—Ser—Pro—Arg—Pro—
                                          420
Gln—Gly—Leu—Ser—Asn—Pro—Ser—Thr—Leu—Ser—
                                          430
Ala—Gln—Pro—Gln—Leu—Ser—Arg—Ser—His—Ser—
                                          440
Ser—Gly—Ser—Val—Leu—Pro—Leu—Gly—Glu—Leu—
                                          450
Glu—Gly—Arg—Arg—Ser—Thr—Arg—Asp—Arg—Arg—
                                          460
Ser—Pro—Ala—Glu—Pro—Glu—Gly—Gly—Pro—Ala—
                                          470
Ser—Glu—Gly—Ala—Ala—Arg—Pro—Leu—Pro—Arg—
                                          480
Phe—Asn—Ser—Val—Pro—Leu—Thr—Asp—Thr—Gly—
                                          490
His—Glu—Arg—Gln—Ser—Glu—Gly—Ser—Ser—Ser—
                                          500
Pro—Gln—Leu—Gln—Glu—Ser—Val—Phe—His—Leu—
                                          510
Leu—Val—Pro—Ser—Val—Ile—Leu—Val—Leu—Leu—
                                          520
Ala—Val—Gly—Gly—Leu—Leu—Phe—Tyr—Arg—Trp—
                                          530
Arg—Arg—Arg—Ser—His—Gln—Glu—Pro—Gln—Arg—
                                          540
Ala—Asp—Ser—Pro—Leu—Glu—Gln—Pro—Glu—Gly—
                                          550
Ser—Pro—Leu—Thr—Gln—Asp—Asp—Arg—Gln—Val—
                                          554
Glu—Leu—Pro—Val
``` wherein X is Tyr or Asp.

4. The host cell of claim 3, wherein said expression plasmid is selected from the group consisting of pIN-III (lpp$^P$-5)-OmpA-MCSF11-NV151 and pIN-III(lpp$^P$-5)-OmpA-MCSF11-NV143.

\* \* \* \* \*